(12) United States Patent
Bobilev et al.

(10) Patent No.: US 12,156,872 B2
(45) Date of Patent: Dec. 3, 2024

(54) COMBINATION THERAPIES FOR TREATING CANCER

(71) Applicants: TESARO, Inc., Waltham, MA (US); MERCK SHARP & DOHME B.V.

(72) Inventors: Dmitri Bobilev, Newton, MA (US); Bruce Dezube, Newton, MA (US); Peng Sun, New Providence, NJ (US); Andrew R. Ferguson, Hingham, MA (US)

(73) Assignees: TESARO, Inc., Waltham, MA (US); MERCK SHARP & DOHME B.V., Haarlem (NL)

( * ) Notice: Subject to any disclaimer, the term of this patent is extended or adjusted under 35 U.S.C. 154(b) by 732 days.

(21) Appl. No.: 16/612,363

(22) PCT Filed: May 9, 2018

(86) PCT No.: PCT/US2018/031876
§ 371 (c)(1),
(2) Date: Nov. 8, 2019

(87) PCT Pub. No.: WO2018/208968
PCT Pub. Date: Nov. 15, 2018

(65) Prior Publication Data
US 2020/0289493 A1    Sep. 17, 2020

Related U.S. Application Data

(60) Provisional application No. 62/648,327, filed on Mar. 26, 2018, provisional application No. 62/646,332, filed on Mar. 21, 2018, provisional application No. 62/634,789, filed on Feb. 23, 2018, provisional application No. 62/556,255, filed on Sep. 8, 2017, provisional application No. 62/508,359, filed on May 18, 2017, provisional application No. 62/503,879, filed on May 9, 2017.

(51) Int. Cl.
| | |
|---|---|
| *A61K 31/454* | (2006.01) |
| *A61K 39/395* | (2006.01) |
| *A61P 35/00* | (2006.01) |
| *A01K 1/01* | (2006.01) |
| *G06T 7/215* | (2017.01) |
| *H01R 13/516* | (2006.01) |

(52) U.S. Cl.
CPC ........ *A61K 31/454* (2013.01); *A61K 39/3955* (2013.01); *A61P 35/00* (2018.01); *A01K 1/01* (2013.01); *G06T 7/215* (2017.01); *H01R 13/516* (2013.01)

(58) Field of Classification Search
CPC .......................... A61P 35/00; A61K 39/3955
See application file for complete search history.

(56) References Cited

U.S. PATENT DOCUMENTS

| | | | |
|---|---|---|---|
| 7,595,048 B2 | 9/2009 | Honjo et al. | |
| 8,071,623 B2 | 12/2011 | Jones et al. | |
| 8,217,149 B2 | 7/2012 | Irving et al. | |
| 8,436,185 B2 | 5/2013 | Foley et al. | |
| 8,728,474 B2 | 5/2014 | Honjo et al. | |
| 8,779,108 B2 | 7/2014 | Queva et al. | |
| 8,952,136 B2 | 2/2015 | Carven et al. | |
| 9,624,298 B2 | 4/2017 | Nastri et al. | |
| 9,707,302 B2 | 7/2017 | Goldenberg et al. | |
| 9,815,897 B2 | 11/2017 | King et al. | |
| 10,738,117 B2 | 8/2020 | King et al. | |
| 2009/0123419 A1 | 5/2009 | Sherman et al. | |
| 2010/0003192 A1 | 1/2010 | Sherman et al. | |
| 2010/0286203 A1 | 11/2010 | Foley et al. | |
| 2011/0118217 A1 | 5/2011 | Gudmundsson et al. | |
| 2012/0207856 A1 | 8/2012 | Ajay et al. | |
| 2012/0269861 A1 | 10/2012 | Sherman et al. | |
| 2015/0071910 A1 | 3/2015 | Kowanetz et al. | |
| 2015/0344968 A1 | 12/2015 | Johnson | |
| 2016/0075783 A1 | 3/2016 | King et al. | |
| 2016/0296633 A1 | 10/2016 | Goldenberg et al. | |
| 2016/0340428 A1 | 11/2016 | Yang | |
| 2017/0000885 A1* | 1/2017 | Rhee .................. | C07K 16/2827 |
| 2017/0049767 A1 | 2/2017 | Blanchette et al. | |
| 2018/0311224 A1 | 11/2018 | Hedley et al. | |
| 2020/0016142 A1 | 1/2020 | McGurk et al. | |
| 2020/0017462 A1 | 1/2020 | Wu et al. | |
| 2020/0055837 A1 | 2/2020 | Stewart et al. | |

(Continued)

FOREIGN PATENT DOCUMENTS

| | | |
|---|---|---|
| CN | 105960415 A | 9/2016 |
| CN | 106132439 A | 11/2016 |

(Continued)

OTHER PUBLICATIONS

Liu et al, What is the Place of PARP Inhibitors in Ovarian Cancer Treatment?, Curr Oncol Rep, 2016, 18:29, p. 1-9 (Year: 2016).*
Clinicaltrials.Gov, (2016). "NCT02657889: Niraparib in Combination With Pembrolizumab in Patients With Triple-negative Breast Cancer or Ovarian Cancer," Available online at <https://clinicaltrials.gov/ct2/show/NCT02657889>, 8 pages.
Dougherty et al., (2017). "Biological and clinical evidence for somatic mutations in BRCA1 and BRCA2 as predictive markers for olaparib response in high-grade serous ovarian cancers in the maintenance setting," Oncotarget, 8(27):43653-43661.

(Continued)

*Primary Examiner* — Mark Halvorson
*Assistant Examiner* — Dennis J Sullivan
(74) *Attorney, Agent, or Firm* — Finnegan, Henderson, Farabow, Garrett & Dunner LLP

(57) ABSTRACT

The present invention provides methods of treatment for recurrent cancer(s) through combination therapy with an agent that inhibits programmed death-1 protein (PD-1) signaling and an agent that inhibits poly [ADP-ribose] polymerase (PARP) signaling.

24 Claims, 11 Drawing Sheets

Specification includes a Sequence Listing.

(56) References Cited

U.S. PATENT DOCUMENTS

| | | |
|---|---|---|
| 2020/0289493 A1 | 9/2020 | Bobilev et al. |
| 2020/0299387 A1 | 9/2020 | Mikule |
| 2020/0306236 A1 | 10/2020 | Mikule |
| 2021/0008053 A1 | 1/2021 | Sun et al. |
| 2021/0106574 A1 | 4/2021 | Feng et al. |
| 2022/0048983 A1 | 2/2022 | Milenkova-Ilieva et al. |

FOREIGN PATENT DOCUMENTS

| | | |
|---|---|---|
| EA | 201992594 | 3/2020 |
| EP | 0325199 | 10/1993 |
| EP | 0357061 | 6/1994 |
| EP | 2007733 | 5/2016 |
| EP | 3621592 | 3/2020 |
| JP | 2011/509252 | 3/2011 |
| JP | 2011/509253 | 3/2011 |
| JP | 2017/504623 | 2/2017 |
| WO | WO 2007/113596 | 10/2007 |
| WO | WO-2008084261 A1 | 7/2008 |
| WO | WO 2009/064738 | 5/2009 |
| WO | WO-2009087381 A1 | 7/2009 |
| WO | WO 2010/091140 | 8/2010 |
| WO | WO 2011/160063 | 12/2011 |
| WO | WO-2011153383 A1 | 12/2011 |
| WO | WO 2012/027224 | 3/2012 |
| WO | WO 2013/182645 | 12/2013 |
| WO | WO 2014/088983 | 6/2014 |
| WO | WO 2014/088984 | 6/2014 |
| WO | WO 2014/138101 | 9/2014 |
| WO | WO-2014179664 A2 | 11/2014 |
| WO | WO-2015086473 A1 | 6/2015 |
| WO | WO 2015/108986 A1 | 7/2015 |
| WO | WO 2015/116868 | 8/2015 |
| WO | WO 2015/119930 A1 | 8/2015 |
| WO | WO 2015/153514 A1 | 10/2015 |
| WO | WO 2015/184145 | 12/2015 |
| WO | WO 2016/094391 | 6/2016 |
| WO | WO 2016/126858 | 8/2016 |
| WO | WO 2016/161270 | 10/2016 |
| WO | WO 2016/200835 | 12/2016 |
| WO | WO 2016/210108 | 12/2016 |
| WO | WO 2017/075091 | 5/2017 |
| WO | WO 2017/142871 | 8/2017 |
| WO | WO-2018005818 A1 | 1/2018 |
| WO | WO 2018/059437 | 4/2018 |
| WO | WO 2018/085468 | 5/2018 |
| WO | WO 2018/085469 | 5/2018 |
| WO | WO 2018/129553 | 7/2018 |
| WO | WO 2018/129559 | 7/2018 |
| WO | WO 2018/200517 | 11/2018 |
| WO | WO 2018/201096 | 11/2018 |
| WO | WO 2018/208968 | 11/2018 |
| WO | WO 2018/213732 | 11/2018 |
| WO | WO-2018201096 A1 | 11/2018 |
| WO | WO 2019/005762 | 1/2019 |
| WO | WO 2019/067634 | 4/2019 |
| WO | WO 2019/067978 | 4/2019 |
| WO | WO 2019/071123 | 4/2019 |
| WO | WO 2019/133697 | 7/2019 |
| WO | WO 2019/152989 | 8/2019 |

OTHER PUBLICATIONS

Extended European Search Report and Written Opinion dated Feb. 11, 2021, for EP Patent Application No. 18797986.9, 16 pages.
Gadducci et al., (2017). "PARP inhibitors alone and in combination with other biological agents in homologous recombination deficient epithelial ovarian cancer: From the basic research to the clinic," Critical Reviews in Oncology/Hematology, 114:153-165.
Goyal et al., (2016). "Hereditary cancer syndromes: utilizing DNA repair deficiency as therapeutic target," Familial Cancer, 15(3):359-366.
Konstantinopoulos et al., (2017). "Dose-finding combination study of niraparib and pembrolizumab in patients (pts) with metastatic triple-negative breast cancer (TBNC) or recurrent platinum-resistant epithelial ovarian cancer (OC) (TOPACIO/Keynote-162)," Annals of Oncology, 28(5):406-407.
Zhu et al., (2017). "Programmed death-1 pathway blockade produces a synergistic antitumor effect: combined application in ovarian cancer," Journal of Gynecologic Oncology, 28(5):e64, 19 pages.
Adams et al., (2017). "Phase 2 study of pembrolizumab (pembro) monotherapy for previously treated metastatic triple-negative breast cancer (mTNBC): Keynote-086 cohort A," J Clin Oncol., 35(15):1008. Abstract Only.
Agata et al., (1996). "Expression of the PD-1 antigen on the surface of stimulated mouse T and B lymphocytes," Int Immunol., 8(5):765-72.
Ascierto et al., (2013). "Biomarkers for Immunostimulatory Monoclonal Antibodies in Combination Strategies for Melanoma and Other Tumor Types," Clin. Cancer. Res., 19(5): 1009-1020.
Australian Government Department of Health, (2014). "MSAC Application 1380: Germline BRCA mutation testing to determine eligibility for olaparib maintenance therapy in women with platinum-sensitive relapsed ovarian cancer (including fallopian tube or primary peritoneal cancer) with high grade serous features or a high grade serous component," 32 pages.
Barber et al., (2006). "Restoring function in exhausted CD8 T cells during chronic viral infection," Nature, 439: 682-687.
Bennett et al., (2003). "Program death-1 engagement upon TCR activation has distinct effects on costimulation and cytokine-driven proliferation: attenuation of ICOS, IL-4, and IL-21, but not CD28, IL-7, and IL-15 responses," J. Immunol., 170:711-8.
Berge et al., (1977). "Pharmaceutical salts," J Pharm Sci., 66, 1-19.
Bertsias et al., (2008). "Genetic, immunologic, and immunohistochemical analysis of the programmed death 1/programmed death ligand 1 pathway in human systemic lupus erythematosus," Arthritis Rheum., 60(1): 207-218.
Bhatia et al., (2011). "Immunobiology of Merkel cell carcinoma: implications for immunotherapy of a polyomavirus-associated cancer," Curr. Oncol. Rep., 13(6): 488-497.
Blank et al., (2004). "PD-L1/B7H-1 inhibits the effector phase of tumor rejection by T cell receptor (TCR) transgenic CD8+ T cells," Cancer Res., 64(3): 1140-1145.
Boland et al., (2010). "Microsatellite instability in colorectal cancer," Gastroenterology, 138(6):2073-2087.
Brown et al, (2003). "Blockade of programmed death-1 ligands on dendritic cells enhances T cell activation and cytokine production," J. Immunol., 170: 1257-1266.
De la Chapelle et al., (2010). "Clinical relevance of microsatellite instability in colorectal cancer," J Clin Oncol., 28(20):3380-7.
Domagala et al., (2016). "'BRCA 1/2-negative hereditary triple-negative breast cancers exhibit BRCAness," International Journal of Cancer, 140:1545-1550.
Dong et al., (2002). "Tumor-associated B7-H1 promotes T-cell apoptosis: a potential mechanism of immune evasion," Nat. Med., 8:793-800.
Du Bois et al., (2006). "Addition of Epirubicin As a Third Drug to Carboplatin-Paclitaxel in First-Line Treatment of Advanced Ovarian Cancer: A Prospectively Randomized Gynecologic Cancer Intergroup Trial by the Arbeitsgemeinschaft Gynaekologische Onkologie Ovarian Cancer Study Group and the Groupe d'Investigateurs Nationaux pour l'Etude des Cancers Ovariens," Journal of Clinical Oncology, 24(7):1127-1135.
Duggan et al., (1994). "Microsatellite instability in sporadic endometrial carcinoma," J Natl Cancer Inst., 86(16):1216-21.
Eisenhauer et al., (2009). "New response evaluation criteria in solid tumors: Revised RECIST guideline (version 1.1.)," Eur. J. of Cancer, 45:228-247.
Erdal et al., (2017). "A prosurvival DNA damage-induced cytoplasmic interferon response is mediated by end resection factors and is limited by Trex1," Genes Dev., 1:353-369.
Flies et al., (2011). "Blockade of the B7-H1/PD-1 pathway for cancer immunotherapy," Yale Journal of Biology and Medicine, 84(4):409-421.
Freeman et al., (2000). "Engagement of the PD-1 immunoinhibitory receptor by a novel B7 family member leads to negative regulation of lymphocyte activation," J. Exp. Med., 192(7):1027-1034.

(56) References Cited

OTHER PUBLICATIONS

Gelmon et al., (2011). "Olaparib in patients with recurrent high-grade serous or poorly differentiated ovarian carcinoma or triple-negative breast cancer: a phase 2, multicentre, open-label, non-randomised study," Lancet Oncol., 12:852-861.
Greenwald et al., (2005). "The B7 family revisited," Annu. Rev. Immunol., 23:515-548.
Gurin et al., (1999). "Causes and consequences of microsatellite instability in endometrial carcinoma," Cancer Res., 59:462-466.
Hamanishi et al., (2007). "Programmed cell death 1 ligand 1 and tumor-infiltrating CD8+ T Tymphocytes are prognostic factors of human ovarian cancer," Proc. Natl. Acad. Sci. USA, 104: 3360-335.
Hamanishi et al., (2015). "Safety and Antitumor Activity of Anti-PD-1 Antibody, Nivolumab, in Patients With Platinum-Resistant Ovarian Cancer," J Clin Oncol., 33:4015-4022.
Heong et al., (2016). "Update on immune checkpoint inhibitors in gynecological cancers," Journal of Gynecologic Oncology, 28(2):1-19.
Higuchi et al., (2015). "CTLA-4 Blockade Synergizes Therapeutically with PARP Inhibition in BRCA1-Deficient Ovarian Cancer," Cancer Immunol Res., 3:1257-1268.
Hirano et al., (2005). "Blockade of B7-H1 and PD-1 by monoclonal antibodies potentiates cancer therapeutic immunity," Cancer Res., 65:1089-1096.
Huang et al., (2015). "The PARP1 inhibitor BMN 673 exhibits immunoregulatory effects in a Brca1(-/-) murine model of ovarian cancer," Biochem Biophys Res Commun., 463:551-556.
International Search Report and Written Opinion dated Aug. 6, 2018, for PCT Patent Application No. PCT/US2018/031876 filed on May 9, 2018, 19 pages.
Ishida et al., (1992). "Induced expression of PD-1, a novel member of the immunoglobulin gene superfamily, upon programmed cell death," Embo J., 11: 3887-95.
Iwai et al., (2002). "Involvement of PD-L1 on tumor cells in the escape from host immune system and tumor immunotherapy by PD-L1 blockade," Proc. Nat.l Acad. Sci. USA, 99(9):12293-12297.
Iwai et al., (2004). "PD-1 blockade inhibits hematogenous spread of poorly immunogenic tumor cells by enhanced recruitment of effector T cells," Int. Immunol., 17:133-144.
Javle et al., (2011). "The role of PARP in DNA repair and its therapeutic exploitation," British Journal of Cancer, 105(8):1114-1122.
Jiao et al., (2017). "PARP Inhibitor Upregulates PD-L1 Expression and Enhances Cancer-Associated Immunosuppression," Clin Cancer Res., 23:3711-3720.
Konstantinopoulos et al., (2018). "Topacio: Preliminary activity and safety in patients (pts) with platinum-resistant ovarian cancer (PROC) in a phase 1/2 study of niraparib in combination with pembrolizumab," Gynecologic Oncology, 149(1):246. Abstract only.
Konstantinopoulos, (2018). "Pembrolizumab Plus Niraparib Shows Promise in Ovarian Cancer," Onclive, Retrieved from the Internet: <https://www.onclive.com/conference-coverage/sgo-2018/pembrolizumab-plus-niraparib-shows-promise-in-ovarian-cancer>, 2 pages.
Kroner et al., (2005). "A PD-1 polymorphism is associated with disease progression in multiple sclerosis," Ann. Neurol., 58(1):50-57.
Latchman et al., (2001). "PD-L2 is a second ligand for PD-1 and inhibits T cell activation," Nat. Immunol., 2(3):261-238.
Le et al., (2015). "PD-1 Blockade in Tumors with Mismatch-Repair Deficiency," N. Engl. J. Med. 372(26):2509-2520.
Moschetta et al., (2016). "BRCA somatic mutations and epigenetic BRCA modifications in serous ovarian cancer," Annals of Oncology, 27(8):1448-1455.
Mouw et al., (2017). "DNA Damage and Repair Biomarkers of Immunotherapy Response," Cancer Discov., 7:675-693.
Murali et al., (2014). "Classification of endometrial carcinoma: more than two types," Lancet Oncol., 15(7):e268-78.
Myers et al., (1988). "Optimal alignments in linear space," CABIOS, 4:11-17.

Ni et al., (2007). "PD-1 gene haplotype is associated with the development of type 1 diabetes mellitus in Japanese children," Hum. Genet., 121(2): 223-232.
Nielsen et al., (2003). "Association of a putative regulatory polymorphism in the PD-1 gene with susceptibility to type 1 diabetes," Tissue Antigens, 62(6):492-497.
Nishimura et al., (1999). "Development of lupus-like autoimmune diseases by disruption of the PD-1 gene encoding an ITIM motif-carrying immunoreceptor," Immunity, 11:141-1151.
Okazaki et al., (2002). "New regulatory co-receptors: inducible co-stimulator and PD-1," Curr. Opin. Immunol, 14:391779-82.
Parry et al., (2005). "CTLA-4 and PD-1 receptors inhibit T-cell activation by distinct mechanisms," Mol. Cell. Biol., 25:9543-9553.
Patnaik et al., (2012). "Phase I study of MK-3475 (anti-PD-1 monoclonal antibody) in patients with advanced solid tumors," Journal of Clinical Oncology, 30(15):2512. Abstract only.
Pfisterer et al., (2006). "Gemcitabine plus carboplatin compared with carboplatin in patients with platinum-sensitive recurrent ovarian cancer: an intergroup trial of the AGO-OVAR, the NCIC CTG, and the EORTC GCG," J Clin Oncol., 24(29):4699-707.
Popat et al., (2005). "Systematic review of microsatellite instability and colorectal cancer prognosis," J Clin Oncol., 23(3):609-18.
Porichis et al., (2012). "Role of PD-1 in HIV pathogenesis and as target for therapy," Curr. HIV/AIDS Rep., 9(1):81-90.
Rustin et al., (2011). "Definitions for response and progression in ovarian cancer clinical trials incorporating RECIST 1.1 and CA 125 agreed by the Gynecological Cancer Intergroup (GCIG)," Int J Gynecol Cancer, 21:419-423.
Sandhu et al., (2013). "The poly(ADP-ribose) polymerase inhibitor niraparib (MK4827) in BRCA mutation carriers and patients with sporadic cancer: a phase 1 dose-escalation trial," Lancet Oncol., 14:882-892.
Sharpe et al., (2007). "The function of programmed cell death 1 and its ligands in regulating autoimmunity and infection," Nat. Immunol., 8:239-245.
Tahoori et al., (2011). "Association of programmed cell death-1 (PDCD-1) gene polymorphisms with rheumatoid arthritis in Iranian patients," Clin. Exp. Rheumatol., 29(5):763-767.
Tang et al., (2013). "Programmed death 1 pathway inhibition in metastatic renal cell cancer and prostate cancer," Current Oncology Reports, 15(2):98-104.
Topalian et al., (2012). "Safety, activity, and immune correlates of anti-PD-1 antibody in cancer," New England J. Med., 366:2443-2454.
Umar et al., (2004). "Revised Bethesda Guidelines for hereditary nonpolyposis colorectal cancer (Lynch syndrome) and microsatellite instability," J Natl Cancer Inst., 96(4):261-8.
Weber, (2010). "Immune checkpoint proteins: a new therapeutic paradigm for cancer-preclinical background: CTLA-4 and PD-1 blockade," Semin. Oncol., 37(5):430-439.
Westdorp et al., (2016). "Opportunities for immunotherapy in microsatellite instable colorectal cancer," Cancer Immunol. Immunother., 65(10):1249-1259.
Yamazaki et al., (2002). "Expression of programmed death 1 ligands by murine T cells and APC," J. Immunol., 169(10):5538-5545.
Boyer, "Medical Oncology" in "Cancer: A Comprehensive Clinical Guide," Harwood Academic Publishers, 2005, 41-49.
Brown et al.. "Combining DNA damaging therapeutics with immunotherapy: more haste, less speed," Br J Cancer, 2017, 118(3):312-324.
ClinicalTrials.gov archive NCT02734004 , [online], Jan. 5, 2017, [search on Apr. 27, 2022],retrieved from the internet,URL:https://clinicaltrials.gov/ct2/history/NCT02734004?V10=View#StudyPageTop, 9 pages.
Clinicaltrials.gov [online], "Phase I/II Study of the Anti-Programmed Death Ligand-1 Durvalumab Antibody (MEDI4736) in Combination With Olaparib and/or Cediranib for Advanced Solid Tumors and Advanced or Recurrent Ovarian, Triple Negative Breast, Lung, Prostate and Colorectal Cancer," NCT02484404, last updated on Jan. 26, 2023, retrieved from URL<https://www.clinicaltrials.gov/ct2/show/NCT02484404>, 14 pages.

(56) References Cited

OTHER PUBLICATIONS

Isnansetyo et al., "Cytotoxicity of Fucoidan from Three Tropical Brown Algae Against Breast and Colon Cancer Cell Lines," Pharmacogn J, 2017, 9(1):14-20.
Konstantinopoulos et al., "Single-Arm Phases 1 and 2 Trial of Niraparib in Combination With Pembrolizumab in Patients With Recurrent Platinum-Resistant Ovarian Carcinoma," Jama Oncol., 2019, 5(8):1141-49.
Kuo et al., "Casuarinin from the Bark of Terminalia arjuna Induces Apoptosis and Cell Cycle Arrest in Human Breast Adenocarcinoma MCF-7 Cells," Planta Med, 2005, 71(3): 237-243.
Liu et al., "What is the Place of PARP Inhibitors in Ovarian Cancer Treatment," Curr Oncol Rep, 2016, 18:29, 9 pages.
Mantovani et al., "The chemokine system in cancer biology and therapy," Cytokine Growth Factor Rev, 2010, 21(1):27-39.
Mirza et al., "Abstract: A phase I study of bevacizumab in combination with niraparib in patients with platinum-sensitive epithelial ovarian cancer: The ENGOT-OV24/AVANOVA1 trial," Journal of Clinical Oncology, May 20, 2016, 34(15_Suppl):5555.
Morales et al., "Review of poly (ADP-ribose) polymerase (PARP) mechanisms of action and rationale for targeting in cancer and other diseases," Crit Rev Eukaryot Gene Expr, 2014, 24(1):15-28.
Robillard et al., "Abstract 3650: Preclinical evaluation of the PARP inhibitor rucaparib in combination with PD-1 and PD-L1 inhibition in a syngeneic BRCA1 mutant ovarian cancer model," Cancer Research, Jul. 1, 2017, 77(13_Supplement):3650.
Stolze et al., "Comparative analysis of KRAS codon 12, 13, 18, 61, and 117 mutations using human MCF10A isogenic cell lines," Sci Rep, 2015, 5, 8535, 9 pages.
Vela et al., "Chemokine receptor-specific antibodies in cancer immunotherapy: achievements and challenges," Frontiers in Immunology, 2015, 6:12, 15 pages.
Yehia et al., "The Clinical Spectrum of PTEN Mutations," Annu Rev Med, 2020, 71:103-116.
U.S. Appl. No. 16/608,059, filed Oct. 24, 2019, Stewart et al.
[No author listed] "Integrated genomic analyses of ovarian carcinoma," Nature, 2011, 474:609-615.
Akbar et al., "A compact vocabulary of paratope-epitope interactions enables predictability of antibody-antigen binding," Cell Reports, Mar. 2021, 34:108856, 21 pages.
Alberts et al., "Analyzing Protein Structure and Function," Molecular Biology of the Cell, 4th edition. New York: Garland Science, 2002, 2 pages.
Aihilli et al., "In vivo anti-tumor activity of the PARP inhibitor niraparib in homologous recombination deficient and proficient ovarian carcinoma," Gynecologic Oncology, 2016, 143:379-388.
Almagro et al., "Humanization of Antibodies," Frontiers in Bioscience, 2008, 13:1619-1633.
Altshuler et al., "Generation of Recombinant Antibodies and Means for Increasing Their Affinity," Biochemistry (Moscow), 2010, 75(13):1584-1605.
American Cancer Society, Cancer Facts & Figures, 2018, 76 pages.
American Cancer Society. Cancer Facts & Figures 2016. Atlanta: American Cancer Society 2016, retrieved on Oct. 26, 2020, retrieved from URL: http://www.cancer.org/acs/groups/content/@research/documents/document/acspc-047079.pdf, 3 pages.
Anderson et al., "TIM-3 in autoimmunity," Current Opinion in Immunology, Dec. 2006, 18:665-669.
Anderson, "Tim-3, a negative regulator of anti-tumor immunity," Current Opinion in Immunology, Apr. 2012, 24(2):213-216.
Andreae et al., "Maturation and activation of dendritic cells induced by lymphocyte activation gene-3 (CD223)," J. Immunol., 2002, 168:3874-3880.
Anonymous, "History of Changes for Study: NCT03308942," Jun. 18, 2018, retrieved on Oct. 26, 2020, retrieved from URL: https://clinicaltrials.gov/ct2/history/NCT03308942?V_5=View#StudyPageTop, 15 pages.
Anonymous, "TESARO announces expansion to second stage of JASPER trial of ZEJULA in combination with TSR-042 in non-small cell lung cancer," Sep. 4, 2018, retrieved on Oct. 26, 2020, retrieved from URL: https://www.globenewswire.com/news-release/2018/09/04/1565255/0/en/TESARO-Announces-Expansion-to-Second-Stage-of-JASPER-Trial-of-ZEJULA-in-Combination-With-TSR-042-in-Non-Small-Cell-Lung-Cancer.html, 4 pages.
Ayers et al., "IFN-γ-related mRNA profile predicts clinical response to PD-1 blockade," J. Clin. Invest., 2017, 127(8):2930-2940.
Baixeras et al., "Characterization of the lymphocyte activation gene 3-encoded protein. A new ligand for human leukocyte antigen class II antigens," J. Exp. Med., 1992, 176:327-337.
Blackburn et al., "Coregulation of CD8+ T cell exhaustion by multiple inhibitory receptors during chronic viral infection," Nat. Immunol., 2009, 10:29-37.
Bohnsack et al., "Adaptation of the immune-related response criteria: iRecist," ESMO, 2014, Abstract 4958.
Bois et al., "A phase I and pharmacokinetic study of novel taxane BMS-188797 and cisplatin in patients with advanced solid tumors," Br. J Cancer, 2006, 94(1):79-84.
Brinkman et al., "The making of bispecific antibodies," Mabs, 2017, 9(2):182-212.
CAS Registry No. 2022215-59-2 Substance Detail, CAS SciFinder, 2016, 5 pages.
Chiba et al., "Tumor-infiltrating DCs suppress nucleic acid-mediated innate immune responses through interactions between the receptor TIM-3 and the alarmin HMGB1," Nature Immunology, Jul. 2012, 13:832-842.
ClinicalTrials.gov [online], "A Study of Niraparib Combined With Bevacizumab Maintenance Treatment in Participants With Advanced Ovarian Cancer Following Response on Front-Line Platinum-Based Chemotherapy," U.S. National Library of Medicine, Oct. 31, 2017, retrieved on Mar. 18, 2022, retrieved from URL <https://clinicaltrials.gov/ct2/show/NCT03326193>, 13 pages.
ClinicalTrials.gov [online], "Avelumab in Patients With MSS, MSI-H and POLE-mutated Recurrent or Persistent Endometrial Cancer and of Avelumab/Talazoparib and Avelumab/Axitinib in Patients With MSS Recurrent or Persistent Endometrial Cancer", U.S. National Library of Medicine, Sep. 23, 2016, retrieved on Aug. 17, 2021, retrieved from URL <https://clinicaltrials.gov/ct2/show/NCT02912572>, 13 pages.
ClinicalTrials.gov [online], "History of Changes for Study: NCT02660034: The Safety, Pharmacokinetics and Antitumor Activity of BGB-A317 in Combination With the BGB-290 in Subjects With Advanced Solid Tumors," U.S. National Library of Medicine, Aug. 13, 2017, retrieved from URL <https://clinicaltrials.govict2/history/NCT02660034?V 4=View#StudyPageTop>, 16 pages.
ClinicalTrials.gov [online], "History of Changes for Study: NCT02849496: Veliparib and Atezolizumab Either Alone or in Combination in Treating Patients With Stage III-IV Triple Negative Breast Cancer", U.S. National Library of Medicine, Sep. 12, 2016, retrieved on Aug. 17, 2021, retrieved from URL <https://clinicaltrials.gov/ct2/history/NCT02849496?V_3=View#StudyPageTop>, 11 pages.
ClinicalTrials.gov [online], "Niraparib in Combination With Cabozantinib (XL184) in Patients With Advanced Urothelial Cancer (Nicaragua) (Nicaragua)," U.S. National Library of Medicine, Feb. 7, 2018, retrieved on Mar. 18, 2022, retrieved from URL <https://clinicaltrials.gov/ct2/show/NCT03425201>, 12 pages.
ClinicalTrials.gov [online], "Niraparib in Combination With Pembrolizumab in Patients With Triple-negative Breast Cancer or Ovarian Cancer (TOPACIO)", Jan. 18, 2016, retrieved on Feb. 16, 2021, retrieved from URL <https://clinicaltrials.gov/ct2/show/NCT02657889?term=NCT+02657889&draw=2&rank=1>, 10 pages.
ClinicalTrials.gov [online], "Niraparib Versus Niraparib-bevacizumab Combination in Women With Platinum-sensitive Epithelial Ovarian Cancer (Avanova)," U.S. National Library of Medicine, Feb. 3, 2015, retrieved on Mar. 18, 2022, retrieved from URL <https://clinicaltrials.gov/ct2/show/NCT02354131>, 10 pages.
ClinicalTrials.gov [online], "Platine, Avastin and OLAparib in 1st Line (PAOLA-1)," U.S. National Library of Medicine, Jun. 23, 2015, retrieved on Mar. 18, 2022, retrieved from URL <https://www.clinicaltrials.gov/ct2/show/NCT02477644>, 11 pages.
Crafton et al., "PARP inhibition and gynecologic malignancies: A review of current literature and on-going trials," Gynecologic Oncology, Jul. 2016, 142(3):588-596.

(56) References Cited

OTHER PUBLICATIONS

Curtin, "Parp Inhibitors and Cancer Therapy," Lands Bioscience and Springer Bioscience, 2006, pp. 218-233.
Dann et al., "BRCA 1/2 mutations and expression: response to platinum chemotherapy in patients with advanced stage epithelial ovarian cancer," Gynecol. Oncol., 2012, 125(3):677-682.
Davies et al., "Antibody-antigen complexes," Annual Rev Biochem., 1990, 59:439-473.
Dedes et al., "Synthetic lethality of PARP inhibition in cancers lacking BRCA1 and BRCA2 mutations," Cell Cycle, 2011, 10(8):1192-1199.
DeKruyff et al., "T Cell/Transmembrane, Ig, and Mucin-3 Allelic Variants Differentially Recognize Phosphatidylserine and Mediate Phagocytosis of Apoptotic Cells," The Journal of Immunology, Feb. 2010, 184(4):1918-1930.
Dockery et al. "Rucaparib: the past, present, and future of a newly approved PARP inhibitor for ovarian cancer," OncoTargets and Therapy, 2017, 10:3029-3037.
Dutcher et al., "A phase II study of interleukin-2 and lymphokine-activated killer cells in patients with metastatic malignant melanoma," J. Clin. Oncol., 1989, 7:477-485.
Edwards et al., "The Remarkable Flexibility of the Human Antibody Repertoire; Isolation of Over One Thousand Different Antibodies to a Single Protein, BLyS," J. Mol. Biol., 2003, 334:103-118.
Evans et al., "PARP inhibitors in ovarian cancer: evidence, experience and clinical potential," Therapeutic Advances in Medical Oncology, Feb. 2017, 9(4):253-267.
Foa et al., "Treatment of acute myeloid leukaemia patients with recombinant interleukin 2: a pilot study," Br. J. Haematol., 1991, 77:491-496.
Freeman et al., "Engagement of the PD-1 Immunoinhibitory Receptor by a Novel B7 Family Member Leads to Negative Regulation of Lymphocyte Activation," J. Exp. Med., 2000, 192(7):1027-1034.
Friedlander et al., "A Phase 1/1b Study of the Anti-PD-1 Monoclonal Antibody BGB-A317 (A317) in Combination with the PARP Inhibitor BGB-290 (290) in Advanced Solid Tumors," American Society of Clinical Oncology, Poster Presentation, Jun. 2, 2017, 1 page.
Gill et al., "Combination of PARP Inhibitor with Temolozolamide Drive PARP1 Trapping and Apoptosis in Ewing's Sarcoma," PLOS One, 2015, 10(10):e0140988.
Grosso et al., "LAG-3 regulates CD8+ T cell accumulation and effector function in murine self-and tumor-tolerance systems," J. Clin. Invest., 2007, 117:3383-92.
Guo et al., "Combined TIM-3 blockade and CD137 activation affords the long-term protection in a murine model of ovarian cancer," Journal of Translational Medicine, 2013, 11:215.
Hamanishi et al., "Immune checkpoint inhibition in ovarian cancer," International Immunology, 2016, 28(7):339-348.
Hamanishi et al., "PD-1/PD-L1 blockade in cancer treatment: perspectives and issues," Int J Clin Oncol, 2016, 21:462-473.
Han et al., "Tim-3: an activation marker and activation limiter of innate immune cells," Frontiers in Immunology, Dec. 2013, 4(449):1-7.
Hao et al., "A new oral polybosphate adenosine ribose polymerase inhibitor—niraparib," Clinical Medication Journal, Jun. 2017, 15(6):13-17 (with English translation).
Hasegawa et al., "Single amino acid substitution in LC-CDR1 induces Russell body phenotype that attenuates cellular protein synthesis through eIF2a phosphorylation and thereby downregulates IgG secretion despite operational secretory pathway traffic," mAbs, 2017, 9(5):854-873.
Hastings et al., "TIM-3 is Expressed on Activated Human CD4+ T Cells and Regulates Th1 and Th17 Cytokines," European Journal of Immunol., Oct. 2009, 39(9):2492-2501.
Hennessy et al., "Somatic Mutations in BRCA1 and BRCA2 Could Expand the Number of Patients That Benefit From Poly (ADP Ribose) Polymerase Inhibitors in Ovarian Cancer," J Clin Oncol., 2010, 28(22):3570-3576.

Heong et al., "Update on immune checkpoint inhibitors in gynecological cancers", Journal of Gynecological Oncology, Mar. 2017, 28(2):e20, 19 pages.
Huang et al., "CEACAM1 regulates TIM-3-mediated tolerance and exhaustion," Nature, 2014, 517(7534):386-390.
Huang et al., "CTLA4 blockade induces frequent tumor infiltration by activated lymphocytes regardless of clinical responses in humans," Clin. Can. Res., 2011, 17:4101-4109.
Huang et al., "Role of LAG-3 in regulatory T cells," Immunity, 2004, 21:503-513.
Huard et al., "Characterization of the major histocompatibility complex class II binding site on LAG-3 protein," Proc. Nail. Acad. Sci. USA, 1997, 94(11):5744-5749.
Huard et al., "Lymphocyte-activation gene 3/major histocompatibility complex class II interaction modulates the antigenic response of CD4+ T lymphocytes," Eur. J. Immunol., 1994, 24:3216-3221.
Huard et al., "T cell major histocompatibility complex class II molecules down-regulate CD4+ T cell clone responses following LAG-3 binding," Eur. J. Immunol., 1996, 26:1180-1186.
Jones et al., "Discovery of 2-{4-[(3S)-Piperidin-3-yl]phenyl}-2H-indazole-7-carboxamide (MK-4827): A Novel Oral Poly(ADP-ribose)polymerase (PARP) Inhibitor Efficacious in BRCA-1 and -2 Mutant Tumors," Journal of Medicinal Chemistry, Oct. 2009, 52(22):7170-7185.
Kane, "TIM Proteins and Immunity," Journal of Immunology, Mar. 2010, 184(6):2743-2749.
Kelley et al., "Targeting DNA repair pathways for cancer treatment: what's new?," Future Oncol., 2014, 10(7):1215-37.
Killmurray, "Niraparib/Bevacizumab Combo Continues to Show Prolonged PFS in Patients With Advanced Ovarian Cancer," Targeted Oncology, Mar. 20, 2021, retrieved on Mar. 18, 2022, retrieved from URL <https://www.targetedonc.com/view/niraparib-bevacizumab-combo-continues-to-show-prolonged-pfs-in-patients-with-advanced-ovarian-cancer>, 3 pages.
Kim et al., "PD-L1 expression on immune cells, but not on tumor cells, is a favorable prognostic factor for head and neck cancer patients," Sci. Rep., 2016, 6:36956.
Konstantinopoulos et al., "Phase I/II study of niraparib plus pembrolizumab in patients with triple-negative breast cancer or recurrent ovarian cancer," Meeting Abstract I 2016 ASCO Annual Meeting, re-printed in Journal of Clinical Oncology, 2016, 34(15), Suppl., 4 pages.
Konstantinopoulos, "Pembrolizumab Plus Niraparib Shows Promise in Ovarian Cancer", SGO Annual Meeting, Mar. 27, 2018, retrieved on Feb. 16, 2021, retrieved from URL <https://www.onclive.com/view/pembrolizumab-plus-niraparib-shows-promise-in-ovarian-cancer, 3 pages.
Landrum et al., "A phase 1 trial of pegylated liposomal doxorubicin (PLD), carboplatin, bevacizumab and veliparib in recurrent, platinum-sensitive ovarian, primary peritoneal, and fallopian tube cancer: An NRG Oncology/Gynecologic Oncology Group study," Gynecologic Oncology, Nov. 2015, 140(2):204-209.
Ledermann et al., "Olaparib maintenance therapy in patients with platinum-sensitive relapsed serous ovarian cancer: a preplanned retrospective analysis of outcomes by BRCA status in a radomised phase 2 trial," The Lancet, 2014, 15(8):852-61.
Ledermann et al., "Olaparib Maintenance Therapy in Platinum-Sensitive Relapsed Ovarian Cancer," New England Journal of Medicine, 2012, 366:1382-92.
Lee et al., "Safety and Clinical Activity of the Programmed Death-Ligand 1 Inhibitor Durvalumab in Combination With Poly (ADP-Ribose) Polymerase Inhibitor Olaparib or Vascular Endothelial Growth Factor Receptor 1-3 Inhibitor Cediranib in Women's Cancers: A Dose-Escalation, Phase I Study," Journal of Clinical Oncology, Jul. 2017, 35(19):2193-2202.
Liberal et al., "The Impaired Immune Regulation of Autoimmune Hepatitis Is Linked to a Defective Galectin-9/Tim-3 Pathway," Hepatology, 2012, 56(2):677-686.
Lippow et al., "Computational design of antibody-affinity improvement beyond in vivo maturation," Nature Biotechnology, 2007, 25(10):1171-1176.

(56) References Cited

OTHER PUBLICATIONS

Lo et al., "Conformational epitope matching and prediction based on protein surface spiral features," BMC Genomics, 2021, 22(Suppl. 2): 116, 16 pages.

Lotze et al., "Interleukin 2," K.A. Smith, Academic Press, Inc., San Diego, Calif., 1988, 237.

Malmqvist, "Biospecific interaction analysis using biosensor technology," Nature, 1993, 361:186-187.

Marchalonis et al., "The antibody repertoire in evolution: Chance, selection, and continuity," Developmental & Comparative Immunology, 2006, 30:223-247.

Marchetti et al., "Olaparib, PARP1 inhibitor in ovarian cancer," Expert Opinion on Investigational Drugs, Jul. 2012, 21(10):1575-1584.

Marks et al., "How repertoire data are changing antibody science," J. Biol. Chem., 2020, 295(29):9823-9837.

McLachlan et al., "The current status of PARP inhibitors in ovarian cancer," Tumori: A Journal of Experimental and Clinical Oncology, Oct. 2016, 102(5):433-444.

Mendes-Pereira et al., "Synthetic lethal targeting of PTEN mutant cells with PARP inhibitors," EMBO Molecular Medicine, 2009, 1:315-322.

Miller et al., "The status of poly(adenosine diphosphate-ribose) polymerase (PARP) inhibitors in ovarian cancer, part 2: extending the scope beyond olaparib and BRCA1/2 mutations," Clinical Advances in Hematology & Oncology, 2016, 14(9):704-711.

Mirza et al., "Niraparib Maintenance Therapy in Platinum-Sensitive Recurrent Ovarian Cancer," The New England Journal of Medicine, 2016, 375(22):2154-2164.

Mirza et al., "Niraparib plus bevacizumab versus niraparib alone for platinum-sensitive recurrent ovarian cancer (NSGO-AVANOVA2/ENGOT-ov24): a randomised, phase 2, superiority trial," Lancet Oncology, Aug. 29, 2019, pp. 1-11.

Monney et al., "Th1-specific cell surface protein Tim-3 regulates macrophage activation and severity of an autoimmune disease," Nature, Jan. 2002, 415:536-541.

Moschetta et al., "BRCA somatic mutations and epigenetic BRCA modifications in serous ovarian cancer," Annals of Oncology, Aug. 2016, 27(8):1449-1455.

Nakayama et al., "Tim-3 mediates phagocytosis of apoptotic cells and cross-presentation," Blood, Apr. 2009, 113(16):3821-3830.

Ngiow et al., "Anti-TIM3 antibody promotes T cell IFN-γ-mediated antitumor immunity and suppresses established tumors," Cancer Res., 2011, 71:3540-3551.

Ngiow et al., "Prospects for TIM3-Targeted Antitumor Immunotherapy," Cancer Res., 2011, 71(21):6567-6571.

Nishino et al., "Developing a common language for tumor response to immunotherapy: immune-related response criteria using unidimensional measurements," Clin. Cancer Res., 2013, 19(14):3936-43.

Nomi et al., "Clinical significance and therapeutic potential of the programmed death-1 ligand/programmed death-1 pathway in human pancreatic cancer," Clin Cancer Res., 2007, 13:2151-2157.

PCT International Preliminary Report on Patentability in International Application No. PCT/US2018/033437, dated Nov. 19, 2019, 12 pages.

PCT International Preliminary Report on Patentability in International Application No. PCT/US2018/053542, dated Mar. 31, 2020, 5 pages.

PCT International Preliminary Report on Patentability in International Application No. PCT/US2018/054606, dated Apr. 8, 2020, 7 pages.

PCT International Preliminary Report on Patentability in International Application No. PCT/US2018/067653, dated Jun. 30, 2020, 11 pages.

PCT International Preliminary Report on Patentability in International Application No. PCT/US2019/049346, dated Mar. 9, 2021, 15 pages.

PCT International Search Report and Written Opinion in International Application No. PCT/US2018/067653, dated May 27, 2019, 18 pages.

PCT International Search Report and Written Opinion in International Application No. PCT/US2018/053542, dated Dec. 14, 2018, 8 pages.

PCT International Search Report and Written Opinion in International Application No. PCT/US2018/054606, dated Mar. 28, 2019, 11 pages.

PCT International Search Report and Written Opinion in International Application No. PCT/US2019/049346, dated Apr. 9, 2020, 19 pages.

PCT International Search Report dated Oct. 17, 2018 for PCT/US2018/033437, 6 pages.

PCT Invitation to Pay Additional Fees in International Appln. No. PCT/US2018/054606, dated Feb. 5, 2019, 10 pages.

PCT Invitation to Pay Additional Fees in International Appln. No. PCT/US2018/067653, dated Apr. 2, 2019, 18 pages.

PCT Written Opinion of the International Searching Authority dated Oct. 17, 2018 for PCT/US2018/033437, 11 pages.

Pearson, "Using the FASTA program to search protein and DNA sequence databases," Methods Mol. Biol., 1994, 24:307-331.

Pearson, "Using the FASTA program to search protein and DNA sequence databases," Methods Mol. Biol., 1994, 25:365-389.

Popova et al., "Ploidy and large-scale genomic instability consistently identify basal-like breast carcinomas with BRCA1/2 inactivation," Cancer Res, 2012, 72:5454-62.

Qu, "Clinical analysis of 26 cases of ovarian cancer treated with bevacizumab," China Health Care & Nutrition, Dec. 2014, No. 4 (II): 1882 (with English translation).

Richter et al., "On the role of the inhibitory receptor LAG-3 in acute and chronic LCMV infection," International Immunology, Oct. 2009, 22(1):13-23.

Rom-Jurek et al., "Regulation of Programmed Death Ligand 1 (PD-L1) Expression in Breast Cancer Cell Lines In Vitro and in Immunodeficient and Humanized Tumor Mice," Int. J. Mol. Sci., 2018, 16:563.

Rosenberg et al., "A progress report on the treatment of 157 patients with advanced cancer using lymphokine-activated killer cells and interleukin-2 or high-dose interleukin-2 alone," New England Journal of Medicine, 1987, 316(15):889-897.

Rosenberg et al., "The development of new immunotherapies for the treatment of cancer using interleukin-2. A review," Ann. Surgery, 1988, 208:121.

Sakuishi et al., "Emerging Tim-3 functions in anti-microbial and tumor immunity," Trends in Immunology, Aug. 2011, 32(8):345-349.

Sakuishi et al., "Targeting Tim-3 and PD-1 pathways to reverse T cell exhaustion and restore anti-tumor immunity," J. Exp. Med., 2010, 207:2187-2194.

Sameni et al., "Cabozantinib (XL184) inhibits growth and invasion of preclinical TNBC models," Clinical Cancer Research, Oct. 2015, 22(4):923-934.

Schmid et al., "New perspectives in ovarian cancer treatment," Maturitas, Feb. 2014, 77(2):128-136.

Sharma et al., "Primary, Adaptive, and Acquired Resistance to Cancer Immunotherapy," Cell, 2017, 168(4):707-723.

Shukuya et al., "Predictive Markers for the Efficacy of Anti-PD-1/PD-L1 Antibodies in Lung Cancer," Journal of Thoracic Oncology, 2016, 11(7):976-988.

Sierro et al., "The CD4-like molecule LAG-3, biology and therapeutic applications," Expert Opin. Ther. Targets., 2011, 15(1):91-101.

Smith, "Interleukin-2: inception, impact, and implications," Science, 1988, 240(4856):1169-1176.

Sternberg, "Niraparib-Bevacizumab Combo Improves Clinical Outcomes in Recurrent Ovarian Cancer," Cancer Network, Jun. 5, 2020, retrieved on Mar. 18, 2022, retrieved from URL <https://www.cancernetwork.com/view/niraparib-bevacizumab-combo-improves-clinical-outcomes-recurrent-ovarian-cancer>, 2 pages.

(56) References Cited

OTHER PUBLICATIONS

Sulea et al., "Application of Assisted Design of Antibody and Protein Therapeutics (ADAPT) improves efficacy of a Clostridium difficile toxin A single-domain antibody," Scientific Reports, 2018, 8(2260):1-11.
Tentori et al., "Pharmacological Strategies to Increase the Antitumor Activity of Methylating Agents," Current Medicinal Chemistry, 2002, 9(13):1285-1301.
Turner et al., "Hallmarks of 'BRCAness' in sporadic cancers," Nat. Rev. Cancer, 2004, 4(10):814-19.
U.S. Food and Drug Administration, "ZEJULA (niraparib) capsules: Highlights of Prescribing Information," Mar. 2021, 37 pages.
Udall et al., "PD-L1 diagnostic tests: a systematic literature review of scoring algorithms and test-validation metrics," Diagnostic Pathology, 2018, 13:12.
Vajda et al., "Progress toward improved understanding of antibody maturation," Current Opinion in Structural Biology, 2021, 67:226-231.
Vergote et al., "A phase 2 randomised discontinuation trial of cabozantinib in patients with ovarian carcinoma," European Journal of Cancer, 2017, 83:229-236.
Wilcoxen et al., "Homologous recombination deficiency (HRD) score enriches for niraparib sensitive high grade ovarian tumors.," Presented at ASCO, 2015, Abstract #5532, 1 page.
Woo et al., "Immune inhibitory molecules LAG-3 and PD-1 synergistically regulate T-cell function to promote tumoral immune escape," Cancer Res., 2012, 72:917-927.
Woof et al., "Human antibody-Fc receptor interactions illuminated by crystal structures," Nat. Rev. Immunol., 2004, 4:89-99.
Workman et al., "Negative regulation of T cell homeostasis by lymphocyte activation gene-3 (CD223)," J. Immunol., 2005, 174:688-695.
Wu et al., "Blockade of Tim-3 signaling restores the virus-specific CD8+ T-cell response in patients with chronic hepatitis B," European Journal of Immunology, 2012, 42(5):1180-1191.
Zhao et al., "A case of triple-negative breast cancer treated with bevacizumab," Journal of Practical Oncology, Jun. 2009, 24(3):291-292 (with English translation).
Zhu et al., "The Tim-3 ligand galectin-9 negatively regulates T helper type 1 immunity," Nature Immunology, 2005, 6:1245-1252.
Dangi-Garimella, "New PARP Inhibitor, Niraparib, Approved as Maintenance Therapy for Ovarian and Other Cancers," 2017, 4 pages.
Michels et al., "Predictivie biomarkers for cancer therapy witih PARP inhibitors," Oncogene, Jul. 24, 2014, Epub Sep. 16, 2013, 33(30):3894-3907.
Scott, "Niraparib: First Global Approval," Drugs, May 4, 2017;77(9):1029-1034.

\* cited by examiner

COMBINATION THERAPIES FOR TREATING CANCER

CROSS-REFERENCE TO RELATED APPLICATIONS

This application is a U.S. national stage application of PCT/US2018/031876, filed internationally on May 9, 2018, and claims the benefit of U.S. Provisional Application No. 62/503,879, filed May 9, 2017, U.S. Provisional Application No. 62/508,359, filed May 18, 2017, U.S. Provisional Application No. 62/556,255, filed Sep. 8, 2017, U.S. Provisional Application No. 62/634,789, filed Feb. 23, 2018, U.S. Provisional Application No. 62/646,332, filed Mar. 21, 2018, and U.S. Provisional Application No. 62/648,327, filed Mar. 26, 2018, each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 757822000100SEQLIST.TXT, date recorded: Nov. 7, 2019, size: 10 KB).

BACKGROUND

Cancer is a serious public health problem, with about 595,690 people in the United States of America expected to die of cancer in 2016 alone according to the American Cancer Society, Cancer Facts & Figures 2016 (http://www.cancer.org/acs/groups/content/@research/documents/document/acspc-047079.pdf).

SUMMARY

The present disclosure encompasses the recognition that a combination therapy with an agent that inhibits programmed death-1 protein (PD-1) signaling and an agent that inhibits poly [ADP-ribose] polymerase (PARP) is useful for treating certain cancers. In one aspect, the present disclosure provides a method of treating cancer in a subject, wherein the cancer is platinum resistant and the subject is BRCA negative, the method including administering one or both of a therapy that inhibits PD-1 signaling ("anti-PD-1 therapy") and a therapy that inhibits PARP) ("anti-PARP therapy") to a subject so that the subject receives treatment with both therapies.

Among other things, the present disclosure provides the insight that combination therapy with both an agent that inhibits PD-1 signaling and an agent that inhibits PARP may reduce the effective dose of one or both agents.

Agents that inhibit PD-1 signaling include those that bind to and block PD-1 receptors on T cells without triggering inhibitory signal transduction, agents that bind to PD-1 ligands to prevent their binding to PD-1, agents that do both and agents that prevent expression of genes that encode either PD-1 or natural ligands of PD-1. In some embodiments, an agent that inhibits PD-1 signaling is an antibody agent. Anti-PD-1 antibody agents can include any polypeptide or polypeptide complex that includes immunoglobulin structural elements sufficient to confer specific binding. Exemplary antibody agents include, but are not limited to, monoclonal antibodies, polyclonal antibodies, antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR®s. In some embodiments, an antibody agent that inhibits PD-1 signaling is a monoclonal antibody or a derivative thereof. In some embodiments, an antibody agent that inhibits PD-1 signaling is a PD-1 antibody, a PD-L1 antibody, or a derivative thereof. PD-1 and PD-L1 antibodies include, for example, atezolizumab, avelumab, BGB-A317, BI 754091, CX-072, durvalumab, FAZ053, IBI308, INCSHR-1210, JNJ-63723283, JS-001, LY3300054, MEDI-0680, MGA-012, nivolumab, PD-L1 millamolecule, PDR001, pembrolizumab, PF-06801591, REGN-2810, TSR-042, any of the antibodies disclosed in WO2014/179664, and any derivatives thereof. In some certain embodiments, a PD-1 antibody is pembrolizumab or a derivative thereof. In some certain embodiments, an agent includes combinations of agents that inhibit PD-1 signaling.

In some embodiments, agents that inhibit PARP include agents that inhibit PARP-1 and/or PARP-2. In some embodiments, agents that inhibit PARP include ABT-767, AZD 2461, BGB-290, BGP 15, CEP 8983, CEP 9722, DR 2313, E7016, E7449, fluzoparib (SHR 3162), IMP 4297, INO1001, JPI 289, JPI 547, monoclonal antibody B3-LysPE40 conjugate, MP 124, niraparib (ZEJULA) (MK-4827), NU 1025, NU 1064, NU 1076, NU1085, olaparib (AZD2281), ON02231, PD 128763, R 503, R554, rucaparib (RUBRACA) (AG-014699, PF-01367338), SBP 101, SC 101914, Simmiparib, talazoparib (BMN-673), veliparib (ABT-888), WW 46, 2-(4-(Trifluoromethyl)phenyl)-7,8-dihydro-5H-thiopyrano[4,3-d]pyrimidin-4-ol, and salts or derivatives thereof. In some embodiments, an agent that inhibits PARP is a small molecule. In some embodiments, an agent that inhibits PARP is an antibody agent. In some embodiments, an agent that inhibits PARP is niraparib ((3S)-3-[4-{7-(aminocarbonyl)-2H-indazol-2-yl}phenyl]piperidine) or a salt or derivative thereof. In some certain embodiments, an agent includes combinations of agents that inhibit PARP.

In some embodiments, an agent that inhibits PD-1 signaling is administered to a subject who is receiving, has received or will receive treatment with niraparib, an orally active PARP inhibitor. In some certain embodiments, pembrolizumab is administered to a subject who is receiving, has received or will receive treatment with niraparib. In some certain embodiments, niraparib is administered to a subject who is receiving, has received or will receive treatment with pembrolizumab.

In some embodiments, cancers for treatment with combination therapy of the present disclosure include endometrial cancer, breast cancer, ovarian cancer, cervical cancer, fallopian tube cancer, primary peritoneal cancer, colon cancer, squamous cell carcinoma of the anogenital region, melanoma, renal cell carcinoma, lung cancer, non-small cell lung cancer, squamous cell carcinoma of the lung, stomach cancer, bladder cancer, gall bladder cancer, liver cancer, thyroid cancer, laryngeal cancer, salivary gland cancer, esophageal cancer, squamous cell carcinoma of the head and neck, prostate cancer, pancreatic cancer, mesothelioma, Merkel cell carcinoma, sarcoma, and a hematological cancer, such as multiple myeloma, B-cell lymphoma, T-cell lymphoma, Hodgkin's lymphoma/primary mediastinal B-cell lymphoma, and chronic myelogenous leukemia. Other cancers for treatment with combination therapy of the present disclosure may include testicular cancer and cancers of the gastrointestinal tract (i.e. small intestine, rectal cancer).

In some embodiments, cancers for treatment with combination therapy of the present disclosure include cancers of the female reproductive system. In some embodiments, cancers of the female reproductive system include, but are not limited to, ovarian cancer, cancer of the fallopian tube(s), peritoneal cancer, and breast cancer. In some embodiments, the cancer is triple negative breast cancer.

In some embodiments, a cancer for treatment with combination therapy of the present disclosure is platinum resistant. In some embodiments, the subject is BRCA negative. In some embodiments, the subject is gBRCA negative, tBRCA negative, or sBRCA negative. In some embodiments, the subject is tBRCA negative. In some embodiments, the cancer for treatment with combination therapy of the present disclosure is platinum resistant and the subject is BRCA negative.

In some embodiments, the method comprises administering one or both of a therapy that inhibits programmed death-1 protein (PD-1) signaling ("anti-PD-1 therapy") and a therapy that inhibits poly [ADP-ribose] polymerase (PARP) ("anti-PARP therapy") to a subject so that the subject receives treatment with both therapies. In some embodiments, the cancer for treatment is a gynecological cancer or a breast cancer. In some embodiments, the cancer for treatment is selected from: ovarian cancer, cervical cancer, fallopian tube cancer, primary peritoneal cancer, and triple negative breast cancer (TNBC). In some embodiments, the cancer for treatment is PD-L1 negative.

In some embodiments, an anti-PD-1 therapy comprises administration of an agent that inhibits PD-1 signaling. In some embodiments, an agent that inhibits PD-1 signaling is a small molecule, a nucleic acid, a polypeptide (e.g., an antibody), a carbohydrate, a lipid, a metal, or a toxin. In some embodiments, an agent that inhibits PD-1 signaling is an anti-PD-1 antibody agent. In some certain embodiments, an anti-PD-1 antibody agent is a surrogate anti-PD-1 antibody for administration to an animal subject (e.g., a murine antibody for administration to a mouse or rat). In some embodiments, an anti-PD-1 antibody agent is for administration to a human subject.

In some embodiments, an anti-PD-1 antibody agent is an antibody selected from the group consisting of: BGB-A317, BI 754091, IBI308, INCSHR-1210, JNJ-63723283, JS-001, MEDI-0680, MGA-012, nivolumab, PDR001, pembrolizumab, PF-06801591, REGN-2810, TSR-042 and derivatives thereof. In some embodiments, an anti-PD-1 antibody agent is pembrolizumab or a derivative thereof.

In some embodiments, an anti-PD-1 therapy comprises administration of an anti-PD-L1/L2 agent. In some embodiments, an anti-PD-L1/L2 agent is an anti-PD-L1 antibody agent. In some certain embodiments, an anti-PD-L1 antibody agent is a surrogate anti-PD-1 antibody for administration to an animal subject (e.g., a murine antibody for administration to a mouse or rat). In some embodiments, an anti-PD-L1 antibody agent is for administration to a human subject. In some embodiments, an anti-PD-L1 antibody agent is atezolizumab, avelumab, CX-072, durvalumab, FAZ053, LY3300054, PD-L1 millamolecule, or derivatives thereof.

In some embodiments, an anti-PARP therapy comprises administration of an agent that inhibits PARP. In some embodiments, an agent that inhibits PARP is a small molecule, a nucleic acid, a polypeptide (e.g., an antibody), a carbohydrate, a lipid, a metal, or a toxin. In some embodiments, an agent that inhibits PARP is selected from the group consisting of: ABT-767, AZD 2461, BGB-290, BGP 15, CEP 8983, CEP 9722, DR 2313, E7016, E7449, fluzoparib (SHR 3162), IMP 4297, INO1001, JPI 289, JPI 547, monoclonal antibody B3-LysPE40 conjugate, MP 124, niraparib (ZEJULA) (MK-4827), NU 1025, NU 1064, NU 1076, NU1085, olaparib (AZD2281), ONO2231, PD 128763, R 503, R554, rucaparib (RUBRACA) (AG-014699, PF-01367338), SBP 101, SC 101914, Simmiparib, talazoparib (BMN-673), veliparib (ABT-888), WW 46, 2-(4-(Trifluoromethyl)phenyl)-7,8-dihydro-5H-thiopyrano[4,3-d]pyrimidin-4-ol, and salts or derivatives of any of the preceding. In some embodiments, an agent that inhibits PARP is a small molecule. In some embodiments, an agent that inhibits PARP is an antibody agent. In some embodiments, an agent that inhibits PARP is niraparib or a salt or derivative thereof. In some embodiments, an agent that inhibits PARP is a combination of agents.

In some embodiments, a combination therapy comprises administering one or both of an anti-PD-1 therapy and an anti-PARP therapy so that a subject receives both, wherein either or both of the anti-PD-1 therapy and anti-PARP therapy are administered according to a regimen that includes at least one 2-12 week treatment cycle. Treatment duration shall be determined by a medical practitioner. In embodiments, treatment may continue until disease progression or toxicity. In some embodiments a treatment cycle is 2 weeks, 3 weeks, 4 weeks, 5 weeks, 6 weeks, 7 weeks, or 8 weeks. In some embodiments, an anti-PD-1 therapy and an anti-PARP therapy are administered in repeating cycles of 21 days. In some embodiments, an anti-PD-1 therapy is administered on day one of cycle one. In some embodiments, an anti-PD-1 therapy is administered on day one of a subsequent cycle. In some embodiments, an anti-PD-1 therapy is administered between one to three days before or after day one of a subsequent cycle.

In some embodiments, an anti-PD-1 therapy is administered at a dose that is equivalent to 200 mg pembrolizumab or 2 mg/kg of pembrolizumab. In some embodiments, an anti-PD-1 therapy is administered intravenously. In related embodiments, an anti-PD-1 therapy is administered intravenously over about 30 minutes.

In some embodiments, an anti-PD-1 therapy is administered at a dose that is equivalent to 3 mg/kg or 240 mg of nivolumab. In some embodiments, an anti-PD-1 therapy is administered intravenously. In related embodiments, an anti-PD-1 therapy is administered intravenously over about 60 minutes.

In some embodiments, an agent that inhibits PARP is administered at a dose that is less than the FDA-approved dose. In related embodiments, the agent that inhibits PARP may be administered at a dose that is less than the FDA-approved dose for use of the agent as a single agent. In embodiments, an agent that inhibits PARP is niraparib and the niraparib is administered at a dose that is less than the FDA-approved dose. In related embodiments, niraparib is administered at a dose that is less than the FDA-approved dose for use as a single agent. In some embodiments, niraparib is administered at a dose that is less than 300 mg.

In some embodiments, an agent that inhibits PARP is administered at a dose that is equivalent to 200 mg of niraparib once a day. In some embodiments, an agent that inhibits PARP is administered orally. In some embodiments, a dose of 100 mg or 200 mg of niraparib is administered once per day.

In some embodiments, a combination therapy of the present disclosure includes administration of one or both an anti-PD-1 therapy and an anti-PARP therapy so that a subject receives both, include treatment with a dose that is equivalent to 200 mg of niraparib once a day.

In some embodiments, a treatment with a combination therapy of the present disclosure has been demonstrated to achieve clinical benefit in a percentage of patients. In some embodiments, a treatment of the present disclosure has been demonstrated to achieve a clinical benefit in at least 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60% 65%, 70%, 75%, 80%, 85%, or 90% of patients. In some embodiments, a treatment of the present disclosure has been demonstrated to achieve a clinical benefit in an amount within a range bounded by a lower limit and an upper limit, the upper limit being larger than the lower limit. In some embodiments, the lower limit may be about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, or 40% of patients. In some embodiments, the upper limit may be about 10%, 11%, 12%, 13%, 14%, 15%, 16%, 17%, 18%, 19%, 20%, 25%, 30%, 35%, 40%, 45%, 50%, 55%, 60% 65%, 70%, 75%, 85%, or 90% of patients. In some embodiments, a clinical benefit is stable disease ("SD"), a partial response ("PR") and/or a complete response ("CR").

In some embodiments, a cancer for treatment of the present disclosure is platinum refractory.

In some embodiments, the subject has previously been treated with one or more different cancer treatment modalities. In some embodiments, the subject has previously been treated with one or more of radiotherapy, chemotherapy or immunotherapy. In some embodiments, the subject has been treated with one, two, three, four, or five lines of prior therapy. In some embodiments, the subject has been treated with one or two lines of prior therapy. In some embodiments, the subject has been treated with one line of prior therapy. In some embodiments, the subject has been treated with two lines of prior therapy. In some embodiments, a prior therapy is cytotoxic therapy. In some embodiments, the cytotoxic therapy includes chemotherapy.

In some embodiments, wherein a subject has been treated with at least two lines of prior platinum-based therapy, the cancer progressed within six months of the last line of prior platinum-based therapy.

In some embodiments, wherein a subject has been treated with at least two lines of prior platinum-based therapy, the cancer progressed within thirty days of the last line of prior platinum-based therapy In some embodiments are provided methods of treating cancer, where the method includes administering both anti-PD-1 therapy and anti-PARP therapy to the subject.

In one aspect, the present disclosure provides a method of treating cancer, the method including administering one or both of an agent that inhibits PD-1 signaling and an agent that inhibits PARP to a subject so that the subject receives treatment with both, wherein the subject receives treatment with an agent that inhibits PARP is administered at a dose that is less than the FDA-approved dose. In another aspect, the present disclosure provides a method of treating cancer, the method including administering a therapeutically effective amount of an agent that inhibits PARP and an agent that inhibits PD-1 signaling to a subject, wherein the subject is BRCA negative and the cancer is PD-L1 negative. In some embodiments, the cancer for treatment with combination therapy of the present disclosure is recurrent. In some embodiments, the cancer for treatment with combination therapy of the present disclosure is platinum resistant. In some embodiments, the cancer for treatment with combination therapy of the present disclosure is platinum refractory.

In one aspect, the present disclosure provides a method of treating cancer, the method including administering a therapeutically effective amount of an agent that inhibits PARP and an agent that inhibits PD-1 signaling to a subject, wherein the agents are administered to the subject independent of DNA repair status and optionally independent of BRCA status. In another aspect, the present disclosure provides a method of treating cancer, the method including administering a therapeutically effective amount of an agent that inhibits PARP and an agent that inhibits PD-1 signaling to a subject, wherein administration of the agents to the subject is commenced prior to determining the DNA repair status of the subject or the BRCA status of the subject. In some embodiments, the cancer for treatment with combination therapy of the present disclosure is recurrent. In some embodiments, the cancer for treatment with combination therapy of the present disclosure is platinum resistant. In some embodiments, the cancer for treatment with combination therapy of the present disclosure is platinum refractory.

In one aspect, the present disclosure provides a method of treating cancer, the method including administering a therapeutically effective amount of an agent that inhibits PARP and an agent that inhibits PD-1 signaling to a subject, wherein administration of the agents to the subject is commenced in the absence of determining the DNA repair status of the subject or the BRCA status of the subject. In some embodiments, the cancer for treatment with combination therapy of the present disclosure is recurrent. In some embodiments, the cancer for treatment with combination therapy of the present disclosure is platinum resistant. In some embodiments, the cancer for treatment with combination therapy of the present disclosure is platinum refractory.

In some embodiments, the subject is BRCA negative. In some embodiments, the subject is gBRCA negative, tBRCA negative, or sBRCA negative. In some embodiments, the subject is tBRCA negative. In some embodiments, the cancer for treatment is PD-L1 negative. In some embodiments, the subject is BRCA negative and the cancer for treatment with combination therapy is PD-L1 negative.

In some embodiments, a subject has previously been treated with one or more different cancer treatment modalities. In some embodiments, a subject has previously been treated with one or more of radiotherapy, chemotherapy or immunotherapy. In some embodiments, the subject has been treated with one, two, three, four, or five lines of prior therapy. In some embodiments, the subject has been treated with one or two lines of prior therapy. In some embodiments, the subject has been treated with one line of prior therapy. In some embodiments, the subject has been treated with two lines of prior therapy. In some embodiments, the prior therapy is cytotoxic therapy. In some embodiments, cytotoxic therapy includes chemotherapy.

In some embodiments, wherein a subject has been treated with at least two lines of prior platinum-based therapy, the cancer progressed within six months of the last line of prior platinum-based therapy. In some embodiments, wherein a subject has been treated with at least two lines of prior platinum-based therapy, the cancer progressed within thirty days of the last line of prior platinum-based therapy.

In some embodiments, an agent that inhibits PARP is administered at a dose that is equivalent to 200 mg of niraparib daily. In some embodiments, an agent that inhibits PARP is administered orally.

In some embodiments, an agent that inhibits PARP is a small molecule, a nucleic acid, a polypeptide (e.g., an antibody), a carbohydrate, a lipid, a metal, or a toxin. In some embodiments, an agent that inhibits PARP is selected from the group consisting of: ABT-767, AZD 2461, BGB-290, BGP 15, CEP 8983, CEP 9722, DR 2313, E7016, E7449, fluzoparib (SHR 3162), IMP 4297, INO1001, JPI 289, JPI 547, monoclonal antibody B3-LysPE40 conjugate, MP 124, niraparib (ZEJULA) (MK-4827), NU 1025, NU 1064, NU 1076, NU1085, olaparib (AZD2281), ON02231, PD 128763, R 503, R554, rucaparib (RUBRACA) (AG-014699, PF-01367338), SBP 101, SC 101914, Simmiparib, talazoparib (BMN-673), veliparib (ABT-888), WW 46, 2-(4-(Trifluoromethyl)phenyl)-7,8-dihydro-5H-thiopyrano[4,3-d]pyrimidin-4-ol, and salts or derivatives of any of the preceding. In some embodiments, an agent that inhibits PARP is a small molecule. In some embodiments, a small molecule agent that inhibits PARP is selected from the group consisting of: niraparib, olaparib, rucaparib, talazoparib, veliparib, and salts or derivatives thereof. In some embodiments, an agent that inhibits PARP is niraparib or a salt or derivative thereof.

In some embodiments, an agent that inhibits PD-1 signaling is a small molecule, a nucleic acid, a polypeptide (e.g., an antibody), a carbohydrate, a lipid, a metal, or a toxin. In some embodiments, an agent that inhibits PD-1 signaling is an anti-PD-1 antibody agent. In some embodiments, an agent that inhibits PD-1 signaling is an anti-PD-1 antibody selected from the group consisting of: BGB-A317, BI 754091, IBI308, INCSHR-1210, JNJ-63723283, JS-001, MEDI-0680, MGA-012, nivolumab, PDR001, pembrolizumab, PF-06801591, REGN-2810, TSR-042, and derivatives thereof. In some embodiments, an anti-PD-1 antibody is pembrolizumab or a derivative thereof.

In some embodiments, an anti-PD-1 therapy comprises administration of an anti-PD-L1/L2 agent. In some embodiments, an anti-PD-L1/L2 agent is an anti-PD-L1 antibody agent. In some embodiments, a PD-L1 antibody agent is atezolizumab, avelumab, CX-072, durvalumab, FAZ053, LY3300054, PD-L1 millamolecule, or derivatives thereof.

In some embodiments, a combination therapy comprises administering one or both of an anti-PD-1 therapy and an anti-PARP therapy so that a subject receives both, wherein either or both of the anti-PD-1 therapy and anti-PARP therapy are administered according to a regimen that includes at least one 2-12 week treatment cycle. Treatment duration shall be determined by a medical practitioner. In embodiments, treatment may continue until disease progression or toxicity. In some embodiments a treatment cycle is 2 weeks, 3 weeks, 4 weeks, 5 weeks, 6 weeks, 7 weeks, or 8 weeks. In some embodiments, an anti-PD-1 therapy and an anti-PARP therapy are administered in repeating cycles of 21 days. In some embodiments, an anti-PD-1 therapy is administered on day one of cycle one. In some embodiments, an anti-PD-1 therapy is administered on day one of a subsequent cycle. In some embodiments, an anti-PD-1 therapy is administered between one to three days before or after day one of a subsequent cycle.

In some embodiments, a treatment cycle is at least 2 weeks, at least 3 weeks, or at least 4 weeks. In some embodiments, a regimen includes at least 3, 4, 5, 6, or more treatment cycles. In some embodiments, a regimen includes at least 3 treatment cycles.

In some embodiments, an anti-PD-1 therapy is administered at a dose that is equivalent to 200 mg pembrolizumab or 2 mg/kg of pembrolizumab. In some embodiments, an anti-PD-1 therapy is administered intravenously. In related embodiments, an anti-PD-1 therapy is administered intravenously over about 30 minutes.

In some embodiments, an anti-PD-1 therapy is administered at a dose that is equivalent to 3 mg/kg or 240 mg of nivolumab. In some embodiments, an anti-PD-1 therapy is administered intravenously. In related embodiments, an anti-PD-1 therapy is administered intravenously over about 60 minutes.

In some embodiments, a combination therapy includes treatment such that a subject receives an increased dose of an agent that inhibits PARP if the subject's hemoglobin ≥9 g/dL, platelets≥100,000/μL, and neutrophils≥1500/μL for all labs performed during one or more cycles. In some embodiments, a dose of the agent that inhibits PARP is increased after two cycles. In some related embodiments, the increased dose of the agent that inhibits PARP is the FDA-approved dose. In some embodiments, the increased dose of the agent that inhibits PARP is the FDA-approved dose for use of the agent as a single agent. In some embodiments, the increased dose of the agent that inhibits PARP is equivalent to 300 mg of niraparib.

In some embodiments, a combination therapy includes treatment such that a subject receives a dose that is equivalent to 100 mg, 200 mg or 300 mg of niraparib daily.

In some embodiments, the subject to be treated with a combination therapy of the present disclosure has a cancer selected from: endometrial cancer, breast cancer, ovarian cancer, cervical cancer, fallopian tube cancer, primary peritoneal cancer, colon cancer, squamous cell carcinoma of the anogenital region, melanoma, renal cell carcinoma, lung cancer, non-small cell lung cancer, squamous cell carcinoma of the lung, stomach cancer, bladder cancer, gall bladder cancer, liver cancer, thyroid cancer, laryngeal cancer, salivary gland cancer, esophageal cancer, squamous cell carcinoma of the head and neck, prostate cancer, pancreatic cancer, mesothelioma, Merkel cell carcinoma, sarcoma, and a hematological cancer, such as multiple myeloma, B-cell lymphoma, T-cell lymphoma, Hodgkin's lymphoma/primary mediastinal B-cell lymphoma, and chronic myelogenous leukemia. Other cancers may include testicular cancer and cancers of the gastrointestinal tract (i.e. small intestine, rectal cancer). In some embodiments, a cancer for treatment is selected from: ovarian cancer, cervical cancer, fallopian tube cancer, primary peritoneal cancer, and triple negative breast cancer (TNBC). In some embodiments, a cancer for treatment with combination therapy of the present disclosure is recurrent. In some embodiments, a cancer for treatment with combination therapy of the present disclosure is platinum resistant. In some embodiments, a cancer for treatment with combination therapy of the present disclosure is platinum refractory.

In some embodiments, the subject is BRCA negative. In some embodiments, the subject is gBRCA negative, tBRCA negative, or sBRCA negative. In some embodiments, the subject is tBRCA negative. In some embodiments, the cancer for treatment is PD-L1 negative. In some embodiments, the subject is BRCA negative and the cancer for treatment with combination therapy is PD-L1 negative.

In some embodiments, a subject has previously been treated with one or more different cancer treatment modalities. In some embodiments, a subject has previously been treated with one or more of radiotherapy, chemotherapy or immunotherapy. In some embodiments, the subject has been treated with one, two, three, four, or five lines of prior therapy. In some embodiments, the subject has been treated with one or two lines of prior therapy. In some embodiments, the subject has been treated with one line of prior therapy. In some embodiments, the subject has been treated with two lines of prior therapy. In some embodiments, the prior therapy is cytotoxic therapy. In some embodiments, cytotoxic therapy includes chemotherapy. In some embodiments, wherein a subject has been treated with at least two lines of prior platinum-based therapy, the cancer progressed within six months of the last line of prior platinum-based therapy. In some embodiments, wherein a subject has been treated with at least two lines of prior platinum-based therapy, the cancer progressed within thirty days of the last line of prior platinum-based therapy.

In some embodiments, provided are methods of treating cancer, the methods including administering both an agent that inhibits PD-1 signaling and an agent that inhibits PARP to the subject.

In one aspect, the present disclosure provides a method of treating a recurrent cancer, the method comprising administering one or both of a PD-1 antibody agent and niraparib to a subject so that the subject receives treatment with both, wherein the cancer is a gynecological cancer or a breast cancer and wherein the treatment has been demonstrated to achieve clinical benefit in a percentage of patients, wherein the clinical benefit is or comprises stable disease ("SD"), a partial response ("PR") and/or a complete response ("CR"). In some embodiments, a recurrent cancer for treatment is selected from: ovarian cancer, cervical cancer, fallopian tube cancer, primary peritoneal cancer, and triple negative breast cancer (TNBC). In some embodiments, the recurrent cancer for treatment with combination therapy of the present disclosure is platinum resistant. In some embodiments, the recurrent cancer for treatment with combination therapy of the present disclosure is platinum refractory. In some embodiments, the subject for treatment with combination therapy of the present disclosure is BRCA negative. In some embodiments, the subject is gBRCA negative, tBRCA negative, or sBRCA negative. In some embodiments, the subject is tBRCA negative. In some embodiments, the recurrent cancer for treatment is PD-L1 negative. In some embodiments, the subject for treatment with combination therapy of the present disclosure is BRCA negative and the recurrent cancer for treatment with combination therapy is PD-L1 negative.

In some embodiments, a method of treating a recurrent cancer includes a step of administering a composition that delivers the PD-1 antibody agent to a subject who has received or will receive niraparib. In some embodiments, a step of administering comprises administering a composition that delivers the niraparib to a subject who has received or will receive the PD-1 antibody agent. In some embodiments, a clinical benefit has been demonstrated in at least 5%, 10%, 15%, 20%, 25%, 30%, 35%, 40%, 45%, or 50% of patients. In some embodiments, a clinical benefit has been demonstrated in at 10% of patients. In some embodiments, a clinical benefit is or comprises SD and at least 5%, 10%, 15%, 20%, 25%, 30%, 35%, 40%, 45%, or 50% of patients achieve SD. In some embodiments, a clinical benefit is or comprises SD and at least 10% of patients achieve SD. In some embodiments, a clinical benefit is or comprises PR and at least 5%, 10%, 15%, 20%, 25%, 30%, 35%, 40%, 45%, or 50% of patients achieve at least the PR. In some embodiments, a clinical benefit is or comprises PR and at 10% of patients achieve at least the PR. In some embodiments, a clinical benefit is or comprises CR at least 5%, 10%, 15%, 20%, 25%, 30%, 35%, 40%, 45%, or 50% of patients achieve at least the CR. In some embodiments, a clinical benefit is or comprises CR and at 10% of patients achieve at least the CR. In some embodiments, a clinical benefit has been demonstrated in at 20% of patients. In some embodiments, a clinical benefit is or comprises SD and at least 20% of patients achieve SD. In some embodiments, a clinical benefit is or comprises PR and at 20% of patients achieve at least the PR. In some embodiments, a clinical benefit is determined in accordance with Response Evaluation Criteria in Solid Tumors (RECIST).

In some embodiments, a method of treating a recurrent cancer includes administering both a PD-1 antibody and niraparib to the subject. In some embodiments, provided are methods of treating a recurrent gynecological cancer or breast cancer. In some embodiments, a treatment has been demonstrated to achieve overall response rate of at least 10%, 20%, 30%, 40%, 50% or 60%. In some embodiments, a treatment has been demonstrated to achieve overall response rate of at least 30%.

In one aspect, the present disclosure provides a method of treating a recurrent gynecological cancer or breast cancer including administering one or both of a programmed death-1 protein (PD-1) antibody agent and niraparib to a subject so that the subject receives treatment with both, wherein the treatment has been demonstrated to achieve overall response rate of at least 30%. In some embodiments, a response is assessed as at least a SD. In some embodiments, a response is assessed as a decrease in serum CA-125 concentration. In some embodiments, a recurrent cancer is selected from: ovarian cancer, fallopian tube cancer, primary peritoneal cancer or triple negative breast cancer. In some embodiments, a recurrent cancer is a high grade serous or a recurrent cancer with high grade predominantly serous histology. In some embodiments, a recurrent cancer is platinum resistant at the commencement of treatment. In some embodiments, a recurrent cancer is platinum refractory at the commencement of treatment. In some embodiments, a subject previously experienced a response to platinum-based therapy that lasted at least 6 months. In some embodiments, a recurrent cancer is ovarian cancer. In some embodiments, an ovarian cancer is high grade serous or an ovarian cancer with high grade predominantly serous histology. In some embodiments, an ovarian cancer is platinum resistant at the commencement of treatment. In some embodiments, an ovarian cancer is platinum refractory at the commencement of treatment. In some embodiments, a recurrent cancer is triple negative breast cancer.

In some embodiments, a subject to be treated by any of the methods of the disclosure has at least one mutation in BRCA1 and/or BRCA2. In some embodiments, a subject to be treated by any of the methods of the disclosure is characterized by an absence of a mutation in BRCA1 and BRCA2.

In some embodiments, the subject to be treated by any of the methods of the disclosure is human.

In some embodiments, the cancer is: i) a cancer associated with a high tumor mutation burden (TMB); ii) a cancer that is microsatellite stable (MSS); iii) a cancer that is characterized by microsatellite instability; iv) a cancer that has a high microsatellite instability status (MSI-H); v) a cancer that has a low microsatellite instability status (MSI-L); vi) a cancer associated with high TMB and MSI-H; vii) a cancer associated with high TMB and MSI-L or MSS; viii) a cancer that has a defective DNA mismatch repair system; ix) a cancer that has a defect in a DNA mismatch repair gene; x) a hypermutated cancer; xi) a cancer comprising a mutation in polymerase delta (POLD); xii) a cancer comprising a mutation in polymerase epsilon (POLE); xiii) a cancer that has homologous recombination repair deficiency/homologous repair deficiency ("HRD") or is characterized by a homologous recombination repair (HRR) gene mutation or deletion; xiv) adenocarcinoma, endometrial cancer, breast cancer, ovarian cancer, cervical cancer, fallopian tube cancer, testicular cancer, primary peritoneal cancer, colon cancer, colorectal cancer, small intestine cancer, squamous cell carcinoma of the anus, squamous cell carcinoma of the penis, squamous cell carcinoma of the cervix, squamous cell carcinoma of the vagina, squamous cell carcinoma of the vulva, soft tissue sarcoma, melanoma, renal cell carcinoma, lung cancer, non-small cell lung cancer, adenocarcinoma of the lung, squamous cell carcinoma of the lung, stomach cancer, bladder cancer, gall bladder cancer, liver cancer, thyroid cancer, laryngeal cancer, salivary gland cancer, esophageal cancer, head and neck cancer, squamous cell carcinoma of the head and neck, prostate cancer, pancreatic cancer, mesothelioma, Merkel cell carcinoma, sarcoma, glioblastoma, a hematological cancer, multiple myeloma, B-cell lymphoma, T-cell lymphoma, Hodgkin's lymphoma/primary mediastinal B-cell lymphoma, chronic myelogenous leukemia, acute myeloid leukemia, acute lymphoblastic leukemia, non-Hodgkin's lymphoma, neuroblastoma, a CNS tumor, diffuse intrinsic pontine glioma (DIPG), Ewing's sarcoma, embryonal rhabdomyosarcoma, osteosarcoma, or Wilms tumor; or xv) a cancer of xiv), wherein the cancer is MSS or MSI-L, is characterized by microsatellite instability, is MSI-H, has high TMB, has high TMB and is MSS or MSI-L, has high TMB and is MSI-H, has a defective DNA mismatch repair system, has a defect in a DNA mismatch repair gene, is a hypermutated cancer, is an HRD or HRR cancer, comprises a mutation in polymerase delta (POLD), or comprises a mutation in polymerase epsilon (POLE). In some embodiments, the cancer is melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, endometrial cancer, ovarian cancer, or Merkel cell carcinoma. In some embodiments, the cancer is non-small cell lung cancer, endometrial cancer, renal cell carcinoma, cervical cancer, stomach cancer, colorectal cancer, or triple negative breast cancer (TNBC). In some embodiments, the cancer is a cancer that has homologous recombination repair deficiency/homologous repair deficiency ("HRD") or is characterized by a homologous recombination repair (HRR) gene mutation or deletion. In some embodiments, the cancer is endometrial cancer, optionally MSI-H or MSS/MSI-L endometrial cancer. In some embodiments, the cancer is a MSI-H cancer comprising a mutation in POLE or POLD, optionally a MSI-H non-endometrial cancer comprising a mutation in POLE or POLD. In some embodiments, the cancer is breast cancer, optionally triple negative breast cancer (TNBC). In some embodiments, the cancer is ovarian cancer, optionally epithelial ovarian cancer. In some embodiments, the cancer is lung cancer, optionally non-small cell lung cancer. In some embodiments, the cancer is melanoma. In some embodiments, the cancer is colorectal cancer. In some embodiments, the cancer is squamous cell carcinoma of the anus, squamous cell carcinoma of the penis, squamous cell carcinoma of the cervix, squamous cell carcinoma of the vagina, or squamous cell carcinoma of the vulva. In some embodiments, the cancer is acute myeloid leukemia. In some embodiments, the cancer is acute lymphoblastic leukemia. In some embodiments, the cancer is non-Hodgkin's lymphoma. In some embodiments, the cancer is Hodgkin's lymphoma. In some embodiments, the cancer is neuroblastoma. In some embodiments, the cancer is a CNS tumor. In some embodiments, the cancer is diffuse intrinsic pontine glioma (DIPG). In some embodiments, the cancer is Ewing's sarcoma. In some embodiments, the cancer is embryonal rhabdomyosarcoma. In some embodiments, the cancer is osteosarcoma. In some embodiments, the cancer is Wilms tumor. In some embodiments, the cancer is soft tissue sarcoma. In some embodiments, the cancer is leiomyosarcoma.

DETAILED DESCRIPTION OF CERTAIN EMBODIMENTS

Definitions

Figure 1:
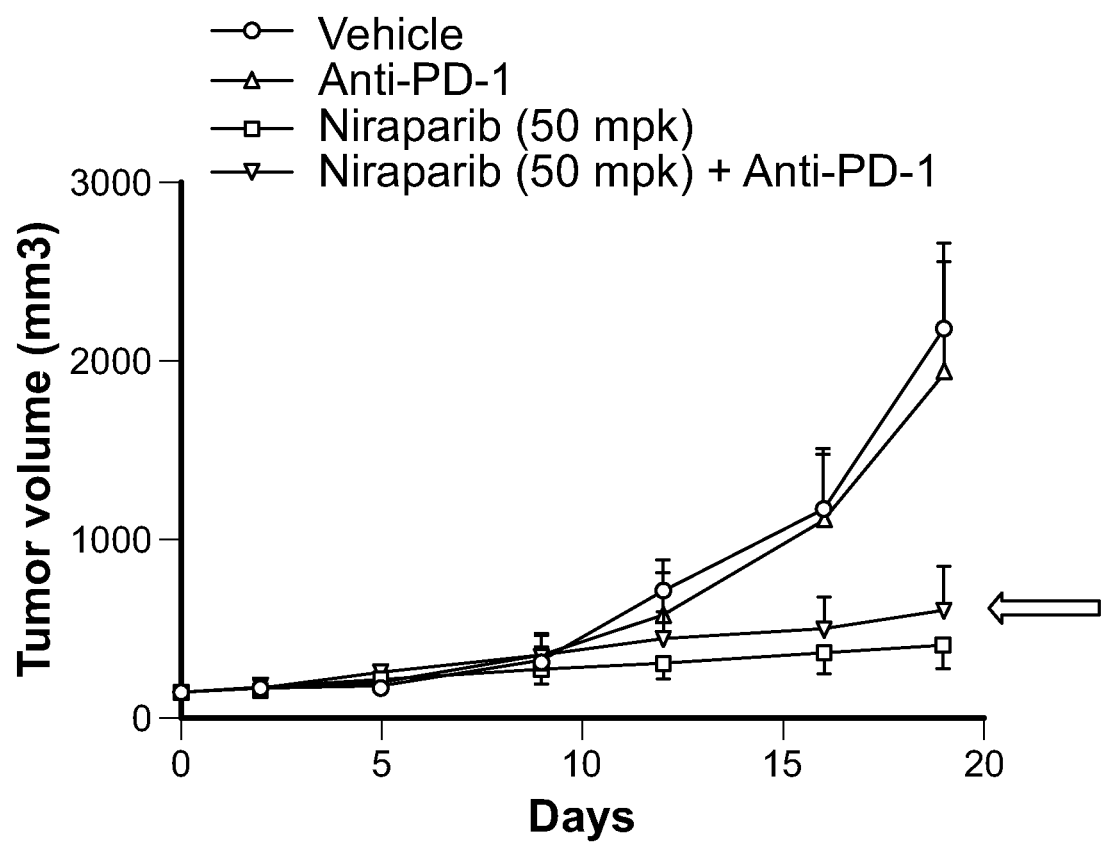
FIG. 1 depicts tumor growth curves of mice treated with vehicle, anti-PD-1 (5 mg/kg, BIW), niraparib (50 mg/kg, QD), or niraparib (50 mg/kg, QD) in combination with anti-PD-1 (5 mg/kg, BIW). The combination endpoint is noted by an arrow.

As used herein, the term "administration" typically refers to the administration of a composition to a subject or system. Those of ordinary skill in the art will be aware of a variety of routes that may, in appropriate circumstances, be utilized for administration to a subject, for example a subject (e.g., a human subject). For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e.g., intrahepatic), mucosal, nasal, oral, rectal, subcutaneous, sublingual, topical, tracheal (e.g., by intratracheal instillation), vaginal, vitreal, etc. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

As used herein, the terms "dosage form" or "unit dosage form" refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a regimen that has been determined to correlate with a desired or beneficial outcome when administered to a relevant population (i.e., with a therapeutic regimen). Those of ordinary skill in the art appreciate that the total amount of a therapeutic composition or agent administered to a particular subject is determined by one or more attending physicians and may involve administration of multiple dosage forms.

As used herein, the term "regimen" refers to a set of unit doses (typically more than one) that are administered individually to a subject, typically separated by one or more periods of time. In some embodiments, a given therapeutic agent is administered according to a regimen, which may involve one or more doses. In some embodiments, a regimen comprises a plurality of doses each of which is separated in time from other doses. In some embodiments, individual doses are separated from one another by a time period of the same length; in some embodiments, a regimen comprises a plurality of doses, wherein the doses are separated by time periods of different length. In some embodiments, a regimen comprises doses of the same amount. In some embodiments, a regimen comprises doses of different amounts. In some embodiments, a regimen comprises at least one dose, wherein the dose comprises one unit dose of the therapeutic agent. In some embodiments, a regimen comprises at least one dose, wherein the dose comprises two or more unit doses of the therapeutic agent. For example, a dose of 250 mg can be administered as a single 250 mg unit dose or as two 125 mg unit doses. In some embodiments, a regimen is correlated with or result in a desired or beneficial outcome when administered across a relevant population (i.e., is a therapeutic regimen).

As used herein, the phrase "FDA-approved dose" refers to a dose or dosing regimen of an agent that has been determined by the U.S. Food & Drug Administration ("FDA") to have demonstrated sufficient safety and effectiveness to meet FDA's requirements for marketing approval. In some embodiments, safety and effectiveness of a dose or dosing regimen of an agent has been evaluated by conducting one or more clinical trials. In some embodiments, FDA marketing approval has been issued for an agent for one or more indications. In some certain embodiments, FDA marketing approval has been issued for an agent for treatment of a cancer.

As used herein, the term "patient", "subject", or "test subject" refers to any organism to which compound or compounds described herein are administered in accordance with the present invention, e.g., for experimental, diagnostic, prophylactic, and/or therapeutic purposes. Exemplary subjects include animals (e.g., mammals such as mice, rats, rabbits, canines, felines, horses, cattle, pigs, deer, non-human primates, and humans; insects; worms; birds; reptiles; amphibians; etc.). In a preferred embodiment, a subject is a human. In some embodiments, a subject may be suffering from, and/or susceptible to a disease, disorder, and/or condition (e.g., cancer). In some embodiments, a patient is a human that has been diagnosed with a cancer. In some embodiments, a patient is a human possessing one or more female reproductive organs. In some embodiments, a patient is a human female (i.e., a woman) that has been diagnosed with a gynecological cancer or breast cancer (e.g., a cancer such as ovarian cancer, cancer of the fallopian tube(s), peritoneal cancer and breast cancer). As used herein, a "patient population" or "population of subjects" refers to a plurality of patients or subjects.

As used herein, a "therapeutically effective amount" refers to an amount of a therapeutic agent that produces the desired effect for which it is administered. In some embodiments, the term refers to an amount that is sufficient, when administered to a population suffering from or susceptible to a disease, disorder, and/or condition in accordance with a regimen, to treat the disease, disorder, and/or condition. In some embodiments, a therapeutically effective amount is one that reduces the incidence and/or severity of, and/or prevents or delays onset of, one or more symptoms of the disease, disorder, and/or condition. Those of ordinary skill in the art will appreciate that the term "therapeutically effective amount" does not in fact require for the disease, disorder, and/or condition to be resolved in a particular individual. Rather, a therapeutically effective amount may be an amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a regimen. In some embodiments, the combination of anti-PD-1 therapy and anti-PARP therapy is therapeutically effective. In some embodiments, the combination of an agent that inhibits PD-1 signaling and an agent that inhibits PARP is therapeutically effective.

As used herein, "CA-125" means cancer antigen 125. A CA-125 test is used to measure the amount of the protein CA-125 in the blood of a patient. A CA-125 test may be used to monitor certain cancers during and after treatment, including use to evaluate prolongation of progression free survival. In some cases, a CA-125 test may be used to look for early signs of ovarian cancer in women with a very high risk of the disease.

As used herein, a "chemotherapeutic agent" refers to a chemical agent that inhibits the proliferation, growth, lifespan and/or metastatic activity of cancer cells. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines (e.g., altretamine, triethylenemelamine, trietylenephosphoramide, triethiylenethiophosphoramide and trimethylolomelamine); acetogenins; delta-9-tetrahydrocannabinol (e.g., dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (e.g., cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifo sfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (e.g., T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); cyclophosphamide; thiotepa; taxanes, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; xeloda; ibandronate; topoisomerase inhibitor RFS 2000; difluoromethylornithine (DMFO); retinoids such as retinoic acid; capecitabine; pharmaceutically acceptable salts, acids or derivatives of any of the above; as well as combinations of two or more of the above such as CHOP, an abbreviation for a combined therapy of cyclophosphamide, doxorubicin, vincristine, and prednisone, and FOLFOX, an abbreviation for a treatment regimen with oxaliplatin (ELOXATIN™) combined with 5-FU and leucovovin.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGACE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

A "antimetabolite chemotherapeutic agent" is an agent which is structurally similar to a metabolite, but cannot be used by the body in a productive manner. Many antimetabolite chemotherapeutic agents interfere with the production of the nucleic acids, RNA and DNA. Examples of antimetabolite chemotherapeutic agents include gemcitabine (GEMZAR®), 5-fluorouracil (5-FU), capecitabine (XELODA™), 6-mercaptopurine, methotrexate, 6-thioguanine, pemetrexed, raltitrexed, arabinosylcytosine ARA-C cytarabine (CYTOSAR-U®), dacarbazine (DTIC-DOMED), azocytosine, deoxycytosine, pyridmidene, fludarabine (FLUDARA®), cladrabine, 2-deoxy-D-glucose, etc. In some embodiments, an antimetabolite chemotherapeutic agent is gemcitabine. Gemcitabine HC1 is sold by Eli Lilly under the trademark GEMZAR®.

As used herein, a "platinum-based chemotherapeutic agent" is a chemotherapeutic agent that comprises an organic compound which contains platinum as an integral part of the molecule. In some embodiments, a chemotherapeutic agent is a platinum agent. In some such embodiments, the platinum agent is selected from cisplatin, carboplatin, oxaliplatin, nedaplatin, triplatin tetranitrate, phenanthriplatin, picoplatin, or satraplatin.

As used herein, "BRCA mutation" or "mutation of BRCA" refers to a change or difference in the sequence of at least one copy of either or both of the BRCA1 or BRCA2 genes relative to an appropriate reference sequence (e.g., a wild type reference and/or a sequence that is present in non-cancerous cells in the subject). A mutation in the BRCA1/2 gene may result in a BRCA1/2 deficiency, which may include, for example a loss or reduction in the expression or function of the BRCA gene and/or encoded protein. Such mutations may also be referred to as "deleterious mutations" or may be suspected to be deleterious mutations. A BRCA mutation can be a "germline BRCA mutation,"

which indicates it was inherited from one or both parents. Germline mutations affect every cell in an organism and are passed on to offspring. A BRCA mutation can also be acquired during one's lifetime, i.e. spontaneously arising in any cell in the body ("soma") at any time during the patient's life, (i.e., non-inherited), which is referred to herein as a "sporadic BRCA mutation" or a "somatic BRCA mutation" interchangeably. Genetic tests are available, and known by those of skill in the art. For example, the BRACAnalysis CDx® kit is an in vitro diagnostic for detection and classification of germline BRCA1/2 variants. Using isolated genomic DNA, the BRACAnalysis CDx identifies mutations in the protein coding regions and intron/exon boundaries of the BRCA1 and BRCA2 genes. Single nucleotide variants and small insertions and deletions (indels) may be identified by polymerase chain reaction (PCR) and nucleotide sequencing. Large deletions and duplications in BRCA1 and BRCA2 may be detected using multiplex PCR. Indication of a "BRCA status" refers to, in at least some cases, whether a mutation is present in at least one copy of either BRCA1 or BRCA2. In some embodiments, indication of a BRCA status may refer to the mRNA expression level, methylation level or other epigenetic modification of either or both of BRCA1 and BRCA2. In some embodiments, a patient with a "positive BRCA status", "BRCA+" or "BRCA-mutant" refers to a patient from whom a sample has been determined to contain a mutation in BRCA1 and/or BRCA2. In some embodiments, a patient with a "positive BRCA status" refers to a patient from whom a sample has been determined to have a reduced expression of BRCA1 and/or BRCA2. In some embodiments, a patient with a "negative BRCA status", "BRCA−" "BRCA-wild type" refers to a patient from whom a sample has been determined to have wildtype BRCA1 and/or BRCA2 sequence (e.g., $BRCA^{wt}$). In some embodiments, BRCA status is determined for the presence of germline BRCA mutations (e.g., $gBRCA^{mut}$). In some embodiments, BRCA status is determined for the presence of circulating tumor DNA BRCA mutations (e.g., $ctBRCA^{mut}$) and/or cell-free DNA BRCA mutations (e.g., $cfBRCA^{mut}$). In some embodiments, BRCA mutation status is performed on a blood sample of a subject. In some embodiments, BRCA status is determined for the presence of somatic BRCA mutations ($sBRCA^{mut}$) and/or tumor BRCA mutations ($tBRCA^{mut}$). In some embodiments, BRCA status is determined for the presence of one or more of $sBRCA^{mut}$, $tBRCA^{mut}$, $gBRCA^{mut}$ $ctBRCA^{mut}$, and $cfBRCA^{mut}$.

As used herein, the term "progression free survival" means the time period for which a subject having a disease (e.g. cancer) survives, without a significant worsening of the disease state. Progression free survival may be assessed as a period of time in which there is no progression of tumor growth and/or wherein the disease status of a patient is not determined to be a progressive disease. In some embodiments, progression free survival of a subject having cancer is assessed by evaluating tumor (lesion) size, tumor (lesion) number, and/or metastasis.

The term "progression" of tumor growth or a "progressive disease" (PD) as used herein in reference to cancer status indicates an increase in the sum of the diameters of the target lesions (tumors). In some embodiments, progression of tumor growth refers to at least a 20% increase in the sum of diameters of target lesions, taking as reference the smallest sum on study (this includes the baseline sum if that is the smallest on study). In some embodiments, in addition to a relative increase of 20%, the sum of diameters of target lesions must also demonstrate an absolute increase of at least 5 mm. An appearance of one or more new lesions may also be factored into the determination of progression of tumor growth. Progression for the purposes of determining progression free survival may also be determined if at least one of the following criteria is met: 1) tumor assessment by CT/MRI unequivocally shows progressive disease according to RECIST 1.1 criteria; or 2) additional diagnostic tests (e.g. histology/cytology, ultrasound techniques, endoscopy, positron emission tomography) identify new lesions or determine existing lesions qualify for unequivocal progressive disease AND CA-125-progression according to Gynecologic Cancer Intergroup (GCIG)-criteria (see Rustin et al., Int J Gynecol Cancer 2011; 21: 419-423 which is incorporated herein in its entirety); 3) definitive clinical signs and symptoms of PD unrelated to non-malignant or iatrogenic causes ([i] intractable cancer-related pain; [ii] malignant bowel obstruction/worsening dysfunction; or [iii] unequivocal symptomatic worsening of ascites or pleural effusion) AND CA-125-progression according to GCIG-criteria.

As used herein, the term "partial response" or "PR" refers to a decrease in tumor progression in a subject as indicated by a decrease in the sum of the diameters of the target lesions, taking as reference the baseline sum diameters. In some embodiments, PR refers to at least a 30% decrease in the sum of diameters or target lesions, taking as reference the baseline sum diameters. Exemplary methods for evaluating partial response are identified by RECIST guidelines. See E. A. Eisenhauer, et al., "New response evaluation criteria in solid tumors: Revised RECIST guideline (version 1.1.)," *Eur. J. of Cancer*, 45: 228-247 (2009).

As used herein, "stabilization" of tumor growth or a "stable disease" (SD) refers to nNeither sufficient shrinkage to qualify for PR nor sufficient increase to qualify for PD. In some embodiments, stabilization refers to a less than 30%, 25%, 20%, 15%, 10% or 5% change (increase or decrease) in the sum of the diameters of the target lesions, taking as reference the baseline sum diameters. Exemplary methods for evaluating stabilization of tumor growth or a stable disease are identified by RECIST guidelines. See E. A. Eisenhauer, et al., "New response evaluation criteria in solid tumors: Revised RECIST guideline (version 1.1.)," *Eur. J. of Cancer*, 45: 228-247 (2009).

As used herein, the term "complete response" or "CR" is used to mean the disappearance of all or substantially all target lesions. In some embodiments, CR refers to an 80%, 85%, 90%, 91%, 92%, 93%, 94%, 95%, 96%, 97%, 98%, 99% or 100% decrease in the sum of the diameters of the target lesions (i.e. loss of lesions), taking as reference the baseline sum diameters. In some embodiments, CR indicates that less than 10%, 9%, 8%, 7%, 6%, 5%, 4%, 3%, 2%, 1% or less of the total lesion diameter remains after treatment. Exemplary methods for evaluating complete response are identified by RECIST guidelines. See E. A. Eisenhauer, et al., "New response evaluation criteria in solid tumors: Revised RECIST guideline (version 1.1.)," *Eur. J. of Cancer*, 45: 228-247 (2009).

As used herein, a "hazard ratio" is the expression of the hazard or chance of events occurring in the treatment arm as a ratio of the events occurring in the control arm. Hazard ratios may be determined by any method known in the art, for example, the Cox model, a regression method for survival data, which provides an estimate of the hazard ratio and its confidence interval. The hazard ratio is an estimate of the ratio of the hazard rate in the treated versus the control group. The hazard rate is the probability that if the event in question has not already occurred, it will occur in the next time interval, divided by the length of that interval. An assumption of proportional hazards regression is that the hazard ratio is constant over time.

As used herein, the term "treatment" (also "treat" or "treating") refers to any administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

As used herein, the term "polymorph" refers to a crystal structure of a compound. As used herein, the term "solvate" refers to a crystal form with either a stoichiometric or non-stoichiometric amount of solvent incorporated into the crystal structure. Similarly, the term "hydrate" refers to a crystal form with either a stoichiometric or non-stoichiometric amount of water incorporated into the crystal structure.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

As used herein, the term "pharmaceutical composition" refers to a composition in which an active agent is formulated together with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for oral administration, for example, drenches (aqueous or non-aqueous solutions or suspensions), tablets, e.g., those targeted for buccal, sublingual, and systemic absorption, boluses, powders, granules, pastes for application to the tongue. A pharmaceutical composition can also refer to a medicament.

As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Those skilled in the art are well familiar with antibody structure and sequence elements, recognize "variable" and "constant" regions in provided sequences, and understand that there may be some flexibility in definition of a "boundary" between such domains such that different presentations of the same antibody chain sequence may, for example, indicate such a boundary at a location that is shifted one or a few residues relative to a different presentation of the same antibody chain sequence. Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc., as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.]

As used herein, the term "antibody agent" refers to an agent that specifically binds to a particular antigen. In some embodiments, the term encompasses any polypeptide or polypeptide complex that includes immunoglobulin structural elements sufficient to confer specific binding. Exemplary antibody agents include, but are not limited to monoclonal antibodies or polyclonal antibodies. In some embodiments, an antibody agent may include one or more constant region sequences that are characteristic of mouse, rabbit, primate, or human antibodies. In some embodiments, an antibody agent may include one or more sequence elements are humanized, primatized, chimeric, etc., as is known in the art. In many embodiments, the term "antibody agent" is used to refer to one or more of the art-known or developed constructs or formats for utilizing antibody structural and functional features in alternative presentation. For example, embodiments, an antibody agent utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.]. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar (e.g., containing residues with related chemical properties at corresponding positions). For example, as is well known by those of ordinary skill in the art, certain amino acids are typically classified as similar to one another as "hydrophobic" or "hydrophilic" amino acids, and/or as having "polar" or "non-polar" side chains. Substitution of one amino acid for another of the same type may often be considered a "homologous" substitution.

As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent homology between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position; when a position in the first sequence is occupied by a similar nucleotide as the corresponding position in the second sequence, then the molecules are similar at that position. The percent homology between the two sequences is a function of the number of identical and similar positions shared by the sequences, taking into account the number of gaps, and the length of each gap, which needs to be introduced for optimal alignment of the two sequences. Representative algorithms and computer programs useful in determining the percent homology between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent homology between two nucleotide sequences can, alternatively, be determined for example using the GAP program in the GCG software package using an NWSgapdna.CMP matrix.

As used herein, the term "combination therapy" refers to a clinical intervention in which a subject is simultaneously exposed to two or more therapeutic regimens (e.g. two or more therapeutic agents). In some embodiments, the two or more therapeutic regimens may be administered simultaneously. In some embodiments, the two or more therapeutic regimens may be administered sequentially (e.g., a first regimen administered prior to administration of any doses of a second regimen). In some embodiments, the two or more therapeutic regimens are administered in overlapping dosing regimens. In some embodiments, administration of combination therapy may involve administration of one or more therapeutic agents or modalities to a subject receiving the other agent(s) or modality. In some embodiments, combination therapy does not necessarily require that individual agents be administered together in a single composition (or even necessarily at the same time). In some embodiments, two or more therapeutic agents or modalities of a combination therapy are administered to a subject separately, e.g., in separate compositions, via separate administration routes (e.g., one agent orally and another agent intravenously), and/or at different time points. In some embodiments, two or more therapeutic agents may be administered together in a combination composition, or even in a combination compound (e.g., as part of a single chemical complex or covalent entity), via the same administration route, and/or at the same time.

Cancers

Cancer is an abnormal growth of cells which tend to proliferate in an uncontrolled way and, in some cases, to metastasize (spread). Cancer is not one disease. It is a group of more than 100 different and distinctive diseases. Cancer can involve any tissue of the body and have many different forms in each body area. Most cancers are named for the type of cell or organ in which they start. A tumor can be cancerous or benign. A benign tumor means the tumor can grow but does not spread. A cancerous tumor is malignant, meaning it can grow and spread to other parts of the body. If a cancer spreads (metastasizes), the new tumor bears the same name as the original (primary) tumor. The frequency of a particular cancer may depend on gender. While skin cancer is the most common type of malignancy for both men and women, the second most common type in men is prostate cancer and in women, breast cancer.

The methods of the disclosure can be used to treat any type of cancer known in the art. Non-limiting examples of cancers to be treated by the methods of the present disclosure can include melanoma (e.g., metastatic malignant melanoma), renal cancer (e.g. clear cell carcinoma), prostate cancer (e.g. hormone refractory prostate adenocarcinoma), pancreatic adenocarcinoma, breast cancer, colon cancer, lung cancer (e.g. non-small cell lung cancer), esophageal cancer, squamous cell carcinoma, liver cancer, ovarian cancer, cervical cancer, thyroid cancer, glioblastoma, glioma, leukemia, lymphoma, mesothelioma, sarcoma and other neoplastic malignancies. Additionally, the invention includes refractory or recurrent malignancies whose growth may be inhibited using the methods of the invention. In some embodiments, a cancer to be treated by the methods of the present disclosure include, for example, carcinoma, squamous carcinoma (for example, cervical canal, eyelid, tunica conjunctiva, vagina, lung, oral cavity, skin, urinary bladder, head and neck, tongue, larynx, and gullet), and adenocarcinoma (for example, prostate, small intestine, endometrium, cervical canal, large intestine, lung, pancreas, gullet, intestinum rectum, uterus, stomach, mammary gland, and ovary). In some embodiments, a cancer to be treated by the methods of the present disclosure further include sarcomata (for example, myogenic sarcoma), leukosis, neuroma, melanoma, and lymphoma.

In some embodiments, a patient or population of patients to be treated with combination therapy of the present disclosure have a solid tumor. In some embodiments, a solid tumor is a melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, mesothelioma, sarcoma or Merkel cell carcinoma. In some embodiments, a patient or population of patients to be treated with combination therapy of the present disclosure have a hematological cancer. In some embodiments, the patient has a hematological cancer such as Diffuse large B cell lymphoma ("DLBCL"), Hodgkin's lymphoma ("HL"), Non-Hodgkin's lymphoma ("NHL"), Follicular lymphoma ("FL"), acute myeloid leukemia ("AML"), or Multiple myeloma ("MM").

In embodiments, a cancer is an advanced cancer. In some embodiments, a cancer is a stage II, stage III or stage IV cancer. In some embodiments, a cancer is a stage II cancer. In some embodiments, a cancer is a stage III cancer. In some embodiments, a cancer is a stage IV cancer.

In embodiments, a cancer is a metastatic cancer.

In embodiments, methods described herein are useful for reducing tumors or inhibiting the growth of tumor cells in a subject.

In embodiments, a cancer is a recurrent cancer.

Cancers that can be treated with methods described herein also include cancers associated with a high tumor mutation burden (TMB), cancers that microsatellite stable (MSS), cancers that are characterized by microsatellite instability, cancers that have a high microsatellite instability status (MSI-H), cancers that have low microsatellite instability status (MSI-L), cancers associated with high TMB and MSI-H, cancers associated with high TMB and MSI-L or MSS), cancers having a defective DNA mismatch repair system, cancers having a defect in a DNA mismatch repair gene, hypermutated cancers, cancers having homologous recombination repair deficiency/homologous repair deficiency ("HRD") or characterized by a homologous recombination repair (HRR) gene mutation or deletion, cancers comprising a mutation in polymerase delta (POLD), and cancers comprising a mutation in polymerase epsilon (POLE). In embodiments, a cancer is a cancer is characterized by a homologous recombination repair (HRR) gene mutation or deletion, a mutation in the DNA damage repair (DDR) pathway, BRCA deficiency, isocitrate dehydrogenase (IDH) mutation, and/or a chromosomal translocation. In embodiments, a cancer is a hypermutant cancer, a MSI-H cancer, a MSI-L cancer, or a MSS cancer. In embodiments, a cancer is characterized by one or more of these characteristics.

In some embodiments, a tumor to be treated is characterized by microsatellite instability. In some embodiments, a tumor is characterized by microsatellite instability high status (MSI-H). Microsatellite instability ("MSI") is or comprises a change that in the DNA of certain cells (such as tumor cells) in which the number of repeats of microsatellites (short, repeated sequences of DNA) is different than the number of repeats that was contained in the DNA from which it was inherited. About 15% of sporadic colorectal cancers (CRC) harbor widespread alterations in the length of microsatellite (MS) sequences, known as microsatellite instability (MSI) (Boland and Goel, 2010). Sporadic MSI CRC tumors display unique clinicopathological features including near-diploid karyotype, higher frequency in older populations and in females, and a better prognosis (de la Chapelle and Hampel, 2010; Popat et al., 2005). MSI is also present in other tumors, such as in endometrial cancer (EC) of the uterus, the most common gynecological malignancy (Duggan et al., 1994). The same reference Bethesda panel originally developed to screen an inherited genetic disorder (Lynch syndrome) (Umar et al., 2004) is currently applied to test MSI for CRCs and ECs. However, the genes frequently targeted by MSI in CRC genomes rarely harbor DNA slippage events in EC genomes (Gurin et al., 1999).

Microsatellite instability arises from a failure to repair replication-associated errors due to a defective DNA mismatch repair (MMR) system. This failure allows persistence of mismatch mutations all over the genome, but especially in regions of repetitive DNA known as microsatellites, leading to increased mutational load. It has been demonstrated that at least some tumors characterized by MSI-H have improved responses to certain PD-1 agents (Le et al., (2015) N. Engl. J. Med. 372(26):2509-2520; Westdorp et al., (2016) Cancer Immunol. Immunother. 65(10):1249-1259). In some embodiments, a cancer has a microsatellite instability of high microsatellite instability (e.g., MSI-H status). In some embodiments, a cancer has a microsatellite instability status of low microsatellite instability (e.g., MSI-Low). In some embodiments, a cancer has a microsatellite instability status of microsatellite stable (e.g., MSS status). In some embodiments microsatellite instability status is assessed by a next generation sequencing (NGS)-based assay, an immunohistochemistry (IHC)-based assay, and/or a PCR-based assay. In some embodiments, microsatellite instability is detected by NGS. In some embodiments, microsatellite instability is detected by IHC. In some embodiments, microsatellite instability is detected by PCR.

In embodiments, a patient has a MSI-L cancer.

In embodiments, a patient has a MSI-H cancer. In some embodiments, a patient has a MSI-H solid tumor. In embodiments, a MSI-H cancer is MSI-H endometrial cancer. In embodiments, a MSI-H cancer is a solid tumor. In embodiments, a MSI-H cancer is a metastatic tumor. In embodiments, a MSI-H cancer is endometrial cancer. In embodiments, a MSI-H cancer is a non-endometrial cancer. In embodiments, a MSI-H cancer is colorectal cancer.

In embodiments, a patient has a MSS cancer. In embodiments, a MSS cancer is MSS endometrial cancer.

In embodiments, a cancer is associated with a POLE (DNA polymerase epsilon) mutation (i.e., a cancer is a POLE-mutant cancer). In embodiments, a POLE mutation is a mutation in the exonuclease domain. In embodiments, a POLE mutation is a germline mutation. In embodiments, a POLE mutation is a sporadic mutation. In embodiments, a MSI cancer also is associated with a POLE mutation. In embodiments, a MSS cancer also is associated with a POLE mutation. In embodiments, a POLE mutation is identified using sequencing. In embodiments, a POLE-mutant cancer is endometrial cancer. In embodiments, a POLE-mutant cancer is colon cancer. In embodiments, a POLE-mutant cancer is pancreatic cancer, ovarian cancer, or cancer of the small intestine.

In embodiments, a cancer is associated with a POLD (DNA polymerase delta) mutation (i.e., a cancer is a POLD-mutant cancer). In embodiments, a POLD mutation is a mutation in the exonuclease domain. In embodiments, a POLD mutation is a somatic mutation. In embodiments, a POLD mutation is a germline mutation. In embodiments, a POLD-mutant cancer is identified using sequencing. In embodiments, a POLD-mutant cancer is endometrial cancer.

In embodiments, a POLD-mutant cancer is colorectal cancer. In embodiments, a POLD-mutant cancer is brain cancer.

In embodiments, a cancer has a defective DNA mismatch repair system (e.g., is a a mismatch repair deficient (MMRd) cancer). In embodiments, a cancer has a defect in a DNA mismatch repair gene. In some embodiments, a patient has a mismatch repair deficient cancer.

In embodiments, a MMRd cancer is colorectal cancer.

In embodiments, a cancer is a hypermutated cancer.

In embodiments, a cancer has homologous recombination repair deficiency/homologous repair deficiency ("HRD") or is characterized by a homologous recombination repair (HRR) gene mutation or deletion.

In embodiments, a cancer (e.g., a MMRd cancer) is characterized by a high tumor mutation burden (i.e., a cancer is a high TMB cancer). In some embodiments, the cancer is associated with high TMB and MSI-H. In some embodiments, the cancer is associated with high TMB and MSI-L or MSS. In some embodiments, the cancer is endometrial cancer associated with high TMB. In some related embodiments, the endometrial cancer is associated with high TMB and MSI-H. In some related embodiments, the endometrial cancer is associated with high TMB and MSI-L or MSS. In embodiments, a high TMB cancer is colorectal cancer. In embodiments, a high TMB cancer is lung cancer (e.g., small cell lung cancer (SCLC) or non-small cell lung cancer (NSCLC) such as squamous NSCLC or non-squamous NSCLC). In embodiments, a high TMB cancer is melanoma. In embodiments, a high TMB cancer is urothelial cancer.

In embodiments, a patient has a cancer with elevated expression of tumor-infiltrating lymphocytes (TILs), i.e., a patient has a high-TIL cancer. In embodiments, a high-TIL cancer is breast cancer (e.g., triple negative breast cancer (TNBC) or HER2-positive breast cancer). In embodiments, a high-TIL cancer is a metastatic cancer (e.g., a metastatic breast cancer).

Non-limiting examples of cancers to be treated by the methods of the present disclosure can include melanoma (e.g., metastatic malignant melanoma), renal cancer (e.g. clear cell carcinoma), prostate cancer (e.g. hormone refractory prostate adenocarcinoma), pancreatic adenocarcinoma, breast cancer, colon cancer, lung cancer (e.g. non-small cell lung cancer), esophageal cancer, head and neck cancer, squamous cell carcinoma, liver cancer, ovarian cancer, cervical cancer, thyroid cancer, glioblastoma, glioma, leukemia, lymphoma, mesothelioma, sarcoma and other neoplastic malignancies. Additionally, the invention includes refractory or recurrent malignancies whose growth may be inhibited using the methods of the invention. In some embodiments, a cancer to be treated by the methods of the present disclosure include, for example, carcinoma, squamous carcinoma (for example, cervical canal, eyelid, tunica conjunctiva, vagina, lung, oral cavity, skin, urinary bladder, head and neck, tongue, larynx, and gullet), and adenocarcinoma (for example, prostate, small intestine, endometrium, cervical canal, large intestine, lung, pancreas, gullet, intestinum rectum, uterus, stomach, mammary gland, and ovary). In some embodiments, a cancer to be treated by the methods of the present disclosure further include sarcomata (for example, myogenic sarcoma), leukosis, neuroma, melanoma, and lymphoma. In some embodiments, a cancer is a melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, or Merkel cell carcinoma (see, e.g., Bhatia et al, *Curr. Oncol. Rep.*, 13(6): 488-497 (2011)).

In embodiments, a cancer is acute myeloid leukemia ("AML"), acute lymphoblastic leukemia ("ALL"), adenocarcinoma, adenocarcinoma of the lung, adrenocortical carcinoma, anal cancer (e.g., squamous cell carcinoma of the anus), appendiceal cancer, B-cell derived leukemia, B-cell derived lymphoma, bladder cancer, brain cancer, breast cancer (e.g., triple negative breast cancer (TNBC) or non-triple negative breast cancer), cancer of the fallopian tube(s), cancer of the testes, cerebral cancer, cervical cancer (e.g., squamous cell carcinoma of the cervix), cholangiocarcinoma, choriocarcinoma, chronic myelogenous leukemia, a CNS tumor, colon adenocarcinoma, colon cancer or colorectal cancer (e.g., colon adenocarcinoma), diffuse intrinsic pontine glioma (DIPG), diffuse large B cell lymphoma ("DLBCL"), embryonal rhabdomyosarcoma (ERMS), endometrial cancer, epithelial cancer, esophageal cancer (e.g., squamous cell carcinoma of the esophagus), Ewing's sarcoma, eye cancer (e.g., uveal melanoma), follicular lymphoma ("FL"), gall bladder cancer, gastric cancer, gastrointestinal cancer, glioblastoma multiforme, glioma (e.g., lower grade glioma), head and neck cancer (e.g., squamous cell carcinoma of the head and neck (SCHNC)), a hematological cancer, hepatocellular cancer, Hodgkin's lymphoma (HL)/primary mediastinal B-cell lymphoma, kidney cancer (e.g., kidney clear cell cancer, kidney papillary cancer, or kidney chromophobe cancer), large B-cell lymphoma, laryngeal cancer, leukemia, liver cancer, lung cancer (e.g., non-small cell lung cancer (NSCLC), small cell lung cancer, lung adenocarcinoma, or squamous cell carcinoma of the lung), lymphoma, melanoma, Merkel cell carcinoma, mesothelioma, monocytic leukemia, multiple myeloma, myeloma, a neuroblastic-derived CNS tumor (e.g., neuroblastoma (NB)), non-Hodgkin's lymphoma (NHL), non-small cell lung cancer (NSCLC), oral cancer, osteosarcoma, ovarian cancer, ovarian carcinoma, pancreatic cancer, peritoneal cancer, pheocromocytoma, primary peritoneal cancer, prostate cancer, relapsed or refractory classic Hodgkin's Lymphoma (cHL), renal cancer (e.g., renal cell carcinoma), rectal cancer (rectum carcinoma), salivary gland cancer (e.g., a salivary gland tumor), sarcoma, skin cancer, small cell lung cancer, small intestine cancer, squamous cell carcinoma of the penis, soft tissue sarcoma, squamous cell carcinoma of the esophagus, squamous cell carcinoma of the head and neck (SCHNC), squamous cell carcinoma of the lung, stomach cancer, T-cell derived leukemia, T-cell derived lymphoma, testicular tumor, thymic cancer, a thymoma, thyroid cancer (thyroid carcinoma), uveal melanoma, urothelial cell carcinoma, uterine cancer (e.g., uterine endometrial cancer or uterine sarcoma such as uterine carcinosarcoma), vaginal cancer (e.g., squamous cell carcinoma of the vagina), vulvar cancer (e.g., squamous cell carcinoma of the vulva), or Wilms tumor.

In embodiments, a cancer is adenocarcinoma, endometrial cancer, breast cancer, ovarian cancer, cervical cancer, fallopian tube cancer, testicular cancer, primary peritoneal cancer, colon cancer, colorectal cancer, stomach cancer, small intestine cancer, squamous cell carcinoma of the anus, squamous cell carcinoma of the penis, squamous cell carcinoma of the cervix, squamous cell carcinoma of the vagina, squamous cell carcinoma of the vulva, soft tissue sarcoma, melanoma, renal cell carcinoma, lung cancer, non-small cell lung cancer, adenocarcinoma of the lung, squamous cell carcinoma of the lung, stomach cancer, bladder cancer, gall bladder cancer, liver cancer, thyroid cancer, laryngeal cancer, salivary gland cancer, esophageal cancer, head and neck cancer, squamous cell carcinoma of the head and neck, prostate cancer, pancreatic cancer, mesothelioma, Merkel cell carcinoma, sarcoma, glioblastoma, a hematological cancer, multiple myeloma, B-cell lymphoma, T-cell lymphoma, Hodgkin's lymphoma/primary mediastinal B-cell lymphoma, chronic myelogenous leukemia, acute myeloid leukemia, acute lymphoblastic leukemia, non-Hodgkin's lymphoma, neuroblastoma, a CNS tumor, diffuse intrinsic pontine glioma (DIPG), Ewing's sarcoma, embryonal rhabdomyosarcoma, osteosarcoma, or Wilms tumor. In embodiments, the cancer is MSS or MSI-L, is characterized by microsatellite instability, is MSI-H, has high TMB, has high TMB and is MSS or MSI-L, has high TMB and is MSI-H, has a defective DNA mismatch repair system, has a defect in a DNA mismatch repair gene, is a hypermutated cancer, is an HRD or HRR cancer, comprises a mutation in polymerase delta (POLD), or comprises a mutation in polymerase epsilon (POLE).

In embodiments, a cancer is large B-cell lymphoma, thymoma, acute myeloid leukemia, testicular tumor, lung adenocarcinoma, non-small cell lung cancer, kidney clear cell cancer, breast cancer, triple negative breast cancer (TNBC), non-triple negative breast cancer (non-TNBC), gastric cancer, lung squamous cell cancer, mesothelioma, pancreatic cancer, cervical cancer, head and neck cancer, melanoma, hepatocellular carcinoma, nasopharyngeal cancer, esophageal cancer, colon adenocarcinoma, colorectal cancer, rectum carcinoma, cholangiocarcinoma, uterine endometrial cancer, sarcoma, bladder cancer, thyroid carcinoma, kidney papillary cancer, glioblastoma multiforme, liver cancer, uterine carcinosarcoma, pheocromocytoma, lower grade glioma, kidney chromophobe, adrenocortical cancer, or uveal melanoma.

In other embodiments, a cancer is a head and neck cancer, a lung cancer (e.g., a non-small cell lung cancer (NSCLC)), a renal cancer, a bladder cancer, a melanoma, Merkel cell carcinoma, a cervical cancer, a vaginal cancer, a vulvar cancer, a uterine cancer, a endometrial cancer, an ovarian cancer, a fallopian tube cancer, a breast cancer, a prostate cancer, a salivary gland tumor, a thymoma, a adrenocortical carcinoma, a esophageal cancer, a gastric cancer, a colorectal cancer, an appendiceal cancer, a urothelial cell carcinoma, or a squamous cell carcinoma (e.g., of the lung; of the anogenital region including anus, penis, cervix, vagina, or vulva; or of the esophagus).

In some embodiments, a cancer for treatment in the context of the present disclosure is a melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, or Merkel cell carcinoma.

In embodiments a cancer is a lymphoma such as Hodgkin's disease, non-Hodgkin's Lymphoma, Multiple myeloma, Waldenstrom's macroglobulinemia, Heavy chain disease and Polycythemia vera.

In embodiments, a cancer is a squamous cell carcinoma. In embodiments, a cancer is squamous cell carcinoma of the lung. In embodiments, a cancer is squamous cell carcinoma of the esophagus. In embodiments, a cancer is squamous cell carcinoma of the anogenital region (e.g., of the anus, penis, cervix, vagina, or vulva). In embodiments, a cancer is head and neck squamous cell carcinoma (HNSCC).

In embodiments, a cancer is bladder cancer, breast cancer (e.g., triple negative breast cancer (TNBC)), cancer of the fallopian tube(s), cholagiocarcinoma, colon adenocarcinoma, endometrial cancer, esophageal cancer, Ewing's sarcoma, gastric cancer, kidney clear cell cancer, lung cancer (e.g., lung adenocarcinoma or lung squamous cell cancer), mesothelioma, ovarian cancer, pancreatic cancer, peritoneal cancer, prostate cancer, uterine endometrial cancer, or uveal melanoma. In embodiments, a cancer is ovarian cancer, cancer of the fallopian tube(s), or peritoneal cancer. In embodiments, a cancer is breast cancer (e.g., TNBC). In embodiments, a cancer is lung cancer (e.g., non-small cell lung cancer). In embodiments, a cancer is prostate cancer.

In embodiments, a cancer is a CNS or brain cancer such as neuroblastoma (NB), glioma, diffuse intrinsic pontine glioma (DIPG), pilocytic astrocytoma, astrocytoma, anaplastic astrocytoma, glioblastoma multiforme, medulloblastoma, craniopharyngioma, ependymoma, pinealoma, hemangioblastoma, acoustic neuroma, oligodendroglioma, meningioma, vestibular schwannoma, adenoma, metastatic brain tumor, meningioma, spinal tumor, or medulloblastoma. In embodiments, a cancer is a CNS tumor.

In other embodiments, a cancer is melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, or Merkel cell carcinoma (see, e.g., Bhatia et al., Curr. Oncol. Rep., 13(6): 488-497 (2011)).

In some embodiments, a patient or population of patients have a hematological cancer. In some embodiments, the patient has a hematological cancer such as diffuse large B cell lymphoma ("DLBCL"), Hodgkin's lymphoma ("HL"), Non-Hodgkin's lymphoma ("NHL"), follicular lymphoma ("FL"), acute myeloid leukemia ("AML"), acute lymphoblastic leukemia ("ALL"), or multiple myeloma ("MM"). In embodiments, a cancer is a blood-borne cancer such as acute lymphoblastic leukemia ("ALL"), acute lymphoblastic B-cell leukemia, acute lymphoblastic T-cell leukemia, acute myeloblastic leukemia ("AML"), acute lymphoblastic leukemia ("ALL"), acute promyelocytic leukemia ("APL"), acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia ("CML"), chronic lymphocytic leukemia ("CLL"), hairy cell leukemia and multiple myeloma; acute and chronic leukemias such as lymphoblastic, myelogenous, lymphocytic, and myelocytic leukemias. In embodiments, a hematological cancer is a lymphoma (e.g., Hodgkin's lymphoma (e.g., relapsed or refractory classic Hodgkin's Lymphoma (cHL), non-Hodgkin's lymphoma, diffuse large B-cell lymphoma, or precursor T-lymphoblastic lymphoma), lymphoepithelial carcinoma, or malignant histiocytosis.

In some embodiments, a patient or population of patients have a solid tumor. In embodiments, a cancer is a solid tumor such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, osteosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms tumor, cervical cancer, uterine cancer, testicular cancer, non small cell lung cancer (NSCLC), small cell lung carcinoma, bladder carcinoma, lung cancer, epithelial carcinoma, skin cancer, melanoma, neuroblastoma (NB), or retinoblastoma. In some embodiments, the tumor is an advanced stage solid tumor. In some embodiments, the tumor is a metastatic solid tumor. In some embodiments, the patient has a MSI-H solid tumor. In embodiments, a solid tumor is a MSS solid tumor. In embodiments, a solid tumor is a POLE-mutant solid tumor. In embodiments, a solid tumor is a MSS solid tumor. In embodiments, a solid tumor is a POLD-mutant solid tumor.

In some embodiments, a patient or population of patients to be treated by the methods of the present invention have or are susceptible to cancer, such as a head and neck cancer, a lung cancer (e.g., a non-small cell lung cancer (NSCLC)), a renal cancer, a bladder cancer, a melanoma, Merkel cell carcinoma, a cervical cancer, a vaginal cancer, a vulvar cancer, a uterine cancer, a endometrial cancer, an ovarian cancer, a fallopian tube cancer, a breast cancer, a prostate cancer, a salivary gland tumor, a thymoma, a adrenocortical carcinoma, a esophageal cancer, a gastric cancer, a colorectal cancer, an appendiceal cancer, a urothelial cell carcinoma, or a squamous cell carcinoma (e.g., of the lung; of the anogenital region including anus, penis, cervix, vagina, or vulva; or of the esophagus). In some embodiments, a patient or population of patients to be treated by the methods of the present invention have or are susceptible to lung cancer (e.g., NSCLC), renal cancer, melanoma, cervical cancer, colorectal cancer, or endometrial cancer (e.g., MSS endometrial cancer or MSI-H endometrial cancer).

In some embodiments, a patient or population of patients to be treated by the methods of the present invention have or are susceptible to non-small cell lung cancer (NSCLC), a hepatocellular cancer, a renal cancer, a melanoma, a cervical cancer, a colorectal cancer, a squamous cell carcinoma of the anogenital region (e.g., squamous cell carcinoma of the anus, penis, cervix, vagina, or vulva), a head and neck cancer, a triple negative breast cancer, an ovarian cancer or a endometrial cancer. In some embodiments, a patient has an advanced stage solid tumor, such as a non-small cell lung cancer (NSCLC), a hepatocellular cancer, a renal cancer, a melanoma, a cervical cancer, a colorectal cancer, a squamous cell carcinoma of the anogenital region (e.g., squamous cell carcinoma of the anus, penis, cervix, vagina, or vulva), a head and neck cancer, a triple negative breast cancer, an ovarian cancer or a endometrial cancer. In some embodiments, a patient has an advanced stage solid tumor with microsatellite instability.

In some embodiments, a cancer is a gynecologic cancer (i.e., a cancer of the female reproductive system such as ovarian cancer, fallopian tube cancer, cervical cancer, vaginal cancer, vulvar cancer, uterine cancer, or primary peritoneal cancer, or breast cancer). In some embodiments, cancers of the female reproductive system include, but are not limited to, ovarian cancer, cancer of the fallopian tube(s), peritoneal cancer, and breast cancer.

In embodiments, a cancer is ovarian cancer (e.g., serous or clear cell ovarian cancer). In embodiments, a cancer is fallopian tube cancer (e.g., serous or clear cell fallopian tube cancer). In embodiments, a cancer is primary peritoneal cancer (e.g., serous or clear cell primary peritoneal cancer).

In some embodiments, an ovarian cancer is an epithelial carcinoma. Epithelial carcinomas make up 85% to 90% of ovarian cancers. While historically considered to start on the surface of the ovary, new evidence suggests at least some ovarian cancer begins in special cells in a part of the fallopian tube. The fallopian tubes are small ducts that link a woman's ovaries to her uterus that are a part of a woman's reproductive system. In a normal female reproductive system, there are two fallopian tubes, one located on each side of the uterus. Cancer cells that begin in the fallopian tube may go to the surface of the ovary early on. The term 'ovarian cancer' is often used to describe epithelial cancers that begin in the ovary, in the fallopian tube, and from the lining of the abdominal cavity, call the peritoneum. In some embodiments, the cancer is or comprises a germ cell tumor. Germ cell tumors are a type of ovarian cancer develops in the egg-producing cells of the ovaries. In some embodiments, a cancer is or comprises a stromal tumor. Stromal tumors develop in the connective tissue cells that hold the ovaries together, which sometimes is the tissue that makes female hormones called estrogen. In some embodiments, a cancer is or comprises a granulosa cell tumor. Granulosa cell tumors may secrete estrogen resulting in unusual vaginal bleeding at the time of diagnosis. In some embodiments, a gynecologic cancer is associated with homologous recombination repair deficiency/homologous repair deficiency ("HRD"), a homologous recombination repair (HRR) gene mutation or deletion, and/or BRCA1/2 mutation(s). In some embodiments, a gynecologic cancer is platinum-sensitive. In some embodiments, a gynecologic cancer has responded to a platinum-based therapy. In some embodiments, a gynecologic cancer has developed resistance to a platinum-based therapy. In some embodiments, a gynecologic cancer has at one time shown a partial or complete response to platinum-based therapy (e.g., a partial or complete response to the last platinum-based therapy or to the penultimate platinum-based therapy). In some embodiments, a gynecologic cancer is now resistant to platinum-based therapy.

In embodiments, a cancer is a breast cancer. Usually breast cancer either begins in the cells of the milk producing glands, known as the lobules, or in the ducts. Less commonly breast cancer can begin in the stromal tissues. These include the fatty and fibrous connective tissues of the breast. Over time the breast cancer cells can invade nearby tissues such the underarm lymph nodes or the lungs in a process known as metastasis. The stage of a breast cancer, the size of the tumor and its rate of growth are all factors which determine the type of treatment that is offered. Treatment options include surgery to remove the tumor, drug treatment which includes chemotherapy and hormonal therapy, radiation therapy and immunotherapy. The prognosis and survival rate varies widely; the five year relative survival rates vary from 98% to 23% depending on the type of breast cancer that occurs. Breast cancer is the second most common cancer in the world with approximately 1.7 million new cases in 2012 and the fifth most common cause of death from cancer, with approximately 521,000 deaths. Of these cases, approximately 15% are triple-negative, which do not express the estrogen receptor, progesterone receptor (PR) or HER2. In some embodiments, triple negative breast cancer (TNBC) is characterized as breast cancer cells that are estrogen receptor expression negative (<1% of cells), progesterone receptor expression negative (<1% of cells), and HER2-negative.

In embodiments, a cancer is ER-positive breast cancer, ER-negative breast cancer, PR-positive breast cancer, PR-negative breast cancer, HER2-positive breast cancer, HER2-negative breast cancer, BRCA1/2-positive breast cancer, BRCA1/2-negative cancer, or triple negative breast cancer (TNBC). In embodiments, a cancer is triple negative breast cancer (TNBC). In some embodiments, a breast cancer is a metastatic breast cancer. In some embodiments, a breast cancer is an advanced breast cancer. In some embodiments, a cancer is a stage II, stage III or stage IV breast cancer. In some embodiments, a cancer is a stage IV breast cancer. In some embodiments, a breast cancer is a triple negative breast cancer. In embodiments, a breast cancer is a metastatic breast cancer. In embodiments, a breast cancer is a MSI-H breast cancer. In embodiments, a breast cancer is a MSS breast cancer. In embodiments, a breast cancer is a POLE-mutant breast cancer. In embodiments, a breast cancer is a POLD-mutant breast cancer. In embodiments, a breast cancer is a high TMB breast cancer. In embodiments, a breast cancer is associated with homologous recombination repair deficiency/homologous repair deficiency ("HRD") or is characterized by a homologous recombination repair (HRR) gene mutation or deletion.

In some embodiments, a patient or a population of patients to be treated by the methods of the present disclosure have or are susceptible to endometrial cancer ("EC"). Endometrial carcinoma is the most common cancer of the female genital, tract accounting for 10-20 per 100,000 person-years. The annual number of new cases of endometrial cancer (EC) is estimated at about 325 thousand worldwide. Further, EC is the most commonly occurring cancer in post-menopausal women. About 53% of endometrial cancer cases occur in developed countries. In 2015, approximately 55,000 cases of EC were diagnosed in the U.S. and no targeted therapies are currently approved for use in EC. There is a need for agents and regimens that improve survival for advanced and recurrent EC in 1 L and 2 L settings. Approximately 10,170 people are predicted to die from EC in the U.S. in 2016. The most common histologic form is endometrioid adenocarcinoma, representing about 75-80% of diagnosed cases. Other histologic forms include uterine papillary serous (less than 10%), clear cell 4%, mucinous 1%, squamous less than 1% and mixed about 10%.

From the pathogenetic point of view, EC falls into two different types, so-called types I and II. Type I tumors are low-grade and estrogen-related endometrioid carcinomas (EEC) while type II are non-endometrioid (NEEC) (mainly serous and clear cell) carcinomas. The World Health Organization has recently updated the pathologic classification of EC, recognizing nine different subtypes of EC, but EEC and serous carcinoma (SC) account for the vast majority of cases. EECs are estrogen-related carcinomas, which occur in perimenopausal patients, and are preceded by precursor lesions (endometrial hyperplasia/endometrioid intraepithelial neoplasia). Microscopically, lowgrade EEC (EEC 1-2) contains tubular glands, somewhat resembling the proliferative endometrium, with architectural complexity with fusion of the glands and cribriform pattern. High-grade EEC shows solid pattern of growth. In contrast, SC occurs in postmenopausal patients in absence of hyperestrogenism. At the microscope, SC shows thick, fibrotic or edematous papillae with prominent stratification of tumor cells, cellular budding, and anaplastic cells with large, eosinophilic cytoplasms. The vast majority of EEC are low grade tumors (grades 1 and 2), and are associated with good prognosis when they are restricted to the uterus. Grade 3 EEC (EEC3) is an aggressive tumor, with increased frequency of lymph node metastasis. SCs are very aggressive, unrelated to estrogen stimulation, mainly occurring in older women. EEC 3 and SC are considered high-grade tumors. SC and EEC3 have been compared using the surveillance, epidemiology and End Results (SEER) program data from 1988 to 2001. They represented 10% and 15% of EC respectively, but accounted for 39% and 27% of cancer death respectively. Endometrial cancers can also be classified into four molecular subgroups: (1) ultramutated/POLE-mutant; (2) hypermutated MSI+(e.g., MSI-H or MSI-L); (3) copy number low/microsatellite stable (MSS); and (4) copy number high/serous-like. Approximately 28% of cases are MSI-high. (Murali, *Lancet Oncol*. (2014). In some embodiments, a patient has a mismatch repair deficient subset of 2 L endometrial cancer. In embodiments, an endometrial cancer is metastatic endometrial cancer. In embodiments, a patient has a MSS endometrial cancer. In embodiments, a patient has a MSI-H endometrial cancer. In embodiments, an endometrial cancer is a MSI-L endometrial cancer. In embodiments, an endometrial cancer is a MSS endometrial cancer. In embodiments, an endometrial cancer is a POLE-mutant endometrial cancer (e.g., a MSI-H endometrial cancer comprising a POLE mutation). In embodiments, an endometrial cancer is a POLD-mutant endometrial cancer (e.g., MSI-H endometrial cancer comprising a POLD mutation). In embodiments, an endometrial cancer is a high TMB endometrial cancer. In embodiments, an endometrial cancer is associated with homologous recombination repair deficiency/homologous repair deficiency ("HRD") or is characterized by a homologous recombination repair (HRR) gene mutation or deletion.

In embodiments a cancer is a gonadal tumor.

In embodiments, a cancer is a non-endometrial cancer (e.g., a non-endometrial solid tumor). In embodiments, a non-endometrial cancer is an advanced cancer. In embodiments, a non-endometrial cancer is a metastatic cancer. In embodiments, a non-endometrial cancer is a MSI-H cancer. In embodiments, a non-endometrial cancer is a MSI-L endometrial cancer. In embodiments, a non-endometrial cancer is a MSS cancer. In embodiments, a non-endometrial cancer is a POLE-mutant cancer (e.g., a MSI-H non-endometrial cancer comprising a POLE mutation). In embodiments, a non-endometrial cancer is a POLD-mutant cancer (e.g., a MSI-H non-endometrial cancer comprising a POLD mutation). In embodiments, a non-endometrial cancer is a solid tumor (e.g., a MSS solid tumor, a MSI-H solid tumor, a POLD mutant solid tumor, or a POLE-mutant solid tumor). In embodiments, a non-endometrial cancer is a high TMB cancer. In embodiments, a non-endometrial cancer is associated with homologous recombination repair deficiency/ homologous repair deficiency ("HRD") or is characterized by a homologous recombination repair (HRR) gene mutation or deletion.

In embodiments, a cancer is a lung cancer. In embodiments, a lung cancer is a squamous cell carcinoma of the lung. In embodiments, a lung cancer is small cell lung cancer (SCLC). In embodiments, a lung cancer is non-small cell lung cancer (NSCLC) such as squamous NSCLC. In embodiments, a lung cancer is an ALK-translocated lung cancer (e.g., ALK-translocated NSCLC). In embodiments, a cancer is NSCLC with an identified ALK translocation. In embodiments, a lung cancer is an EGFR-mutant lung cancer (e.g., EGFR-mutant NSCLC). In embodiments, a cancer is NSCLC with an identified EGFR mutation.

In embodiments, a cancer is a colorectal (CRC) cancer (e.g., a solid tumor). In embodiments, a colorectal cancer is an advanced colorectal cancer. In embodiments, a colorectal cancer is a metastatic colorectal cancer. In embodiments, a colorectal cancer is a MSI-H colorectal cancer. In embodiments, a colorectal cancer is a MSS colorectal cancer. In embodiments, a colorectal cancer is a POLE-mutant colorectal cancer. In embodiments, a colorectal cancer is a POLD-mutant colorectal cancer. In embodiments, a colorectal cancer is a high TMB colorectal cancer.

In embodiments, a cancer is a melanoma. In embodiments, a melanoma is an advanced melanoma. In embodiments, a melanoma is a metastatic melanoma. In embodiments, a melanoma is a MSI-H melanoma. In embodiments, a melanoma is a MSS melanoma. In embodiments, a melanoma is a POLE-mutant melanoma. In embodiments, a melanoma is a POLD-mutant melanoma. In embodiments, a melanoma is a high TMB melanoma.

In embodiments, a cancer is a recurrent cancer (e.g., a recurrent gynecological cancer such as recurrent epithelial ovarian cancer, recurrent fallopian tube cancer, recurrent primary peritoneal cancer, or recurrent endometrial cancer).

Gynecological Cancers

In some embodiments, the methods of the disclosure can be used to treat a gynecological cancer, such as ovarian cancer, fallopian tube cancer, cervical cancer, vaginal cancer, vulvar cancer, uterine cancer, or primary peritoneal cancer. In some embodiments, an ovarian cancer is an epithelial carcinoma. Epithelial carcinomas make up 85% to 90% of ovarian cancers. While historically considered to start on the surface of the ovary, new evidence suggests at least some ovarian cancer begins in special cells in a part of the fallopian tube. The fallopian tubes are small ducts that link a woman's ovaries to her uterus that are a part of a woman's reproductive system. In a normal female reproductive system, there are two fallopian tubes, one located on each side of the uterus. Cancer cells that begin in the fallopian tube may go to the surface of the ovary early on. The term 'ovarian cancer' is often used to describe epithelial cancers that begin in the ovary, in the fallopian tube, and from the lining of the abdominal cavity, call the peritoneum. In some embodiments, the cancer is or comprises a germ cell tumor. Germ cell tumors are a type of ovarian cancer develops in the egg-producing cells of the ovaries. In some embodiments, a cancer is or comprises a stromal tumor. Stromal tumors develop in the connective tissue cells that hold the ovaries together, which sometimes is the tissue that makes female hormones called estrogen. In some embodiments, a cancer is or comprises a granulosa cell tumor. Granulosa cell tumors may secrete estrogen resulting in unusual vaginal bleeding at the time of diagnosis.

In some embodiments, a gynecological cancer (e.g., ovarian cancer) is metastatic. In some embodiments, a gynecological cancer (e.g., ovarian cancer) is an advanced gynecological cancer (e.g., ovarian cancer). In some embodiments, a cancer is a stage II, stage III or stage IV gynecological cancer (e.g., ovarian cancer).

The expected incidence of epithelial ovarian cancer in women in the United States in 2012 is approximately 22,280 (15,500 deaths) and in Europe in 2012 was estimated at 65,538 patient cases (42,704 deaths). At diagnosis, most women present with advanced disease, which accounts for the high mortality rate. Standard therapy for advanced ovarian cancer typically consists of surgical debulking and a chemotherapy regimen. Initial chemotherapy consists of either taxane or platinum chemotherapy, or a combination thereof. While patients have been reported to respond initially to front line therapy, many of those patients who initially respond eventually relapse within 1 to 3 years. After relapse, patients respond moderately or poorly to subsequent chemotherapy. Additionally, intolerance to platinum agents is a clinical concern, as the risk of cumulative toxicities increases over the course of continued treatments. There is a significant unmet need due to the high recurrence rate, despite an initially high response rate. Attempts to improve the standard two-drug chemotherapy (carboplatin and paclitaxel) by adding a third cytotoxic drug (topotecan, gemcitabine, or doxil) have failed (du Bois et al, 2006 and Pfisterer et al, 2006).

Breast Cancer

In some embodiments, the methods of the disclosure can be used to treat breast cancer. Usually breast cancer either begins in the cells of the milk producing glands, known as the lobules, or in the ducts. Less commonly breast cancer can begin in the stromal tissues. These include the fatty and fibrous connective tissues of the breast. Over time the breast cancer cells can invade nearby tissues such the underarm lymph nodes or the lungs in a process known as metastasis. The stage of a breast cancer, the size of the tumor and its rate of growth are all factors which determine the type of treatment that is offered. Treatment options include surgery to remove the tumor, drug treatment which includes chemotherapy and hormonal therapy, radiation therapy and immunotherapy. The prognosis and survival rate varies widely; the five year relative survival rates vary from 98% to 23% depending on the type of breast cancer that occurs. Breast cancer is the second most common cancer in the world with approximately 1.7 million new cases in 2012 and the fifth most common cause of death from cancer, with approximately 521,000 deaths. Of these cases, approximately 15% are triple-negative, which do not express the estrogen receptor, progesterone receptor (PR) or HER2. In some embodiments, triple negative breast cancer (TNBC) is characterized as breast cancer cells that are estrogen receptor expression negative (<1% of cells), progesterone receptor expression negative (<1% of cells), and HER2-negative.

In some embodiments, a breast cancer is a metastatic breast cancer. In some embodiments, a breast cancer is an advanced breast cancer. In some embodiments, a cancer is a stage II, stage III or stage IV breast cancer. In some embodiments, a cancer is a stage IV breast cancer. In some embodiments, a breast cancer is a triple negative breast cancer.

Recurrent Cancers

In some embodiments, a patient has a recurrent cancer that has been previously treated with chemotherapy. In some embodiments, a chemotherapeutic agent is a platinum agent. In some such embodiments, the platinum agent is selected from cisplatin, carboplatin, oxaliplatin, nedaplatin, triplatin tetranitrate, phenanthriplatin, picoplatin, or satraplatin.

In some embodiments, a cancer is characterized as "platinum resistant." In some embodiments, a platinum resistant cancer is a cancer that has progressed within 3 years (e.g., within 30 months, within 24 months, within 18 months, within 12 months, within 6 months) after completing a platinum-based chemotherapy regimen. In some embodiments, a platinum resistant cancer is a cancer that has progressed while the patient is receiving platinum-based chemotherapy (i.e. the patient is "platinum refractory"). In some embodiments, a cancer is characterized as "platinum refractory."

In some embodiments, a patient with a recurrent cancer who has been previously treated with platinum-based chemotherapy has experienced a response lasting at least 6 months (e.g., at least 6 months, 8 months, 10 months, 12 months, 14 months, 16 months, 18 months, 24 months) to platinum-based therapy. In some embodiments, a patient has experienced a response lasting at least 6 months to first-line platinum-based therapy but currently considered platinum-resistant. In some embodiments, a patient with a recurrent cancer has been treated with 1, 2, 3, 4, or 5 lines of prior chemotherapy. In some embodiments, a patient has a recurrent high-grade serous ovarian, fallopian tube, or primary peritoneal cancer and has been previously treated with chemotherapy for advanced/metastatic disease and has experienced a response lasting at least 6 months to first-line platinum-based therapy but currently considered platinum-resistant.

In some embodiments, a patient with cancer has received adjuvant therapy. In some embodiments, an adjuvant therapy is an additional cancer treatment that is given after a primary treatment to lower the risk that the cancer will come back. Adjuvant therapy may include chemotherapy, radiation therapy, hormone therapy, targeted therapy or biological therapy. In some embodiments, a patient with cancer has been treated with at least 1 prior regimen for advanced/metastatic disease has relapsed/progressed while on or within 1 month from completion of adjuvant chemotherapy. In some embodiments, a patient with a recurrent cancer has been treated with 1, 2, 3, 4, or 5 lines of prior chemotherapy. In some embodiments, a patient has a triple-negative breast cancer (TNBC) has been treated with at least 1 prior regimen for advanced/metastatic disease has relapsed/progressed while on or within 1 month from completion of adjuvant chemotherapy.

In some embodiments, patients have progression of disease within six months of the last (most recent) line of platinum-based therapy and may be referred to as being "platinum resistant." In some embodiments, patients have progression of disease within 30 days of the last (most recent) line of platinum-based therapy and may be referred to as being "platinum refractory." In some such embodiments, the patient experienced a response lasting at least 6 months to first-line platinum-based therapy.

BRCA

In some embodiments, a cancer is characterized by deficiencies in DNA repair such as BRCA mutations. BRCA 1 and 2 were initially identified as tumor suppressor genes that were associated with increased incidence of certain malignancies when defective. In some embodiments, a cancer has one or more of germline BRCA mutation, sporadic BRCA mutation and BRCA promoter hypermethylation. In some embodiments, a cancer has a combination of two or more of germline BRCA mutation, sporadic BRCA mutation and BRCA promoter hypermethylation. Germline mutations of BRCA-1 and BRCA-2 genes are found in a majority of patients with an inherited breast or ovarian cancer. Inactivation of BRCA-1 or BRCA-2 gene by other mechanisms, including somatic BRCA-1/2 mutations and/or gene silencing by promoter hypermethylation, occurs in a significant portion of several sporadic cancers. In particular, for ovarian cancer, somatic BRCA-1 or BRCA-2 mutations are found in 10%-15% of all epithelial ovarian carcinomas (EOCs), and strongly reduced expression of BRCA-1 has been observed in a significant portion of sporadic ovarian cancers.

BRCA plays a key role in DNA repair, including homologous recombination. It is estimated that over half of high grade serous ovarian cancer suffered from defects in DNA repair. Tumor cells with BRCA deficiency may provide an opportunity for therapeutic intervention with agents that inhibit DNA repair pathways and exploit synthetic lethality mechanisms of cancer treatment.

In some embodiments, a subject to be treated by methods of the present disclosure is characterized by a "positive BRCA status", "BRCA+" or "BRCA-mutant." In some embodiments, a patient with a "positive BRCA status" refers to a patient from whom a sample has been determined to have a reduced expression of BRCA1 and/or BRCA2.

In some embodiments, a subject to be treated by methods of the present disclosure is characterized by a "negative BRCA status", "BRCA-" or "BRCA-wild type." In some embodiments a negative BRCA status refers to a patient from whom a sample has been determined to have wildtype BRCA1 and/or BRCA2 sequence (e.g., BRCA$^{wt}$).

Homologous Recombination Deficiency

In some aspects and in some embodiments, the status of homologous recombination deficiency (HRD) may be assessed in a subject or in a cancer of a subject to be treated by methods of the present disclosure. In some embodiments, HRD may be evaluated using the following chromosomal markers: LOH (loss of heterozygosity), LST (large-scale state transitions), and TAI (telomeric allelic imbalance).

Homologous recombination is an essential pathway for DNA repair, particularly in the context of repairing double-stranded DNA breaks. A deficiency in homologous recombination may result in the utilization of other pathways for DNA repair, such as non-homologous end-joining (NHEJ). However, NHEJ is more error-prone compared to homologous recombination in DNA repair, resulting in a greater number of mutations and thus increasing the risk of chromosomal instability and tumor transformation.

In some embodiments of the disclosure, the patient may be HRD-negative. As will be understood by one of skill in the art, a subject having an HRD-negative status refers to a subject having no homologous recombination deficiency according to an assay of a biological sample from the subject. In some embodiments of the disclosure, the patient may be HRD-positive. As will be understood by one of skill in the art, a subject having an HRD-positive status refers to a subject having deficient homologous recombination according to an assay of a biological sample from the subject.

PD-L1 Negative Cancer

In some aspects and in some embodiments of the disclosure, the cancer is PD-L1 negative. As will be understood by one of skill in the art, a subject having a cancer that is PD-L1 negative means that the expression of PD-L1 is reduced or absent in a cancer cell in the subject. PD-L1 expression may be measured by any method known to one of skill in the art. For example, PD-L1 expression may be measured by immunohistochemistry (IHC) using the PD-L1 IHC 22C3 pharmDx (Agilent, Carpinteria, Calif., USA). In some embodiments, a cancer is PD-L1 negative if expression in cancer cells compared to immune cells by IHC is 1% or less.

Role of Poly(ADP-Ribose) Polymerases (PARPs)

Poly(ADP-ribose) polymerases (PARPs) are a family of enzymes that cleave NAD+, releasing nicotinamide, and successively add ADP-ribose units to form ADP-ribose polymers. Accordingly, activation of PARP enzymes can lead to depletion of cellular NAD+ levels (e.g., PARPs as NAD+ consumers) and mediates cellular signaling through ADP-ribosylation of downstream targets. PARP-1 is a zinc-finger DNA-binding enzyme that is activated by binding to DNA double or single strand breaks. It was known that anti-alkylating agents could deplete the NAD+ content of tumor cells, and the discovery of PARPs explained this phenomenon. (Parp Inhibitors and Cancer Therapy. Curtin N. in *Poly ADP Ribosylation*. ed. Alexander Burke, Lands Bioscience and Springer Bioscience, 2006: 218-233). Anti-alkylating agents induce DNA strand breaks, which activates of PARP-1, which is part of the DNA repair pathway. Poly ADP-ribosylation of nuclear proteins by PARP-1 converts DNA damage into intracellular signals that can either activate DNA repair (e.g. by the base excision repair (BER) pathway); or trigger cell death in the presence of DNA damage that is too extensive and cannot be efficiently repaired.

PARP-2 contains a catalytic domain and is capable of catalyzing a poly(ADP-ribosyl)ation reaction. PARP-2 displays auto-modification properties similar to PARP-1. The protein is localized in the nucleus in vivo and may account for the residual poly(ADP-ribose) synthesis observed in PARP-1-deficient cells, treated with alkylating agents or hydrogen peroxide. Some agents that inhibit PARP (e.g., agents primarily aimed at inhibiting PARP-1) may also inhibit PARP-2 (e.g., niraparib).

The role of PARP enzymes in DNA damage response (e.g. repair of DNA in response to genotoxic stress) has led to the compelling suggestion that PARP inhibitors may be useful anti-cancer agents. PARP inhibitors may be particularly effective in treating cancers resulting from germ line or sporadic deficiency in the homologous recombination DNA repair pathway, such as BRCA-1 and/or BRCA-2 deficient cancers.

Pre-clinical ex vivo and in vivo experiments suggest that PARP inhibitors are selectively cytotoxic for tumors with homozygous inactivation of BRCA-1 and/or BRCA-2 genes, which are known to be important in the homologous recombination (HR) DNA repair pathway. The biological basis for the use of PARP inhibitors as single agents in cancers with defects in BRCA-1 and/or BRCA-2 is the requirement of PARP-1 and PARP-2 for base excision repair (BER) of the damaged DNA. Upon formation of single-strand DNA breaks, PARP-1 and PARP-2 bind at sites of lesions, become activated, and catalyze the addition of long polymers of ADP-ribose (PAR chains) on several proteins associated with chromatin, including histones, PARP itself, and various DNA repair proteins. This results in chromatin relaxation and fast recruitment of DNA repair factors that access and repair DNA breaks. Normal cells repair up to 10,000 DNA defects daily and single strand breaks are the most common form of DNA damage. Cells with defects in the BER pathway enter S phase with unrepaired single strand breaks. Pre-existing single strand breaks are converted to double strand breaks as the replication machinery passes through the break. Double strand breaks present during S phase are preferentially repaired by the error-free HR pathway. Cells with inactivation of genes required for HR, such as BRCA-1 and/or BRCA-2, accumulate stalled replication forks during S phase and may use error-prone non-homologous end joining (NHEJ) to repair damaged DNA. Both the inability to complete S phase (because of stalled replication forks) and error-prone repair by NHEJ, are thought to contribute to cell death.

Without wishing to be bound by theory, it is hypothesized that treatment with PARP inhibitors may selectively kill a subset of cancer cells with deficiencies in DNA repair pathways (e.g., inactivation of BRCA-1 and/or BRCA-2). For example, a tumor arising in a patient with a germline BRCA mutation has a defective homologous recombination DNA repair pathway and would be increasingly dependent on BER, a pathway blocked by PARP inhibitors, for maintenance of genomic integrity. This concept of inducing death by use of PARP inhibitors to block one DNA repair pathway in tumors with pre-existing deficiencies in a complementary DNA repair pathways is called synthetic lethality.

The therapeutic potential of PARP inhibitors is further expanded by the observation that PARP inhibitors not only have monotherapy activity in HR-deficient tumors, but are also effective in preclinical models in combination with other agents such as cisplatin, carboplatin, alkylating and methylating agents, radiation therapy, and topoisomerase I inhibitors. In contrast to the rationale for monotherapy in which PARP inhibition alone is sufficient for cell death in HR-deficient cancers (due to endogenous DNA damage), PARP is required for repair of DNA damage induced by standard cytotoxic chemotherapy. In some cases, the specific role of PARP is not known, but PARP is known to be required to release trapped topoisomerase I/irinotecan complexes from DNA. Temozolomide-induced DNA damage is repaired by the BER pathway, which requires PARP to recruit repair proteins. Combination therapies that enhance or synergize the cancer therapy without significantly increasing toxicity would provide substantial benefit to cancer patients, including ovarian cancer patients.

PARP Inhibitors

Without wishing to be bound by theory, treatment with PARP inhibitors (e.g., PARP-1/2 inhibitors) may selectively kill a subset of cancer cell types by exploiting their deficiencies in DNA repair. Human cancers exhibit genomic instability and an increased mutation rate due to underlying defects in DNA repair. These deficiencies render cancer cells more dependent on the remaining DNA repair pathways and targeting these pathways is expected to have a much greater impact on the survival of the tumor cells than on normal cells.

In some embodiments, a PARP inhibitor is ABT-767, AZD 2461, BGB-290, BGP 15, CEP 8983, CEP 9722, DR 2313, E7016, E7449, fluzoparib (SHR 3162), IMP 4297, INO1001, JPI 289, JPI 547, monoclonal antibody B3-LysPE40 conjugate, MP 124, niraparib (ZEJULA) (MK-4827), NU 1025, NU 1064, NU 1076, NU1085, olaparib (AZD2281), ON02231, PD 128763, R 503, R554, rucaparib (RUBRACA) (AG-014699, PF-01367338), SBP 101, SC 101914, Simmiparib, talazoparib (BMN-673), veliparib (ABT-888), WW 46, 2-(4-(Trifluoromethyl)phenyl)-7,8-dihydro-5H-thiopyrano[4,3-d]pyrimidin-4-ol, including any salts or derivatives thereof. In some embodiments, an agent that inhibits PARP is a small molecule. In some embodiments, an agent that inhibits PARP is an antibody agent. In some embodiments, an agent that inhibits PARP is a combination of agents. In some certain embodiments, a PARP inhibitor is niraparib, olaparib, rucaparib, talazoparib, veliparib, or any combination thereof. In some embodiments, a PARP inhibitor can be prepared as a pharmaceutically acceptable salt. One of skill in the art will appreciate that such salt forms can exist as solvated or hydrated polymorphic forms.

Target engagement has also been demonstrated by measuring PARP activity in tumor homogenates from tumor xenograft studies. Niraparib has been shown to induce cell cycle arrest, particularly arrest in the G2/M phase of the cell cycle. Accordingly, in some embodiments, the present invention provides a method of inducing cell cycle arrest of a tumor cell, the method comprising administering niraparib to a patient in need thereof. In some embodiments, the present invention provides a method of inducing arrest of the G2/M phase of the cell cycle of a tumor cell, the method comprising administering niraparib to a patient in need thereof. In some embodiments, the present invention provides a method of inducing arrest in the G2/M phase of the cell cycle of BRCA-1 and/or BRCA-2-deficient cells, the method comprising administering niraparib to a patient in need thereof.

At diagnosis of ovarian cancer, most women present with advanced disease, which accounts for the high mortality rate. Patients with stage 2, 3 or 4 disease will undergo tumor reductive surgery if the disease is potentially resectable and may undergo subsequent chemotherapy for 4-8 cycles. Initial chemotherapy may consist of either IV chemotherapy or a combination of IV and intraperitoneal (IP) chemotherapy. IV chemotherapy usually consists of a taxane (paclitaxel or docetaxel) and a platinum (cisplatin or carboplatin).

Approximately 75% of patients respond to front line therapy and are considered platinum sensitive, standardly defined as a minimum duration of 6 months following treatment with no relapse or disease progression. However, up to 70% of patients eventually relapse within 1 to 3 years. Attempts to improve the standard platinum based two-drug chemotherapy by adding a third cytotoxic drug have failed to affect either progression-free survival or overall survival and resulted in an increase in toxic effects (du Bois et al, 2006 and Pfisterer, 2006 et al). There is a high unmet need due to the high recurrence rate, even after an initially high response rate.

Niraparib

Niraparib, (3S)-3-[4-{7-(aminocarbonyl)-2H-indazol-2-yl}phenyl]piperidine, is an orally available, potent, poly (adenosine diphosphate [ADP]-ribose) polymerase (PARP)-1 and -2 inhibitor. See WO 2008/084261 (published on Jul. 17, 2008) and WO 2009/087381 (published Jul. 16, 2009), the entirety of each of which is hereby incorporated by reference. Niraparib can be prepared according to Scheme 1 of WO 2008/084261. As used herein, the term "niraparib" means any of the free base compound ((3S)-3-[4-{7-(aminocarbonyl)-2H-indazol-2-yl}phenyl]piperidine), a salt form, including pharmaceutically acceptable salts, of (3S)-3-[4-{7-(aminocarbonyl)-2H-indazol-2-yl}phenyl]piperidine (e.g., (3S)-3-[4-{7-(aminocarbonyl)-2H-indazol-2-yl}phenyl]piperidine tosylate), or a solvated or hydrated form thereof (e.g., (3S)-3-[4-{7-(aminocarbonyl)-2H-indazol-2-yl}phenyl]piperidine tosylate monohydrate). In some embodiments, such forms may be individually referred to as "niraparib free base", "niraparib tosylate" and "niraparib tosylate monohydrate", respectively. Unless otherwise specified, the term "niraparib" includes all forms of the compound (3S)-3-[4-{7-(aminocarbonyl)-2H-indazol-2-yl}phenyl]piperidine.

In some embodiments, niraparib can be prepared as a pharmaceutically acceptable salt. One of skill in the art will appreciate that such salt forms can exist as solvated or hydrated polymorphic forms. In some embodiments, niraparib is prepared in the form of a hydrate.

In certain embodiments, niraparib is prepared in the form of a tosylate salt. In some embodiments, niraparib is prepared in the form of a tosylate monohydrate.

The crystalline tosylate monohydrate salt of niraparib is being developed as a monotherapy agent for tumors with defects in the homologous recombination (HR) deoxyribonucleic acid (DNA) repair pathway and as a sensitizing agent in combination with cytotoxic agents and radiotherapy.

Niraparib is a potent and selective PARP-1 and PARP-2 inhibitor with inhibitory concentration at 50% of control ($IC_{50}$)=3.8 and 2.1 nM, respectively, and is at least 100-fold selective over other PARP-family members. Niraparib inhibits PARP activity, stimulated as a result of DNA damage caused by addition of hydrogen peroxide, in various cell lines with an $IC_{50}$ and an inhibitory concentration at 90% of control ($IC_{90}$) of about 4 and 50 nM, respectively.

Niraparib demonstrates selective anti-proliferative activity for cancer cell lines that have been silenced for BRCA-1 or BRCA-2, or carry BRCA-1 or BRCA-2 mutations compared to their wild type counterparts. The antiproliferative activity of niraparib on BRCA-defective cells is a consequence of a cell cycle arrest in G2/M followed by apoptosis. Niraparib is also selectively cytotoxic for selected Ewing's sarcoma, acute lymphocytic leukemia (ALL), non-small cell lung cancer (NSCLC), and small cell lung cancer (SCLC) cell lines, as well as for tumor cell lines carrying homozygous inactivation of the ATM gene. Niraparib demonstrates weak activity on normal human cells. In vivo studies demonstrated strong antitumor activity with BRCA-1 mutant breast cancer (MDA-MB-436), BRCA-2 mutant pancreatic cancer (CAPAN-1), ATM-mutant mantle cell lymphoma (GRANTA-519), serous ovarian cancer (OVCAR3), colorectal cancer (HT29 and DLD-1), patient derived Ewing's sarcoma, and TNBC xenograft models in mice.

Programmed Death 1 (PD-1)

Programmed Death 1 (PD-1) (also known as Programmed Cell Death 1) (encoded by the gene Pdcd1) is a type I transmembrane protein of 268 amino acids originally identified by subtractive hybridization of a mouse T cell line undergoing apoptosis (Ishida et al., *Embo J.,* 11: 3887-95 (1992)). The normal function of PD-1, expressed on the cell surface of activated T cells under healthy conditions, is to down-modulate unwanted or excessive immune responses, including autoimmune reactions.

PD-1 is a member of the CD28/CTLA-4 family of T-cell regulators, and is expressed on activated T-cells, B-cells, and myeloid lineage cells (Greenwald et al., *Annu. Rev. Immunol.,* 23: 515-548 (2005); and Sharpe et al., *Nat. Immunol.,* 8: 239-245 (2007)). PD-1 is an inhibitory member of the CD28 family of receptors that also includes CD28, CTLA-4, ICOS and BTLA. PD-1 is expressed on activated B cells, T cells, and myeloid cells (Agata et al., supra; Okazaki et al. (2002) *Curr. Opin. Immunol* 14:391779-82; Bennett et al. (2003) *J. Immunol.* 170:711-8).

Two ligands for PD-1 have been identified, PD ligand 1 (PD-L1) and PD ligand 2 (PD-L2), both of which belong to the B7 protein superfamily (Greenwald et al, supra). PD-1 has been shown to negatively regulate antigen receptor signaling upon engagement of its ligands (PD-L1 and/or PD-L2).

PD-L1 is expressed in a variety of cell types, including cells of the lung, heart, thymus, spleen, and kidney (see, e.g., Freeman et al., *J. Exp. Med.,* 192(7): 1027-1034 (2000); and Yamazaki et al., *J. Immunol.,* 169(10): 5538-5545 (2002)). PD-L1 expression is upregulated on macrophages and dendritic cells (DCs) in response to lipopolysaccharide (LPS) and GM-CSF treatment, and on T-cells and B-cells upon signaling via T-cell and B-cell receptors. PD-L1 also is expressed in a variety of murine tumor cell lines (see, e.g., Iwai et al., *Proc. Natl. Acad. Sci. USA,* 99(9): 12293-12297 (2002); and Blank et al., *Cancer Res.,* 64(3): 1140-1145 (2004)). In contrast, PD-L2 exhibits a more restricted expression pattern and is expressed primarily by antigen presenting cells (e.g., dendritic cells and macrophages), and some tumor cell lines (see, e.g., Latchman et al., *Nat. Immunol.,* 2(3): 261-238 (2001)). High PD-L1 expression in tumors, whether on the tumor cell, stroma, or other cells within the tumor microenvironment, correlates with poor clinical prognosis, presumably by inhibiting effector T cells and upregulating regulatory T cells (Treg) in the tumor.

PD-1 and family members are type I transmembrane glycoproteins containing an Ig variable-type (V-type) domain responsible for ligand binding and a cytoplasmic tail, which is responsible for the binding of signaling molecules. The cytoplasmic tail of PD-1 contains 2 tyrosine-based signaling motifs, an immunoreceptor tyrosine-based inhibition motif (ITIM) and an immunoreceptor tyrosine-based switch motif (ITSM). PD-1 negatively regulates T-cell activation, and this inhibitory function is linked to an ITSM in the cytoplasmic domain (see, e.g., Greenwald et al., supra; and Parry et al., *Mol. Cell. Biol.,* 25: 9543-9553 (2005)). Following T cell stimulation, PD-1 recruits the tyrosine phosphatases SHP-1 and SHP-2 to the ITSM motif within its cytoplasmic tail, leading to the dephosphorylation of effector molecules, such as CD3, PKCO and ZAP70, which are involved in the CD3 T cell signaling cascade. The mechanism by which PD-1 down-modulates T cell responses is similar to, but distinct from, that of CTLA-4. PD-1 was shown to be expressed on activated lymphocytes, including peripheral CD4+ and CD8+ T cells, B cells, T regs, and natural killer cells. Expression has also been shown during thymic development on CD4−/CD8− (double-negative) T cells, as well as subsets of macrophages and dendritic cells. The ligands for PD-1 (PD-L1 and PD-L2) are constitutively expressed or can be induced in a variety of cell types. PD-L1 is expressed at low levels on various non-hematopoietic tissues, most notably on vascular endothelium, whereas PD-L2 protein is predominantly expressed on antigen-presenting cells found in lymphoid tissue or chronic inflammatory environments. Both ligands are type I transmembrane receptors containing both IgV- and IgC-like domains in the extracellular region and short cytoplasmic regions with no known signaling motifs. Binding of either PD-1 ligand to PD-1 inhibits T cell activation triggered through the T cell receptor. PD-L2 is thought to control immune T cell activation in lymphoid organs, whereas PD-L1 serves to dampen unwarranted T cell function in peripheral tissues. Although healthy organs express little (if any) PD-L1, a variety of cancers were demonstrated to express abundant levels of this T cell inhibitor, which, via its interaction with the PD-1 receptor on tumor-specific T cells, plays a critical role in immune evasion by tumors.

PD-1 deficiency can lead to autoimmunity. For example, C57BL/6 PD-1 knockout mice have been shown to develop a lupus-like syndrome (see, e.g., Nishimura et al., *Immunity,* 11: 141-1151 (1999)). In humans, a single nucleotide polymorphism in the PD-1 gene is associated with higher incidences of systemic lupus erythematosus, type 1 diabetes, rheumatoid arthritis, and progression of multiple sclerosis (see, e.g., Nielsen et al., *Tissue Antigens,* 62(6): 492-497 (2003); Bertsias et al., *Arthritis Rheum.,* 60(1): 207-218 (2009); Ni et al, *Hum. Genet.,* 121(2): 223-232 (2007); Tahoori et al., *Clin. Exp. Rheumatol.,* 29(5): 763-767 (2011); and Kroner et al., *Ann. Neurol.,* 58(1): 50-57 (2005)). Abnormal PD-1 expression also has been implicated in T-cell dysfunctions in several pathologies, such as tumor immune evasion and chronic viral infections (see, e.g., Barber et al., *Nature,* 439: 682-687 (2006); and Sharpe et al., supra). PD-1 is abnormally expressed in a variety of cancers (see, e.g., Brown et al, *J. Immunol.,* 170: 1257-1266 (2003); and Flies et. al, *Yale Journal of Biology and Medicine,* 84: 409-421 (2011)), and PD-L1 expression in some renal cell carcinoma patients correlates with tumor aggressiveness.

Recent studies demonstrate that T-cell suppression induced by PD-1 also plays a role in the suppression of anti-tumor immunity. For example, PD-L1 is expressed on a variety of human and mouse tumors, and binding of PD-1 to PD-L1 on tumors results in T-cell suppression and tumor immune evasion and protection (Dong et al., *Nat. Med.,* 8: 793-800 (2002)). Expression of PD-L1 by tumor cells has been directly associated with their resistance to lysis by anti-tumor T-cells in vitro (Dong et al., supra; and Blank et al., *Cancer Res.,* 64: 1140-1145 (2004)). PD-1 knockout mice are resistant to tumor challenge (Iwai et al., *Int. Immunol.,* 17: 133-144 (2005)), and T-cells from PD-1 knockout mice are highly effective in tumor rejection when adoptively transferred to tumor-bearing mice (Blank et al., supra). Blocking PD-1 inhibitory signals using a monoclonal antibody can potentiate host anti-tumor immunity in mice (Iwai et al., supra; and Hirano et al., *Cancer Res.,* 65: 1089-1096 (2005)), and high levels of PD-L1 expression in tumors are associated with poor prognosis for many human cancer types (Hamanishi et al., *Proc. Natl. Acad. Sci. USA,* 104: 3360-335 (2007), Brown et al, *J. Immunol.,* 170: 1257-1266 (2003); and Flies et al., *Yale Journal of Biology and Medicine,* 84(4): 409-421 (2011)).

In view of the foregoing, strategies for inhibiting PD-1 activity to treat various types of cancer and for immunopotentiation (e.g., to treat infectious diseases) have been developed (see, e.g., Ascierto et al., *Clin. Cancer. Res.,* 19(5): 1009-1020 (2013)). In this respect, monoclonal antibodies targeting PD-1 have been developed for the treatment of cancer (see, e.g., Weber, *Semin. Oncol.,* 37(5): 430-4309 (2010); and Tang et al., *Current Oncology Reports,* 15(2): 98-104 (2013)). For example, nivolumab (also known as BMS-936558) produced complete or partial responses in non-small-cell lung cancer, melanoma, and renal-cell cancer in a Phase I clinical trial (see, e.g., Topalian, *New England J. Med.,* 366: 2443-2454 (2012)), and is currently in Phase III clinical trials. MK-3575 is a humanized monoclonal antibody directed against PD-1 that has shown evidence of antitumor activity in Phase I clinical trials (see, e.g., Patnaik et al., 2012 *American Society of Clinical Oncology (ASCO) Annual Meeting,* Abstract #2512). In addition, recent evidence suggests that therapies which target PD-1 may enhance immune responses against pathogens, such as HIV (see, e.g., Porichis et al., *Curr. HIV/AIDS Rep.,* 9(1): 81-90 (2012)). Despite these advances, however, there remains a need to develop effective therapies and regimens in humans.

Agents that Inhibit PD-1 Signaling

Agents that inhibit PD-1 signaling for use in combination therapies of the present disclosure include those that bind to and block PD-1 receptors on T cells without triggering inhibitory signal transduction, agents that bind to PD-1 ligands to prevent their binding to PD-1, agents that do both, and agents that prevent expression of genes that encode either PD-1 or natural ligands of PD-1. Compounds that bind to natural ligands of PD-1 include PD-1 itself, as well as active fragments of PD-1, and in the case of the B7-H1 ligand, B7.1 proteins and fragments. Such antagonists include proteins, antibodies, anti-sense molecules and small organics.

In some embodiments, an agent that inhibits PD-1 signaling binds to human PD-1. In some embodiments an agent that inhibits PD-1 signaling binds to human PD-L1.

In some embodiments, an agent that inhibits PD-1 signaling for use in combination therapies of the present disclosure is an antibody agent. In some embodiments, a PD-1 antibody agent binds an epitope of PD-1 which blocks the binding of PD-1 to any one or more of its putative ligands. In some embodiments, a PD-1 antibody agent binds an epitope of PD-1 which blocks the binding of PD-1 to two or more of its putative ligands. In a preferred embodiment, a PD-1 antibody agent binds an epitope of a PD-1 protein which blocks the binding of PD-1 to PD-L1 and/or PD-L2. PD-1 antibody agents of the present disclosure may comprise a heavy chain constant region ($F_c$) of any suitable class. In some embodiments, a PD-1 antibody agent comprises a heavy chain constant region that is based upon wild-type IgG1, IgG2, or IgG4 antibodies, or variants thereof.

In some embodiments, an agent that inhibits PD-1 signaling is a monoclonal antibody, or a fragment thereof. In some embodiments, an antibody agent that inhibits PD-1 signaling is a PD-1 antibody or fragment thereof. Monoclonal antibodies that target PD-1 that have been tested in clinical studies and/or received marketing approval in the United. Examples of antibody agents that target PD-1 signaling include, for example, any of the antibody agents listed in the following Table 1:

TABLE 1

Antibody agents that target PD-1.

| Antibody Agent Target (Format) | Developer |
|---|---|
| Opdivo Nivolumab PD-1 (Human IgG4) | Bristol-Myers Squibb ONO |
| Keytruda Pembrolizumab PD-1 (Humanized IgG4) | Merck |
| Tecentriq Atezolizumab PD-L1 (Human IgG1) | Roche |
| Imfinzi Durvalumab PD-L1 (Human IgG1) | Astra Zeneca |
| Bavencio Avelumab PD-L1 (Human IgG1) | Merck KGaA/Pfizer |
| PDR001 PD-1 (Humanized IgG4) | Novartis |
| REGN2810 (SAR-439684) PD-1 (fully human IgG4) | Sanofi, Regeneron |
| BGB-A317 PD-1 (Humanized IgG4) engineered to not bind FcγRI | BeiGene |
| LY3300054 PD-L1 | Eli Lilly |
| BI 754091 (anti-PD-1) | Boehringer Ingelheim |
| IBI308 (anti-PD-1) | Innovent Biologics (Eli Lilly) |
| INCSHR-1210 (anti-PD-1) | Incyte |
| JNJ-63723283 (anti-PD-1) | Janssen Research & Development, LLC |
| JS-001 (anti-PD-1) | Shanghai Junshi Bioscience Co., Ltd. |
| MEDI0680 (AMP-514) anti-PD-1 (Humanized IgG4) | MedImmune Inc |
| MGA-012 (anti-PD-1) | MacroGenics |
| PF-06801591 (anti-PD-1) | Pfizer |
| REGN-2810 (anti-PD-1) | Regeneron |
| TSR-042 anti-PD-1 (Humanized IgG4) | TESARO |
| CX-072 anti-PD-L1 | CytomX Therapeutics |
| FAZ053 anti-PD-L1 | Novartis |
| PD-L1 millamolecule | Bristol-Myers Squibb |

In some embodiments, an antibody agent that inhibits PD-1 signaling is atezolizumab, avelumab, BGB-A317, BI 754091, CX-072, durvalumab, FAZ053, IBI308, INCSHR-1210, JNJ-63723283, JS-001, MEDI-0680, MGA-012, nivolumab, PDR001, pembrolizumab, PF-06801591, REGN-2810, TSR-042, any of the antibodies disclosed in WO2014/179664, or derivates thereof. In some embodiments, an antibody agent that inhibits PD-1 signaling is a PD-1 antibody selected from the group consisting of BGB-A317, BI 754091, CX-072, FAZ053, IBI308, INCSHR-1210, JNJ-63723283, JS-001, LY3300054, MEDI-0680, MGA-012, nivolumab, PD-L1 millamolecule, PDR001, pembrolizumab, PF-06801591, REGN-2810, and TSR-042. In some embodiments, an antibody agent that inhibits PD-1 signaling is a PD-1 antibody selected from the group consisting of nivolumab, pembrolizumab, and TSR-042.

In some embodiments, a PD-1 binding agent is TSR-042, nivolumab, pembrolizumab, atezolizumab, durvalumab, avelumab, PDR-001, tislelizumab (BGB-A317), cemiplimab (REGN2810), LY-3300054, JNJ-63723283, MGA012, BI-754091, IBI-308, camrelizumab (HR-301210), BCD-100, JS-001, CX-072, BGB-A333, AMP-514 (MEDI-0680), AGEN-2034, CS1001, Sym-021, SHR-1316, PF-06801591, LZMO09, KN-035, AB122, genolimzumab (CBT-501), FAZ-053, CK-301, AK 104, or GLS-010, or any of the PD-1 antibodies disclosed in WO2014/179664. In embodiments, an immune checkpoint inhibitor is a PD-1 inhibitor. In embodiments, a PD-1 inhibitor is a PD-1 binding agent (e.g., an antibody, an antibody conjugate, or an antigen-binding fragment thereof). In embodiments, a PD-1 inhibitor is a PD-L1 or PD-L2 binding agent is durvalumab, atezolizumab, avelumab, BGB-A333, SHR-1316, FAZ-053, CK-301, or, PD-L1 millamolecule, or derivatives thereof.

In some embodiments, a PD-1 antibody is pembrolizumab.

Pembrolizumab is an anti-PD-1 monoclonal antibody ("mAb") (also known as MK-3475, SCH 9000475, Keytruda). Pembrolizumab is an immunoglobulin G4/kappa isotype humanized mAb. The mechanism of pembrolizumab consists of the mAb binding to the PD-1 receptor of lymphocytes to block the interaction of PD-1 with PD-L1 and PD-L2 ligands produced by other cells in the body, including tumor cells of certain cancers.

In some embodiments, a PD-1 antibody agent comprises a heavy chain that is 90%, 95%, 97%, 98%, 99% or 100% identical to SEQ ID NO:1, or a fragment thereof. In some embodiments, a PD-1 antibody agent comprises a light chain variable domain that is 90%, 95%, 97%, 98%, 99% or 100% identical to SEQ ID NO:2, or a fragment thereof. In some embodiments, a PD-1 antibody agent comprises a heavy chain variable domain that is 90%, 95%, 97%, 98%, 99% or 100% identical to SEQ ID NO:1 and a light chain variable domain that is 90%, 95%, 97%, 98%, 99% or 100% identical to SEQ ID NO:2.

SEQ ID NO: 1
Pembrolizumab heavy chain
QVQLVQSGVEVKKPGASVKVSCKASGYTFTNYYMYWVRQAPGQGLEWMGG

INPSNGGTNFNEKFKNRVTLTTDSSTTTAYMELKSLQFDDTAVYYCARRD

YRFDMGFDYWGQGTTVTVSSASTKGPSVFPLAPCSRSTSESTAALGCLVK

DYFPEPVTVSWNSGALTSGVHTFPAVLQSSGLYSLSSVVTVPSSSLGTKT

YTCNVDHKPSNTKVDKRVESKYGPPCPPCPAPEFLGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK

SEQ ID NO: 2
Pembrolizumab light chain
EIVLTQSPATLSLSPGERATLSCRASKGVSTSGYSYLHWYQQKPGQAPRL

LIYLASYLESGVPARFSGSGSGTDFTLTISSLEPEDFAVYYCQHSRDLPL

TFGGGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC

Similarly to pembrolizumab, nivolumab (also known as BMS-936558, Opdivo) was first approved by the FDA in 2014 to treat melanoma that cannot be surgically removed or has metastasized following treatment with ipilimumab and a BRAF inhibitor where appropriate.

In some embodiments, a PD-1 antibody agent is as disclosed in International Patent Application Publication WO2014/179664, the entirety of which is incorporated herein. In embodiments, a PD-1 antibody agent is as disclosed in International Patent Application No. PCT/US18/13029, the entirety of which is incorporated herein. In embodiments, a PD-1 antibody agent is as disclosed in International Patent Application No. PCT/US17/59618, the entirety of which is incorporated herein.

In some embodiments, a PD-1 antibody agent comprises a heavy chain variable domain that is 90%, 95%, 97%, 98%, 99% or 100% identical to SEQ ID NO:3. In some embodiments, a PD-1 antibody agent comprises a light chain variable domain that is 90%, 95%, 97%, 98%, 99% or 100% identical to SEQ ID NO:4. In some embodiments, a PD-1 antibody agent comprises a heavy chain variable domain that is 90%, 95%, 97%, 98%, 99% or 100% identical to SEQ ID NO:3 and a light chain variable domain that is 90%, 95%, 97%, 98%, 99% or 100% identical to SEQ ID NO:4.

```
                                                SEQ ID NO: 3
PD-1 antibody agent heavy chain variable domain
EVQLLESGGGLVQPGGSLRLSCAASGFTFSSYDMSWVRQAPGKGLEWVST

ISGGGSYTYYQDSVKGRFTISRDNSKNTLYLQMNSLRAEDTAVYYCASPY

YAMDYWGQGTTVTVSSA

SEQ ID NO: 4
PD-1 antibody agent light chain variable domain
DIQLTQSPSFLSAYVGDRVTITCKASQDVGTAVAWYQQKPGKAPKLLIYW

ASTLHTGVPSRFSGSGSGTEFTLTISSLQPEDFATYYCQHYSSYPWTFGQ

GTKLEIKR
```

In some embodiments, a PD-1 antibody agent comprises one or more CDR sequences as disclosed in International Patent Application Publication WO2014/179664, the entirety of which is incorporated herein. In some embodiments, a PD-1 antibody agent comprises one or more CDR sequences that is 90%, 95%, 97%, 98%, 99% or 100% identical to:

```
                                SEQ ID NO: 5
    HC - CDR1       GFTFSSYDMS

SEQ ID NO: 6
    HC - CDR2       TISGGGSYTY

SEQ ID NO: 7
    HC - CDR3       PYYAMDY

SEQ ID NO: 8
    LC - CDR1       KASQDVGTAVA

SEQ ID NO: 9
    LC - CDR2       WASTLHT

SEQ ID NO: 10
    LC - CDR3       QHYSSYPWT
```

In some embodiments, a PD-1 antibody agent comprises one, two or three heavy chain CDR sequences that is 90%, 95%, 97%, 98%, 99% or 100% identical to CDR sequences listed above. In some embodiments, a PD-1 antibody agent comprises one, two or three light chain CDR sequences that is 90%, 95%, 97%, 98%, 99% or 100% identical to CDR sequences listed above.

Assessing Therapeutic Response

Tumor response can be measured by, for example, the RECIST v 1.1 guidelines. The guidelines are provided by E. A. Eisenhauer, et al., "New response evaluation criteria in solid tumors: Revised RECIST guideline (version 1.1.)," *Eur. J. of Cancer*, 45: 228-247 (2009), which is incorporated by reference in its entirety. RECIST may be used as to assess one or more of tumor response to treatment, date of disease progression, and as a basis for all protocol guidelines related to disease status. RECIST guidelines require, first, estimation of the overall tumor burden at baseline, which is used as a comparator for subsequent measurements. In some embodiments, initial tumor imaging at the patient screening stage is performed within 21 days prior to the date of the first dose of study treatment. Tumors can be measured via use of any imaging system known in the art, for example, by a CT scan, or an X-ray. Magnetic resonance imaging (MRI) may be used, for example, when CT is contradicted or for imaging of the brain. CT imaging is the preferred imaging technique. In some embodiments, the same imaging technique is used for the patient throughout the entire study.

In some embodiments, measurable disease is defined by the presence of at least one measurable lesion. In some embodiments, when more than one measurable lesion is present at baseline, all lesions up to a maximum of five lesions total (and a maximum of two lesions per organ) representative of all involved organs should be identified as target lesions and will be recorded and measured at baseline (this means in instances where patients have only one or two organ sites involved a maximum of two and four lesions respectively will be recorded).

In some embodiments, target lesions are selected on the basis of their size (lesions with the longest diameter), to be representative of all involved organs, and/or selection for lesions that lend themselves to reproducible repeated measurements.

Lymph nodes may merit special mention since they are normal anatomical structures which may be visible by imaging even if not involved by tumor. Pathological nodes which are defined as measurable may be identified as target lesions have a short axis of >15 mm by CT scan. In some embodiments, only the short axis of these nodes contributes to the baseline sum. The short axis of the node is the diameter normally used by radiologists to judge if a node is involved by solid tumor. Nodal size is normally reported as two dimensions in the plane in which the image is obtained (for CT scan this is almost always the axial plane; for MRI the plane of acquisition may be axial, sagittal or coronal). The smaller of these measures is the short axis.

For example, an abdominal node which is reported as being 20 mm·30 mm has a short axis of 20 mm and qualifies as a malignant, measurable node. In this example, 20 mm should be recorded as the node measurement. All other pathological nodes (those with short axis >10 mm but <15 mm) should be considered non-target lesions. Nodes that have a short axis <10 mm are considered non-pathological and should not be recorded or followed.

A sum of the diameters (longest for non-nodal lesions, short axis for nodal lesions) for all target lesions will be calculated and reported as the baseline sum diameters. If lymph nodes are to be included in the sum, then as noted above, only the short axis is added into the sum. The baseline sum diameters will be used as reference to further characterize any objective tumor regression in the measurable dimension of the disease.

All other lesions (or sites of disease) including pathological lymph nodes should be identified as non-target lesions and should also be recorded at baseline. Measurements are not required and these lesions should be followed as 'present', 'absent', or in rare cases 'unequivocal progression.' In addition, it is possible to record multiple nontarget lesions involving the same organ as a single item on the case record form (e.g. 'multiple enlarged pelvic lymph nodes' or 'multiple liver metastases').

In some embodiments, the first on-study imaging assessment should be performed at 9 weeks (63 days±7 days) from the date of the first dose of the study treatment. In some embodiments, in the case of progressive disease (PD), a confirmatory image will be required 4 weeks later (91 days±7 days).

In some embodiments, subsequent imaging should be performed every 9 weeks (63 days±7 days) or more frequently if clinically indicated at the time of suspected disease progression.

In some embodiments, after 1 year of radiographic assessments, patients will have imaging performed every 12 weeks (84 days±7 days).

In some embodiments, imaging will continue to be performed until one of the following occurs: the start of a new cancer treatment, the patient withdrawals consent, the patient dies, or the end of the study has been reached.

In some embodiments, patients who discontinue study treatment for reasons other than PD, will continue post-treatment imaging studies for disease status follow-up every 9 weeks (63 days±7 days) depending on the length of treatment with the study until: disease progression, the patient starts a new treatment outside of the study, the patient withdrawals consent, the patient becomes lost to follow-up, the patient dies, or the end of the study has been reached.

In some embodiments, irRECIST guidelines will also be incorporated in cases of disease progression to account for unique tumor characteristics seen during treatment with pembrolizumab and to assess continuation of treatment in clinically stable patients until progression is confirmed. In some embodiments, RECIST v1.1 will be adapted to incorporate these special guidelines, as using RECIST v1.1 alone in immunotherapy trials would lead to the declaration of progressive disease (PD) too early. Antibody agents that inhibit PD-1 signaling (e.g., pembrolizumab) may produce antitumor effects by potentiating endogenous cancer-specific immune responses. The response patterns with this type of approach tend to extend beyond the typical time course of responses seen with cytotoxic agents and can manifest a clinical response after an initial increase in tumor burden or appearance of new lesions.

Therefore, in some embodiments if repeat imaging shows <20% increase in tumor burden compared with (1) nadir, stable, or improved previously indicated new lesion (if identified as cause for initial PD), and (2) stable/improved non-target disease (if identified as cause for initial PD), treatment may be continued or resumed, and the next imaging should be conducted according to the above protocol schedule of 9 weeks (63 days±7 days) or if it has been one year since beginning of treatment (first radiographic image taken), 12 weeks (84 days±7 days).

In some embodiments, incorporating both RECIST v1.1 plus irRESIST v1.1 guidelines, patients will be discontinued from the study if repeat imaging confirms PD due to any of the following: tumor burden remains ≥20% and at least a 5-mm absolute increase in tumor size compared with nadir, non-target disease resulting in initial PD is worse, new lesion resulting in initial PD is worse, additional new lesions appeared since last evaluation, additional new non-target progression is seen since last evaluation.

In some embodiments, incorporating both RECIST v1.1 plus irRESIST v1.1 guidelines, patients may remain on pembrolizumab while waiting for confirmation of PD if they are clinically stable, which means the patient has absence of signs and symptoms indicating clinically significant progression of disease including worsening of laboratory values, the patient has no decline in ECOG status (0=asymptomatic through 5=death), patient is absent of rapid progression of disease, and patient has absence of progressive tumor at critical anatomical sites. Patients on immunotherapy can have transient tumor flare in the first few months of treatment, but with subsequent disease response. Thus, it is best to keep patients on the treatment while waiting for confirmation of PD if possible.

In some embodiments, the primary efficacy endpoint for the study is objective response rate (ORR) defined as a proportion of patients achieving CR or PR as assessed by RECIST v1.1. ORR by irRESIST will also be evaluated as a secondary endpoint. Tumor assessments after the initiation of further anticancer therapy are excluded for assessment of best overall response.

In some embodiments, duration of response (DOR) will be evaluated as a secondary endpoint. In some embodiments, DOR is defined as the time from first documentation of CR or PR by RESIST v1.1 guidelines until (1) the time of first documentation of disease progression per RESIST v1.1 and (2) the time of first documentation of disease progression per irRESIST. In some embodiments, date of progression based on RESIST v1.1 or irRESIST may be overwritten in patients with OC if clinical criteria indicate earlier progression as adjucated by the study committee.

In some embodiments, disease control rate (DCR) will be assessed as a secondary endpoint and is defined as the proportion of patients achieving CR, PR, or SD as assessed by RESIST v1.1 and irRESIST.

In some embodiments, progression-free survival (PFS) will be assessed as secondary endpoint and is defined as the time from enrollment to the earlier date of assessment of progression or death by any cause in the absence of progression based on (1) the time of first documentation of disease progression per RESIST v1.1 and (2) the time of first documentation of disease progression per irRESIST. In some embodiments, date of progression based on RESIST v1.1 or irRESIST may be overwritten in patients with OC if clinical criteria indicate earlier progression as adjucated by the study committee.

In some embodiments, overall survival (OS) will be assessed as a secondary endpoint and is defined as the time from date of first dose of study treatment to the date of death by any cause. New malignancy information will also be collected as part of this assessment.

In some embodiments, tumor markers (CA-125) will not be used for defining objective responses or disease progression, but can be used for clinical decisions.

In some embodiments, clinical criteria GCIG will be used for management of OC patients with clinical events (e.g., niraparib bowel obstruction) without radiographic evidence of disease progression.

In some embodiments, the present disclosure includes comparisons of results achieved for two or more agents, entities, situations, sets of conditions, populations etc. As will be understood by those of skill in the art, such agents, entities, situations, sets of conditions, populations, etc. can be considered "comparable" to one another when they are not identical but are sufficiently similar to permit comparison therebetween so that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Comparisons as described herein are often made to an appropriate "reference". As used herein, the term "reference" refers to a standard or control relative to which a comparison is performed. For example, in some embodiments, an agent, animal, individual, population, sample, sequence, or value of interest is compared with a reference or control agent, animal, individual, population, sample, sequence, or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Pharmacokinetics

In some embodiments patients may be evaluated for pharmacokinetics information. Pharmacokinetic data can provide insight regarding the fate of a given drug (i.e., therapeutic agent) from administration to elimination from the human body.

Pharmacokinetic data can be obtained by known techniques in the art. Due to the inherent variation in pharmacokinetic and pharmacodynamic parameters of drug metabolism in human subjects, appropriate pharmacokinetic and pharmacodynamic profile components describing a particular composition can vary. Typically, pharmacokinetic and pharmacodynamic profiles are based on the determination of the mean parameters of a group of subjects. The group of subjects includes any reasonable number of subjects suitable for determining a representative mean, for example, 5 subjects, 10 subjects, 16 subjects, 20 subjects, 25 subjects, 30 subjects, 35 subjects, or more. The mean is determined by calculating the average of all subject's measurements for each parameter measured.

In some embodiments, a patient population includes one or more subjects ("a population of subjects") suffering from metastatic disease.

In some embodiments, a patient population includes one or more subjects that is suffering from or susceptible to cancer. In some embodiments, a patient population includes one or more subjects (e.g., comprises or consists of subjects) suffering from cancer. For example, in some embodiments, a patient population suffering from cancer may have previously been treated with a prior therapy, for example, radiation and/or chemotherapy.

In some embodiments, the pharmacokinetic parameter(s) can be any parameters suitable for describing the present composition.

General Protocol for Dosing

As described herein, provided methods comprise administering a therapy that inhibits PARP and a therapy that inhibits PD-1 signaling a in combination to a patient, a subject, or a population of subjects according to a regimen that achieves any one of or combination of: prolonged progression free survival; reduced hazard ratio for disease progression or death; and/or prolonged overall survival or a positive overall response rate.

In some embodiments, an agent that inhibits PARP (e.g., niraparib) is administered in combination (e.g., simultaneously or sequentially) with an agent that inhibits PD-1 signaling. In some embodiments, an agent that inhibits PD-1 signaling is a protein, antibody, anti-sense molecule or small organic molecule inhibitor of PD-1 signaling. In some embodiments, an agent that inhibits PD-1 signaling binds to PD-1. In some embodiments, an agent that inhibits PD-1 signaling is a PD-1 antibody agent (e.g., pembrolizumab).

In some embodiments, an agent that inhibits PARP (e.g., niraparib) is administered in combination (e.g., simultaneously or sequentially) with an immunotherapy (e.g. a PD-1 antibody agent). In some embodiments, the immunotherapy is or comprises administration of an agent that targets a specific antigen (e.g. PD-1); in some embodiments, immunotherapy is or comprises administration of an antibody agent that targets PD-1 (e.g., pembrolizumab).

In some embodiments, one or more doses of an agent that inhibits PARP (e.g., niraparib) is administered before, during, or after administration of one or more doses of an agent that inhibits PD-1 signaling (e.g., pembrolizumab). In some embodiments, an agent that inhibits PARP (e.g., niraparib) and an agent that inhibits PD-1 signaling (e.g., pembrolizumab) are administered in overlapping regimens. In some embodiments, at least one cycle of an agent that inhibits PARP (e.g., niraparib) is administered prior to initiation of therapy with an agent that inhibits PD-1 signaling (e.g., pembrolizumab). In some embodiments, administration "in combination" includes administration of an agent that inhibits PARP (e.g., niraparib) and simultaneously or sequentially administering an agent that inhibits PD-1 signaling (e.g., an antibody agent such as pembrolizumab).

In some embodiments, administration of a particular dose or cycle of an agent that inhibits PARP (e.g., niraparib) is separated in time from a particular dose or cycle of an agent that inhibits PD-1 signaling (e.g., pembrolizumab) by a time period having a length that may be, for example, 1 minute, 5 minutes, 30 minutes, 1 hour, 2 hours, 5 hours, 10 hours, 12 hours, 24 hours, 48 hours, 72 hours, 96 hours, 1 week, 2 weeks, or more. In some embodiments, the range may be bounded by a lower limit and an upper limit, the upper limit being larger than the lower limit. In some embodiments, the lower limit may be about 1 minute, about 5 minutes, about 15 minutes, about 30 minutes, about 45 minutes, about 1 hour, about 2 hours, about 4 hours, about 6 hours, about 12 hours, about 24 hours, about 48, hours, about 72 hours, about 96 hours, or about 1 week. In some embodiments, the upper limit may be about 2 weeks, about 3 weeks, about 4 weeks, about 5 weeks, about 6 weeks, about 8 weeks, or about 12 weeks. In some embodiments, the administration of a particular dose of an agent that inhibits PARP (e.g., niraparib) is separated in time from a particular dose of an agent that inhibits PD-1 signaling (e.g., pembrolizumab) by a time period within the range of about 1 minute to about 12 weeks. In some embodiments, the range may be about 1 minute to about 8 weeks. In some embodiments, the range may be about 1 minute to about 6 weeks. In some embodiments, the range may be about 1 minute to about 4 weeks. In some embodiments, the range may be about 1 minute to about 2 weeks. In some embodiments, the range may be about 1 minute to about 1 week. In some embodiments, the range may be about 1 minute to about 96 hours. In some embodiments, the range may be about 1 minute to about 72 hours. In some embodiments, the range may be about 1 minute to about 48 hours. In some embodiments, the range may be about 1 minute to about 24 hours. In some embodiments, the range may be about 1 minute to about 12 hours. In some embodiments, the range may be about 1 minute to about 8 hours. In some embodiments, the range may be about 1 minute to about 4 hours. In some embodiments, the range may be about 1 minute to about 2 hours. In some embodiments, the range may be about 1 minute to about 1 hour. In some embodiments, the range may be about 1 minute to about 11 minute.

In some embodiments, combination therapy with an agent that inhibits PARP (e.g., niraparib) and an agent that inhibits PD-1 signaling (e.g., pembrolizumab) is administered to a patient or population of subjects who has exhibited response to prior therapy. In some embodiments, the patient or population of subjects has exhibited response to prior therapy with a chemotherapeutic agent. In some such embodiments, the chemotherapeutic agent is a platinum agent. In some embodiments, a platinum-based agent is selected from cisplatin, carboplatin, oxaliplatin, nedaplatin, triplatin tetranitrate, phenanthriplatin, picoplatin, or satraplatin.

In some embodiments, the regimen comprises at least one oral dose of an agent that inhibits PARP (e.g., niraparib). In some embodiments, the regimen comprises a plurality of oral doses. In some embodiments, the regimen comprises once daily (QD) dosing. In some embodiments, an agent that inhibits PARP (e.g., niraparib) is administered on the first day of a 21-day cycle upon completion of infusion with an agent that inhibits PD-1 signaling (e.g., pembrolizumab). In some embodiments, an agent that inhibits PARP (e.g., niraparib) is administered daily throughout the regimen cycle at the same time every day. In some embodiments the same time every day is preferably in the morning.

In some embodiments, the regimen comprises of one infusion of an agent that inhibits PD-1 signaling (e.g., pembrolizumab) per regimen cycle. In some embodiments, the regimen comprises of one, 30-minute infusion of an agent that inhibits PD-1 signaling (e.g., pembrolizumab) per regimen cycle. In some embodiments, the regimen comprises of one, 30-minute infusion of an agent that inhibits PD-1 signaling (e.g., pembrolizumab) on the first day of each regimen cycle.

In some embodiments, the regimen comprises at least one 2 week-8 week cycle. In some embodiments, the regimen comprises a plurality of 2 week-8 week cycles. In some embodiments, the regimen comprises one 2 week-8 week cycle. In some embodiments, the regimen comprises two 2 week-8 week cycles. In some embodiments, the regimen comprises three or more 2 week-8 week cycles. In some embodiments, the regimen comprises continuous 2 week-8 week cycles.

In some embodiments, the regimen comprises at least one 28 day cycle. In some embodiments, the regimen comprises a plurality of 28 day cycles. In some embodiments, the regimen comprises one 28 day cycle. In some embodiments, the regimen comprises two 28 day cycles. In some embodiments, the regimen comprises three or more 28 day cycles. In some embodiments, the regimen comprises continuous 28 day cycles.

In some embodiments, the regimen comprises at least one 21 day cycle. In some embodiments, the regimen comprises a plurality of 21 day cycles. In some embodiments, the regimen comprises one 21 day cycle. In some embodiments, the regimen comprises two 21 day cycles. In some embodiments, the regimen comprises three or more 21 day cycles. In some embodiments, the regimen comprises continuous 21 day cycles.

In some embodiments, the regimen comprises administration of an effective dose of an agent that inhibits PARP (e.g., niraparib) daily until disease progression or unacceptable toxicity occurs. In some embodiments, the regimen comprises a daily dose of 100 mg, 200 mg, 300 mg or more of a PARP inhibitor (e.g., niraparib) per day dosed until disease progression or unacceptable toxicity occurs. In some embodiments, the range is bounded by a lower limit and an upper limit, the upper limit being larger than the lower limit. In some embodiments, the lower limit may be about 10 mg, about 25 mg, about 50 mg, or about 100 mg. In some embodiments, the upper limit may be about 150 mg, about 200 mg, about 250 mg, about 300 mg, about 350 mg, about 400 mg or about 500 mg. In some embodiments, the oral dose is an amount of a PARP inhibitor (e.g., niraparib) within a range of about 10 mg to about 500 mg. In some embodiments, the dose is within a range of about 25 mg to about 400 mg. In some embodiments, the dose is within a range of about 50 mg to about 300 mg. In some embodiments, the dose is within a range of about 150 mg to about 350 mg. In some embodiments, the dose is within a range of about 50 mg to about 250 mg. In some embodiments, the dose is within a range of about 50 mg to about 200 mg. In some embodiments, the dose is within a range of about 50 mg to about 100 mg. In some embodiments, the dose is within a range of about 100 mg to about 300 mg.

In some embodiments, the oral dose of niraparib is administered in one or more unit dosage forms. In some embodiments, the one or more unit dosage forms are capsules. In some embodiments, each unit dosage form comprises about 100 mg of PARP inhibitor (e.g., niraparib). It is understood that any combination of unit dosage forms can be combined to form a once daily (QD) dose. For example, three 100 mg unit dosage forms can be taken once daily such that 300 mg of PARP inhibitor (e.g., niraparib) is administered once daily. In some embodiments, two 100 mg unit dosage forms can be taken once daily such that 200 mg of PARP inhibitor (e.g., niraparib) is administered once daily In some embodiments, one 100 mg unit dosage forms can be taken once daily such that 100 mg of PARP inhibitor (e.g., niraparib) is administered once daily.

In some embodiments, the regimen comprises a single infusion of at least 200 mg of an agent that inhibits PD-1 signaling (e.g., pembrolizumab). In some embodiments, the regimen comprises a single infusion of an agent that inhibits PD-1 signaling (e.g., pembrolizumab) over a time period of at least 25 minutes, 30 minutes, 35 minutes, 40 minutes, or more. In some embodiments, the range may be bounded by a lower limit and an upper limit, the upper limit being larger than the lower limit. In some embodiments, the lower limit may be about 25 minutes, or about 30 minutes. In some embodiments, the upper limit may be about 35 minutes or about 40 minutes. In some embodiments, the range may be about 25 minutes to about 40 minutes. In some embodiments, the range may be about 25 minutes to about 35 minutes. In some embodiments, the range may be about 25 minutes to about 30 minutes. In some embodiments an agent that inhibits PD-1 signaling (e.g., pembrolizumab) is administered through intravenous (IV) infusion. In some embodiments an intravenous dose of an agent that inhibits PD-1 signaling (e.g., pembrolizumab) is administered in one or more unit dosage forms.

EXAMPLES

The following examples are provided to illustrate, but not limit the claimed invention.

Example 1—Low Doses of an Agent that Inhibits PARP in Combination with an Agent that Inhibits PD-1 Signaling Induces Synergistic Anti-Tumor Activity Tumor Inoculation and Treatment Schedule C57BL/6 mice were inoculated subcutaneously at the right flank with primary Murine skin cancer model mSK6005 fragment developed from $Apc^{Min}/J$ heterozygous background (R2P4, 2-4 mm in diameter) for tumor development. The mice were randomized and treatment started when the average tumor size reached 148 $mm^3$.

The mice were separated into six groups and treated with niraparib, anti-PD-1 (Bio X Cell, New Hampshire), vehicle (comprising 0.5% methylcellulose), or PD-1 isotype (Bio X Cell, New Hampshire). Specifically, the treatment schedule for each group is described in Table 2.

TABLE 2

Treatment schedule for each group.

| Group | N | Treatment | Dose (mg/kg) | Dosing route | Schedule |
|---|---|---|---|---|---|
| 1 | 5 | Vehicle | — | oral (p.o.) | every day (QD) × 19 |
|   |   | PD-1 isotype | 5 | intraperitoneal (i.p.) | Twice weekly (BIW) × 3 |
| 2 | 5 | Niraparib | 50 | p.o. | QD × 19 |
| 3 | 5 | anti-PD-1 | 5 | i.p. | BIW × 3 |
| 4 | 5 | Niraparib | 50 | p.o. | QD × 19 |
|   |   | anti-PD-1 | 5 | i.p. | BIW × 3 |
| 5 | 5 | Niraparib | 25 | p.o. | QD × 19 |
| 6 | 5 | Niraparib | 25 | p.o. | QD × 19 |
|   |   | anti-PD-1 | 5 | i.p. | BIW × 3 |

All the procedures related to animal handling, care, and the treatment in this study were performed according to guidelines approved by the Institutional Animal Care and Use Committee (IACUC) following the guidance of the Association for Assessment and Accreditation of Laboratory Animal Care (AAALAC). At the time of routine monitoring, the animals were checked for any effects of tumor growth on normal behavior such as mobility, food and water consumption (by looking only), body weight gain/loss, eye/hair matting and any other abnormal effect. Observed clinical signs were recorded on the basis of the numbers of animals within each subset.

Figure 2:
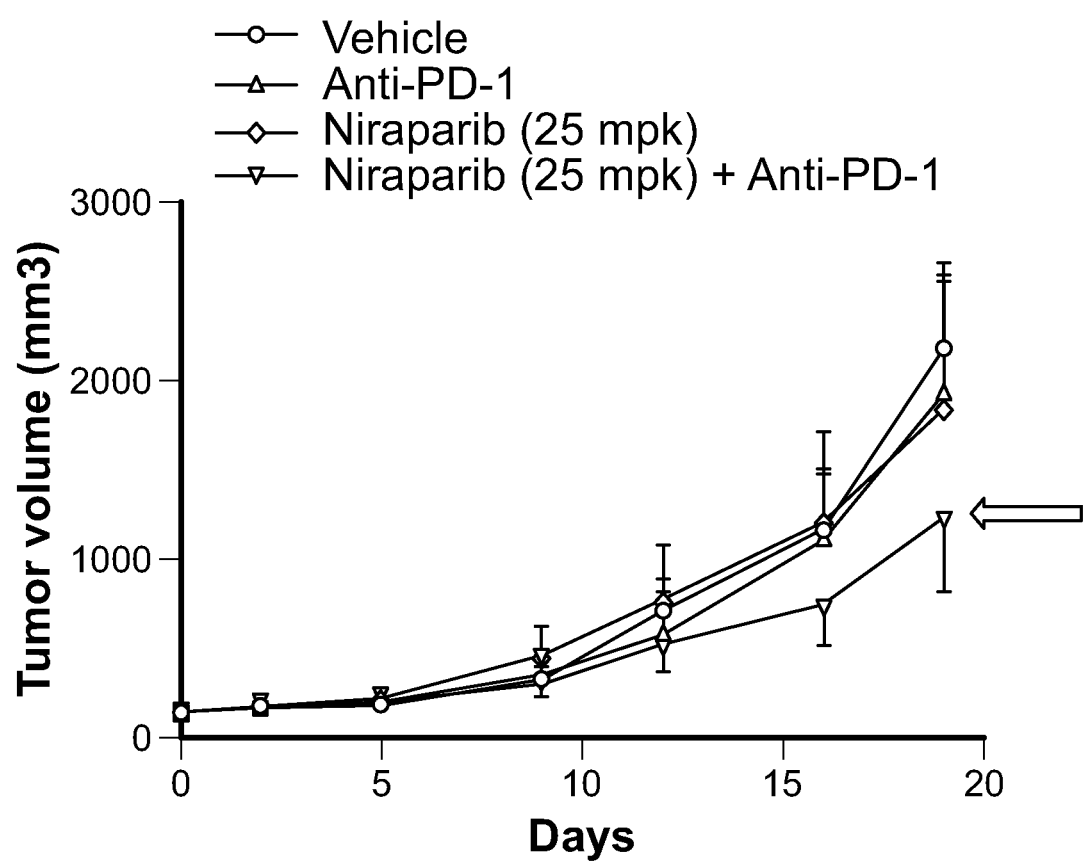
FIG. 2 depicts tumor growth curves of mice treated with vehicle, anti-PD-1 (5 mg/kg, BIW), niraparib (25 mg/kg, QD), or niraparib (25 mg/kg, QD) in combination with anti-PD-1 (5 mg/kg, BIW). The combination endpoint is noted by an arrow.

Tumor size was measured twice weekly using a caliper. As shown in FIG. 1, the high dose niraparib (50 mg/kg, QD) and anti-PD-1 (5 mg/kg, BIW) combination showed no synergistic or additive effect. In contrast, as shown in FIG. 2, the low dose niraparib (25 mg/kg, QD) and anti-PD-1 (5 mg/kg, BIW) combination induced synergistic anti-tumor activity.

Example 2—Treatment of Cancer with a PARP Inhibitor in Combination with an Anti-PD-1 Agent This example describes a multicenter, open-label, single-arm Phase 1/2 study evaluating the safety and efficacy of combination treatment with a PARP inhibitor (niraparib) in combination with an anti-PD-1 agent (pembrolizumab).

Inclusion Criteria

To be eligible for this study, patients had to have histologically proven, advanced (unresectable), metastatic cancer. Specifically, patients with high-grade serous ovarian, fallopian tube, or primary peritoneal cancer, which are exemplary gynecological cancers, who have recurrent disease and have been previously treated for advanced/metastatic disease and who experienced a response lasting at least 6 months to first-line platinum-based therapy but currently considered platinum-resistant, were eligible for the combination therapy treatment described herein.

Administration of an Exemplary Agent that Inhibits PARP

Niraparib was supplied as 100-mg capsules and administered orally once daily (QD) continuously starting on Cycle 1/Day 1. The daily dose administered each day depended on the phase of the study, and in Phase 1, the cohort assignment. Daily doses of niraparib were 200 mg/day or 300 mg/day orally (300 mg as 3×100-mg capsules or 200 mg as 2×100-mg capsules).

Treatment with niraparib was interrupted for any treatment-related non-hematologic CTCAE Grade 3 or 4 event. Once resolved to Grade≤1, and the patient may restart treatment with niraparib with a dose level reduction.

Administration of an Exemplary Agent that Inhibits PD-1

Pembrolizumab was administered at the study site on Day 1 of each 21-day treatment cycle after all procedures and assessments were completed. Pembrolizumab was administered up to 3 days before or after the scheduled Day 1 of each cycle after Cycle 2 due to administrative reasons.

Pembrolizumab was administered at a dose of 200 mg IV using a 30-minute IV infusion. Given the variability of infusion pumps from site to site, however, a window between −5 minutes and +10 minutes is permitted.

Results

A total of nine ovarian cancer patients were evaluated to date in the Phase I portion of this trial, and the Response Evaluation Criteria in Solid Tumors (RECIST) v1.1 results are in Table 3. Based on these results, the Phase 2 dose (RP2D) and schedule was determined to be niraparib 200 mg/day orally on days 1-21 and pembrolizumab 200 mg intravenously on day 1 of each 21-day cycle; provided, however, that the niraparib dose may be escalated from 200 mg daily to 300 mg daily if hemoglobin ≥9 g/dL, platelets ≥100,000/µL and neutrophils ≥1500/µL for all labs performed during one or more cycles.

TABLE 3

RECIST results for OC patients.

| Patient | Tumor type | Response | Niraparib Dose | Pembrolizumab Dose | Time on Study Cycle | BRCA Status |
|---|---|---|---|---|---|---|
| 1 | ovarian | CR | 300 mg, reduced to 200 mg | 200 mg | 9+ | WT |
| 2 | ovarian | PR | 200 mg | 200 mg | 9 | Mutant |
| 3 | ovarian | PR | 300 mg, reduced to 200 mg | 200 mg | 11+ | Mutant |

TABLE 3-continued

RECIST results for OC patients.

| Patient | Tumor type | Response | Niraparib Dose | Pembro-lizumab Dose | Time on Study Cycle | BRCA Status |
|---|---|---|---|---|---|---|
| 4 | ovarian | PR | 300 mg, reduced to 200 mg | 200 mg | 8+ | WT |
| 5 | ovarian | SD | 200 mg | 200 mg | 3 | WT |
| 6 | ovarian | SD | 200 mg | 200 mg | 6 | WT |
| 7 | ovarian | SD | 200 mg | 200 mg | 5 | Not determined |
| 8 | ovarian | SD | 200 mg | 200 mg | 6 | WT |
| 9 | ovarian | NE | 200 mg | 200 mg | — | WT |

Consistent with the data described in Example 1, this clinical study demonstrated that low dose PARP inhibitor (e.g., niraparib) is efficacious when used in combination with an agent for inhibiting PD-1 signaling (e.g., pembrolizumab). In addition, this study surprisingly demonstrated that PARP inhibition in combination with inhibition of PD-1 signaling is effective in treating BRCA-wild type patients that are platinum-resistant and have a gynecological cancer. While prior studies have demonstrated improved progression-free survival in patients with platinum-sensitive, relapsed serous ovarian cancer that harbored a BRCA1/2 mutation, no benefit was observed in platinum-resistant cohorts without BRCA 112 mutation (see NCT00753545; D0810000019; Study 19). Accordingly, Applicants have discovered a combination therapy that satisfies a high-unmet medical need and is efficacious for BRCA-wild type patients who are platinum-resistant.

Example 3—Clinical Dose-finding Combination Study of a Parp Inhibitor and an Anti-PD-1 Agent for the Treatment of Cancer The following Example describes findings from phase 1 and interim findings from phase 2 (TOPACIO; NCT02657889) of a clinical study designed to evaluate combination treatment with niraparib and an anti-PD-1 agent (pembrolizumab).

Background

Treatment options for patients with advanced or metastatic triple-negative breast cancer (TNBC) or recurrent platinum-resistant ovarian cancer (OC) are limited. Single-agent activity is modest with PARP inhibitors in BRCA wild-type TNBC (objective response rate (ORR): 0%) and platinum-resistant OC (ORR: ≤16%) and with anti-PD-1 agents in previously treated TNBC (pembrolizumab ORR: 4.7%) and OC (nivolumab ORR: 15%) (Gelmon K A, et al. Lancet Oncol. 2011; 12:852-861; Sandhu S K, et al. Lancet Oncol. 2013; 14:882-892; Adams S, et al. J Clin Oncol. 2017: 35 (suppl 15):1008; Hamanishi J, et al. J Clin Oncol. 2015; 33:4015-4022).

PARP inhibition may enhance the immune response in tumors treated with anti-PD-1 therapy, via generation of cytosolic DNA that then activates T cells through the stimulator of interferon genes (STING) pathway, rendering tumors immunologically "hot" with an increase of infiltrating lymphocytes (Erdal E, et al. Genes Dev. 2017; 31:353-369; Mouw K W, et al. Cancer Discov. 2017; 7:675-693). Preclinical data have suggested therapeutic synergy between PARP inhibitors and PD-1 inhibitors in OC and TNBC (Higuchi T, et al. Cancer Immunol Res. 2015; 3:1257-1268; Huang J, et al. Biochem Biophys Res Commun. 2015; 463:551-556; Jiao S, et al. Clin Cancer Res. 2017; 23:3711-3720).

Clinical Study Objectives

The primary objective of phase 1 of this clinical study was to evaluate dose-limiting toxicities (DLTs) of combination treatment with niraparib and an anti-PD-1 agent, and establish a recommended phase 2 dose (RP2D) of niraparib to be administered with an anti-PD-1 agent. The objective of phase 2 was to estimate the clinical activity of combination treatment with niraparib and an anti-PD-1 agent separately for patients with metastatic TNBC and patients with recurrent platinum-resistant OC. Secondary objectives for both phases included evaluation of safety and tolerability of combination treatment and evaluation of the duration of response to combination treatment in phase 2.

Methods

Inclusion Criteria

To be eligible for this study, patients with advanced (unresectable) or metastatic breast or ovarian cancer were subjected to the following criteria. For the phase 1 population, patients with advanced or metastatic breast cancer that was estrogen receptor expression negative (<1% of cells), progesterone receptor expression negative (<1% of cells), and HER2-negative (i.e., TNBC) were included. A maximum of four lines of cytotoxic therapy was permitted. Also included in phase 1 were patients with epithelial ovarian, fallopian tube, or primary peritoneal cancer who were considered to have platinum-resistant disease or platinum-refractory disease, but experienced a response lasting at least six months as a result of first-line platinum-based therapy. Patients who received up to five lines of cytotoxic therapy were included.

For the phase 2 population, patients with advanced or metastatic TNBC who received up to two prior lines of cytotoxic therapy were included. Adjuvant and/or neoadjuvant therapies were not counted in the number of lines of therapy. Patients who previously received platinum chemotherapy in the metastatic setting were allowed to enroll in the study if they did not progress while on or within eight weeks from the day of the last platinum administration. Additionally, patients with high-grade serous or endometroid ovarian, fallopian tube, or primary peritoneal cancer who were considered to have platinum-resistant disease were included. A maximum of two lines of cytotoxic therapy was permitted.

Other key inclusion criteria for the study included measurable lesions by RECIST v1.1 and an Eastern Cooperative Oncology Group (ECOG) performance score of 0 or 1.

Exclusion Criteria

Patients with primary platinum refractory OC, such as progressive disease on or within 6 months of first-line platinum therapy, were excluded from the study. Additionally, patients who received prior treatment with an anti-PD-1, anti-PD-L1, or anti-PD-L2 agent or known PARP inhibitor were ineligible to participate in the study.

Clinical Study Design

Figure 3:
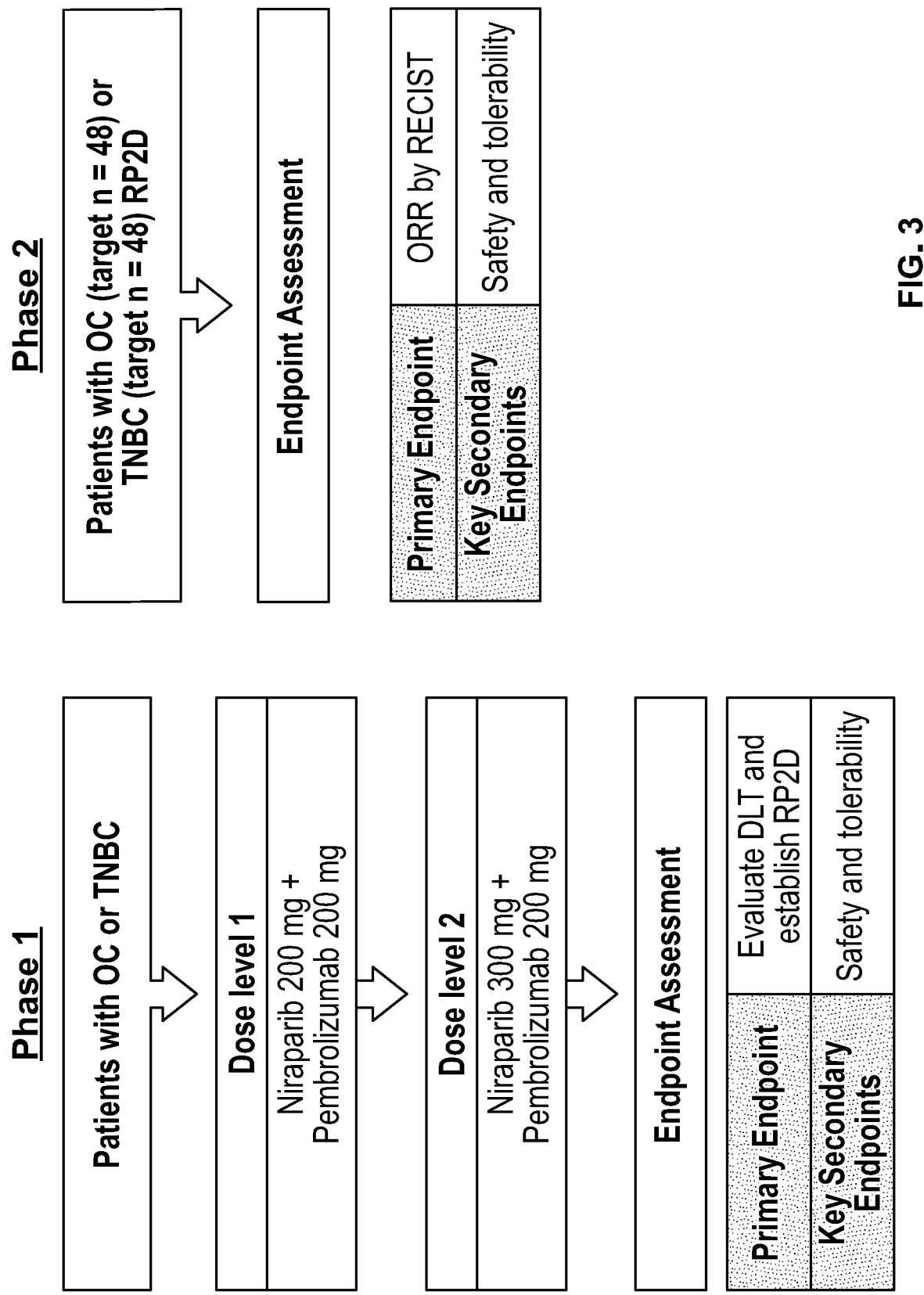
FIG. 3 depicts clinical study design.

In phase 1, DLTs were evaluated in a 6+6 dose escalation design (FIG. 3). Dose level 1 included 200 mg niraparib per day orally and 200 mg intravenous (IV) pembrolizumab on day 1 of each 21-day cycle. Dose level 2 included 300 mg niraparib per day orally and 200 mg IV pembrolizumab on day 1 of each 21-day cycle. RP2D was determined based on the following: DLT rate in first and subsequent cycles of treatment, rate of a non-DLT adverse event (AE), dose modifications, pharmacokinetics, niraparib dose intensity, and signs of clinical efficacy. Tumor BRCA (tBRCA) mutation status was evaluated using the Myriad Genetics research homologous recombination deficiency assay. PD-L1 expression was evaluated and PD-L1 status for both TNBC and OC was determined using a 1% provisional cutoff by immunohistochemistry (IHC) using an investigational version of the PD-L1 IHC 22C3 pharmDx (Agilent, Carpinteria, Calif., USA). The "combined positive score" was defined as the number of stained tumor and immune cells relative to total number of tumor cells.

In phase 2, two cohorts of patients with advanced TNBC or OC were evaluated using the RP2D of 200 mg niraparib (FIG. 3). The study was amended midway through to allow escalation of niraparib to 300 mg after 2 cycles in patients who did not have significant hematologic toxicity. The schedule of on-study assessments was as follows. The first scan was performed at nine weeks (±7 days). If progressive disease was apparent, a confirmatory scan was performed four weeks later. Subsequent scans were performed every nine weeks, and at the time of progression. If a complete response (CR) or partial response (PR) was observed, the response was confirmed by repeat imaging. Phase 2 included a 2-stage design (total n=24+24 for each tumor cohort). The efficacy population included patients who received any amount of study drug with at least one evaluable post-baseline tumor scan.

Results

Patients—Phase 1

Fourteen patients were enrolled in phase 1 of the study (TNBC, n=5; OC, n=9) as shown in Table 4. The most common prior treatments for OC patients in phase 1 were platinum-based therapy (received by all patients) and taxanes (received by 89% of patients). The most common prior treatments for metastatic TNBC were taxanes and cyclophosphamide (received by all patients) and anthracycline (received by 60% of patients).

TABLE 4

Phase 1 patient demographics and baseline characteristics.

| | OC (n = 9) | TNBC (n = 5) |
|---|---|---|
| Age (years) | | |
| Median (min, max) | 62.0 (48, 72) | 56.0 (43, 71) |
| ECOG performance score, n (%) | | |
| 0 | 7 (77.8) | 2 (40.0) |
| 1 | 2 (22.2) | 3 (60.0) |
| Number of previous lines of therapy for advanced disease, median (range) | 2 (1-4) | 2 (1-4) |
| Patients with previous neoadjuvant/adjuvant therapies n (%) | 6 (66.7) | 5 (100.0) |

SD: standard deviation;
min: minimum;
max: maximum

Safety—Phase 1

Of the seven patients administered dose level 1, one patient had DLTs (neutropenia, anemia, and thrombocytopenia) and discontinued niraparib but continued pembrolizumab. Of the seven patients administered dose level 2, one patient had a DLT and 1 had a DLT-equivalent (both thrombocytopenia); after interruption of niraparib, both patients resumed at 200 mg niraparib, and continued pembrolizumab throughout.

The RP2D was determined to be 200 mg niraparib per day orally and pembrolizumab 200 mg IV on day 1 of each 21-day cycle.

A grade of 3 or higher treatment-emergent adverse events (TEAEs) were reported in six of seven patients (85.7%) in dose level 1 and all seven patients in dose level 2. The most common treatment related adverse events (AEs), which were reported in at least two patients, are shown in Table 5.

TABLE 5

Phase 1 treatment-related grade ≥3 TEAEs occurring in ≥2 patients

| AE Term, n (%) | Dose Level 1 (n = 7) | Dose Level 2 (n = 7) | Overall (n = 14) |
|---|---|---|---|
| Anemia | 2 (28.6) | 3 (42.9) | 5 (35.7) |
| Thrombocytopenia | 1 (14.3) | 4 (57.1) | 5 (35.7) |
| Neutropenia | 1 (14.3) | 1 (14.3) | 2 (14.3) |
| Platelet count decreased | 0 | 2 (28.6) | 2 (14.3) |

Efficacy—Phase 1

Figure 4:
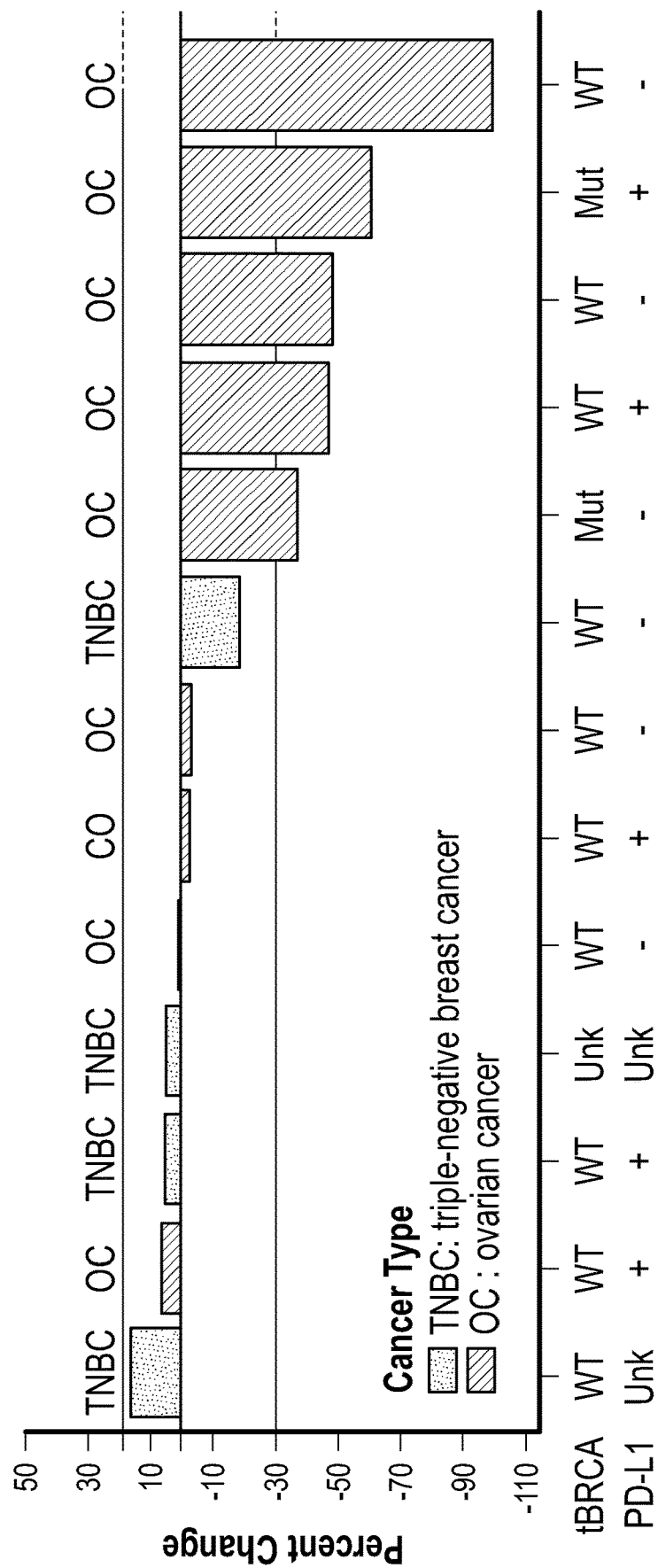
FIG. 4 depicts best percentage change in lesion size in patients enrolled in phase 1 of clinical study.

Partial (PR) or complete responses (CR) were observed in five of the nine patients evaluated with OC who had at least one scan; three of the responders had tumors that tested as wild-type tBRCA1/2 and three of the responders had tumors that tested as PD-L1 negative (<1%) (FIG. 4). Four of the remaining OC patients had stable disease. At the time of data collection, treatment was ongoing in two patients (48 and 54 weeks on study, respectively).

Of the four TNBC patients who had at least one scan, three patients had stable disease (FIG. 4). One additional TNBC patient came off study before the first on-study scan due to clinical progression.

Patients—Phase 2

At the time of data collection, 36 patients with OC and 47 patients with TNBC were enrolled in phase 2. For TNBC, 27 patients had at least one scan and eight patients had at least two scans. For OC, 29 patients had at least one scan and 13 patients had at least two scans. All patients were females. Demographics and baseline characteristics are shown in Table 6.

TABLE 6

Phase 2 demographics and baseline characteristics.

| | OC (n = 36) | TNBC (n = 47) |
|---|---|---|
| Age (years) | | |
| Median (min, max) | 60 (47, 83) | 54 (32, 90) |
| ECOG performance score, n (%) | | |
| 0 | 24 (66.7) | 26 (55.3) |
| 1 | 12 (33.3) | 21 (44.7) |
| Number of previous lines of therapy for advanced disease, median (range) | 3 (1-6) | 1 (0-3) |
| Patients with previous neoadjuvant/adjuvant therapies n (%) | 26 (72.2) | 36 (76.6) |
| Patients with previous platinum therapy n (%) | 36 (97.2) | 18 (38.3) |

Safety and Efficacy—Phase 2

No new safety signals were observed for phase 2. Additionally, less than 7% of phase 2 patients experienced grade ≥3 thrombocytopenia during the first treatment cycle. Thirty patients (36.1%) enrolled in phase 2 reported treatment-related grade ≥3 AEs (Table 7).

Subsequent to a protocol amendment, two patients who were escalated from 200 mg to 300 mg niraparib after two cycles had no grade ≥3 events.

TABLE 7

Phase 2 treatment-related grade ≥3 TEAEs occurring in ≥5% of patients.

|  | OC (n = 36) | TNBC (n = 47) | Overall (n = 83) |
|---|---|---|---|
| Patients with grade ≥3 TEAEs, n (%) | 16 (44.4) | 14 (29.8) | 30 (36.1) |
| Anemia | 6 (16.7) | 1 (2.1) | 7 (8.4) |
| Fatigue | 2 (5.6) | 3 (6.4) | 5 (6.0) |
| Platelet count decreased | 2 (5.6) | 3 (6.4) | 5 (6.0) |
| Thrombocytopenia | 1 (2.8) | 4 (8.5) | 5 (6.0) |

Figure 5A:
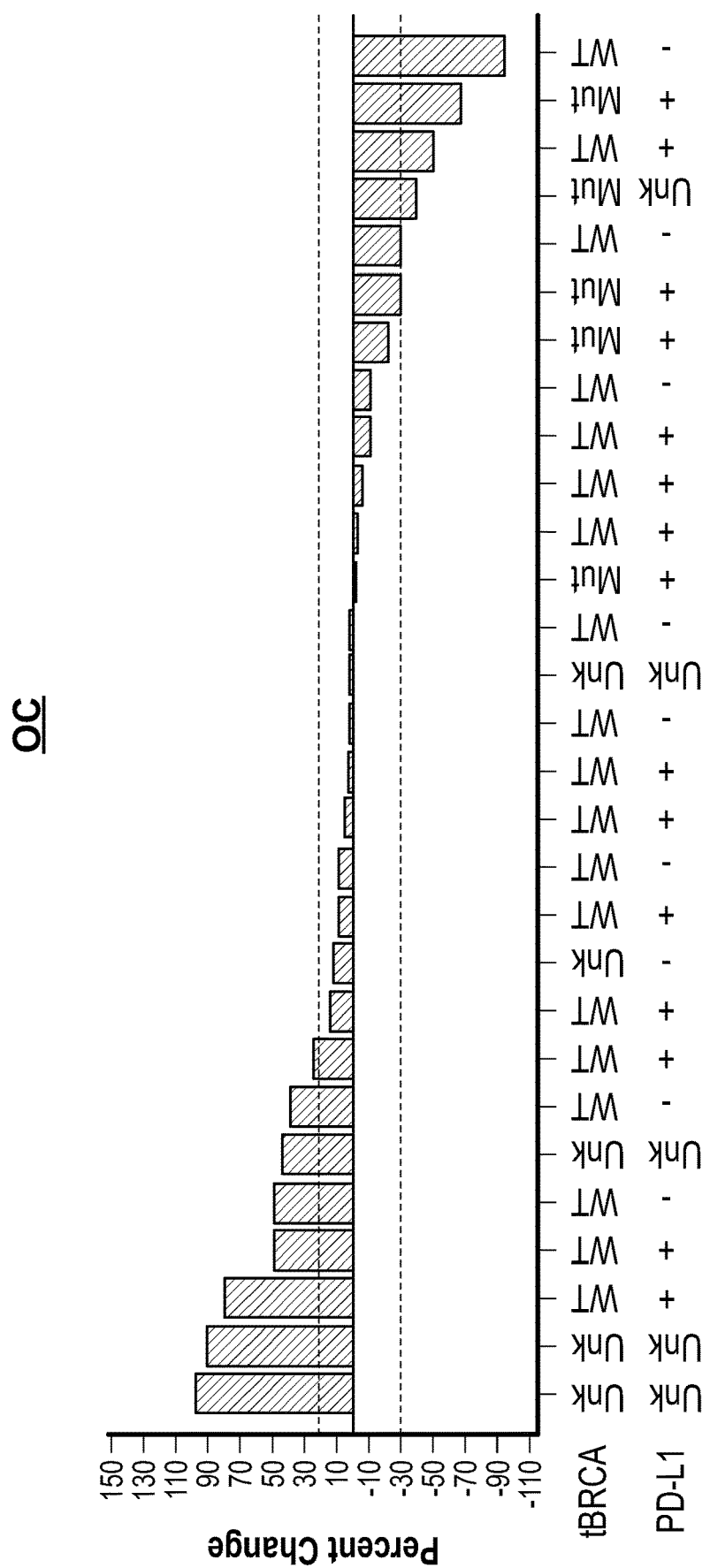
FIG. 5A and FIG. 5B depict preliminary best percentage change in lesion size in patients enrolled in Phase 2 with recurrent platinum-resistant ovarian cancer (OC) and advanced or metastatic triple-negative breast cancer (TNBC), respectively.

As shown in FIG. 5A, stable disease, partial responses (PR), and complete responses (CR) were observed in OC patients. Responses were observed in patients that tested as wild-type tBRCA1/2 and PD-L1 negative.

Figure 5B:
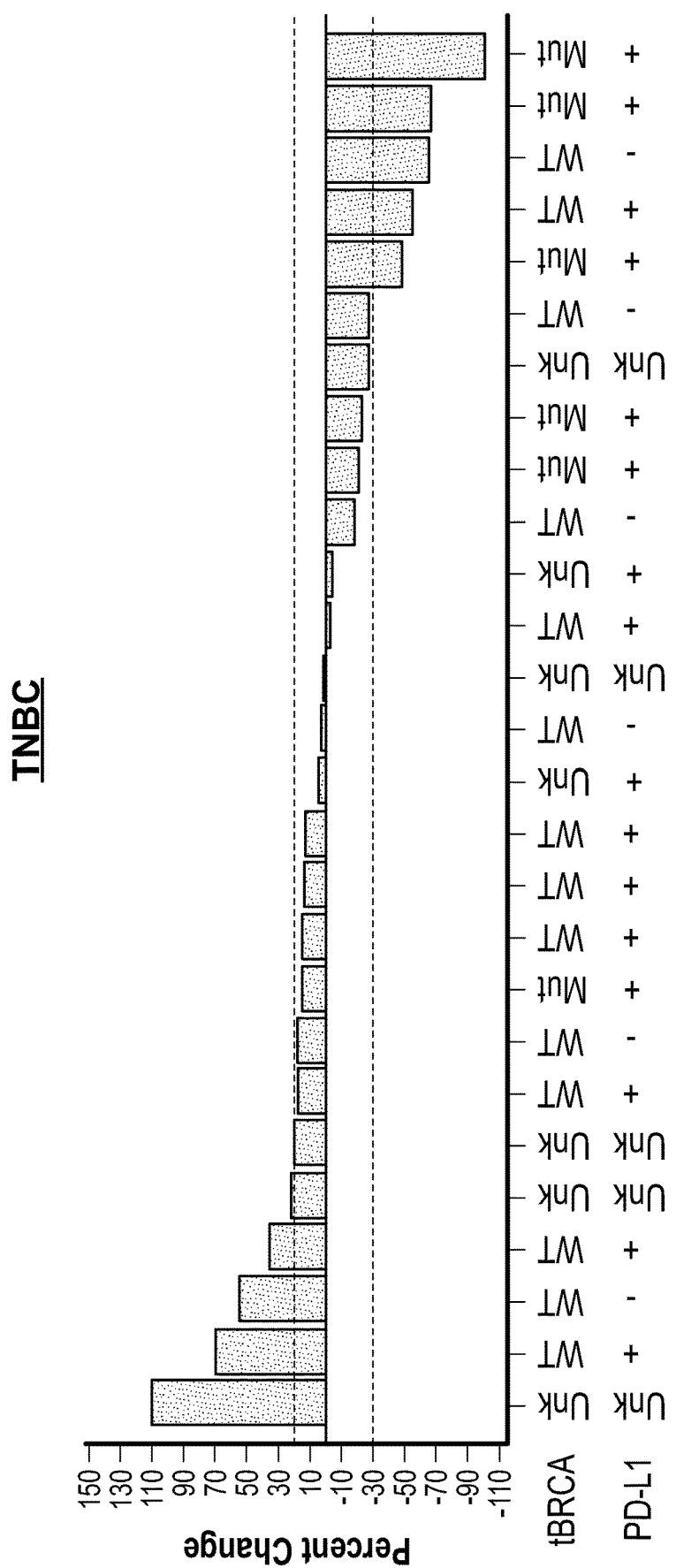

As shown in FIG. 5B, stable disease, partial responses (PR), and complete responses (CR) were observed in TNBC patients. Responses were observed in patients that tested as wild-type tBRCA1/2 and PD-L1 negative.

Conclusions

The recommended phase 2 dose of niraparib was established as 200 mg oral niraparib once daily (increasing to 300 mg after cycle 2 in patients who had no significant hematologic toxicities) in combination with 200 mg IV pembrolizumab on day 1 of each 21-day cycle. Additionally, no new safety signals have been identified.

Overall, treatment responses were observed in patients with BRCA wild-type and PD-L1 negative tumors in both ovarian and triple-negative breast cancer. These findings support the applicability of niraparib and pembrolizumab as a combination therapy in other tumors sensitive to anti-PD-1 therapy.

Example 4—Follow-Up Findings in TOPACIO Clinical Dose-Finding Combination Study

The following Example describes follow-up findings from phase 1 and phase 2 (TOPACIO; NCT02657889) of the above-described clinical study designed to evaluate combination treatment with niraparib and an anti-PD-1 agent (pembrolizumab) in patients with ovarian cancer (OC).

Clinical Study Objectives

As described in Example 3, the primary objective of phase 1 of this clinical study was to evaluate dose-limiting toxicities (DLTs) of combination treatment with niraparib and an anti-PD-1 agent, and establish a recommended phase 2 dose (RP2D) of niraparib to be administered with an anti-PD-1 agent. The objective of phase 2 was to estimate the clinical activity of combination treatment with niraparib and an anti-PD-1 agent for patients with recurrent platinum-resistant OC. Secondary objectives of phase 2 included an evaluation of the platinum responsiveness status of patients and the duration of response to combination treatment.

Methods

Inclusion Criteria

To be eligible for this study, patients with ovarian cancer were subjected to the following criteria. For the phase 1 and phase 2 populations, patients with epithelial ovarian, fallopian tube, or primary peritoneal cancer who were considered to have platinum-resistant disease and experienced a response lasting at least six months as a result of first-line platinum-based therapy were included. Patients who received up to five lines of cytotoxic therapy were included. Other key inclusion criteria for the study included measurable lesions by RECIST v1.1 and an Eastern Cooperative Oncology Group (ECOG) performance score of 0 or 1.

Exclusion Criteria

Patients with primary platinum refractory OC, such as progressive disease on or within 30 days of first-line platinum therapy, were excluded from the study. Additionally, patients who received prior treatment with an anti-PD-1, anti-PD-L1, or anti-PD-L2 agent or known PARP inhibitor were ineligible to participate in the study.

Clinical Study Design

As described in Example 3, dose-limiting toxicities (DLTs) were evaluated in a 6+6 dose escalation design (FIG. 3). The recommended phase 2 dose (RP2D) was determined based on the following: DLT rate in first and subsequent cycles of treatment, rate of a non-DLT adverse event (AE), dose modifications, pharmacokinetics, niraparib dose intensity, and signs of clinical efficacy. As described in Example 3, the RP2D was determined to be 200 mg niraparib per day orally and pembrolizumab 200 mg IV on day 1 of each 21-day cycle. Tumor BRCA (tBRCA) mutation status was evaluated using the Myriad Genetics research homologous recombination deficiency assay. Homologous recombination deficiency (HRD) status was evaluated using the following chromosomal markers: LOH (loss of heterozygosity), LST (large-scale state transitions), and TAI (telomeric allelic imbalance). PD-L1 expression was evaluated and the PD-L1 status was determined using a 1% provisional cutoff by immunohistochemistry (IHC) using an investigational version of the PD-L1 IHC 22C3 pharmDx (Agilent, Carpinteria, Calif., USA). The "combined positive score" was defined as the number of stained tumor and immune cells relative to total number of tumor cells.

In phase 2, patients with OC were evaluated using the RP2D of 200 mg niraparib per day orally and 200 mg intravenous (IV) pembrolizumab on day 1 of each 21-day cycle. The study was amended midway through to allow escalation of niraparib to 300 mg after 2 cycles in patients who did not have significant hematologic toxicity. The schedule of on-study assessments was as follows. The first scan was performed at nine weeks (±7 days). If progressive disease was apparent, a confirmatory scan was performed four weeks later. Subsequent scans were performed every nine weeks, and at the time of progression. If a complete response (CR) or partial response (PR) was observed, the response was confirmed by repeat imaging. A biomarker profile, including the status of tBRCA, HRD, and PD-L1 was established during phase 2 for OC patients.

Results

Patients—Phase 1 and Phase 2

Fourteen patients with OC were enrolled in phase 1 of the study and 9 patients were evaluated. At the time of data collection, 53 patients with OC were enrolled in phase 2 and the efficacy population included patients who received their week 9 scan (N=51). Patient demographics and baseline characteristics for the combination of phase 1 and phase 2 are shown in Table 8.

TABLE 8

Phase 1 and phase 2 patient demographics and baseline characteristics.

| Characteristics | Phase 1 and Phase 2 (N = 62 patients) |
|---|---|
| Median age (years) | 60.0 |
| ECOG performance status, n (%) | |
| 0 | 44 (71%) |
| 1 | 18 (29%) |

TABLE 8-continued

Phase 1 and phase 2 patient demographics and baseline characteristics.

| Characteristics | Phase 1 and Phase 2 (N = 62 patients) |
|---|---|
| Median prior therapies (range) | 2 (1-5%) |
| Previous bevacizumab therapy, n (%) | 39 (63%) |
| Previous chemotherapy in recurrent setting, n (%) | |
| Anthracycline | 38 (61%) |
| Cyclophosphamide | 5 (8%) |
| Gemcitabine | 28 (45%) |
| Paclitaxel | 60 (97%) |
| Platinum | 61 (98%) |
| Topotecan | 3 (5%) |

The most common prior treatments for OC patients were platinum-based therapy (received by 98% of patients) and paclitaxel (received by 97% of patients). For the combination of phase 1 and phase 2, the median age of patients was approximately 60 years. The median number of prior lines of chemotherapy was 2 with 18% of patients receiving one line of prior chemotherapy, 37% of patients receiving two lines of prior chemotherapy, and 45% of patients receiving at least three lines of prior chemotherapy (Table 8). With respect to ECOG performance status, approximately 71% of phase 1 and phase 2 patients had a score of 0 while approximately 29% of patients had a score of 1.

Figure 6:
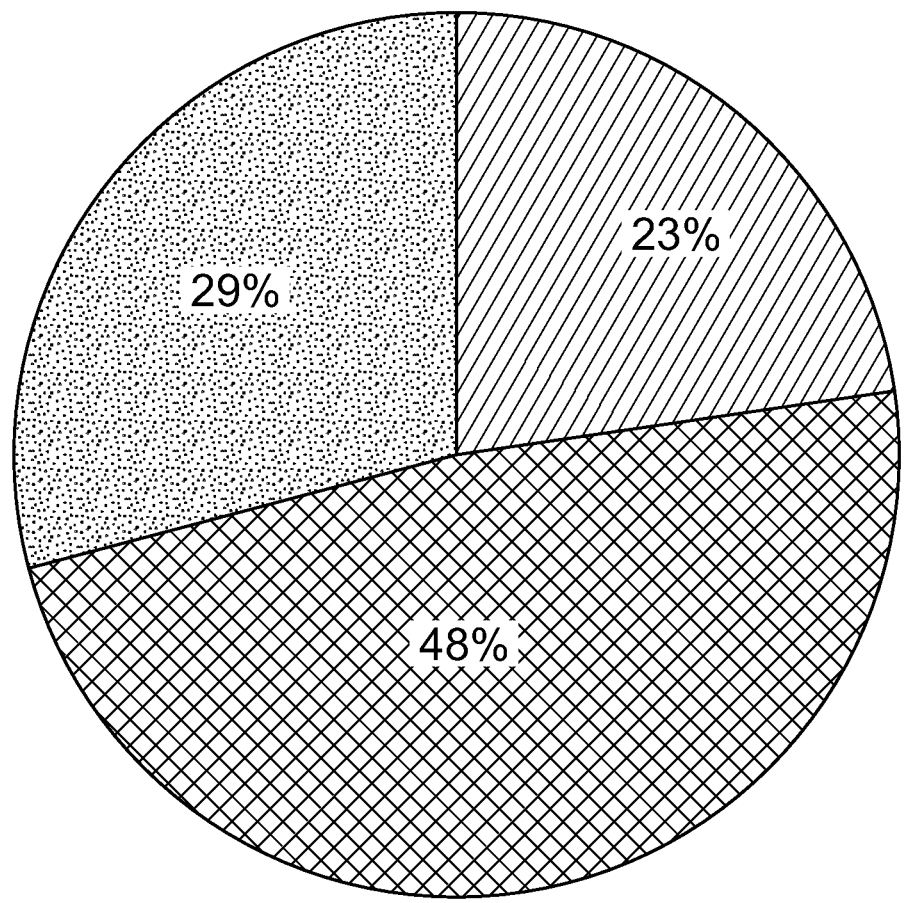
FIG. 6 depicts the platinum responsiveness status of patients based on platinum free interval (PFI) from the most recent line of platinum-based therapy.

Additionally, the platinum responsiveness status of phase 1 and phase 2 patients was evaluated (FIG. 6). 48% of phase 1 and phase 2 patients were found to be platinum-resistant, having a platinum free interval (PFI) from the last (most recent) line of prior platinum-based therapy of less than 6 months and showing tumor progression within this period. 29% of patients were found to be platinum-refractory, having a PFI from the last (most recent) line of prior platinum-based therapy of less than 30 days and showing tumor progression within this period. 23% of patients were found to be platinum-ineligible, having a platinum free interval (PFI) from the last (most recent) line of prior platinum-based therapy of at least 6 months, but who were removed from platinum treatment due to other reasons.

The biomarker profile for the combination of phase 1 and phase 2 patients was evaluated and the results are shown in Table 9.

TABLE 9

Biomarker Status

| Biomarker Status | Phase 1 and Phase 2 (N = 62)* |
|---|---|
| tBRCA | |
| BRCA1/2 mutant | 11 (18%) |
| WT | 45 (73%) |
| Not tested | 6 (9.7%) |
| HRD | |
| Positive | 22 (35%) |
| Negative | 31 (50%) |
| Inconclusive | 3 (4.8%) |
| Not tested | 6 (9.7%) |
| PD-L1 | |
| Positive | 33 (53%) |
| Negative | 21 (34%) |
| Not tested | 8 (13%) |

*Biomarker status assessed on N = 60 patients.
Two BRCA wild-type patients were not evaluable for efficacy.

Approximately 73% of phase 1 and phase 2 patients were found to have BRCA1/2 wild-type tumors while 18% of patients had tumors with mutations in BRCA1 or BRCA1 (Table 9). Approximately 50% of phase 1 and phase 2 patients were found to be HRD-negative, indicating wild-type status, while 35% of patients were HRD-positive, indicative of a deficiency in homologous recombination. Approximately 53% of phase 1 and phase 2 patients were found to have PD-L1 positive tumors while 34% of patients had PD-L1 negative tumors.

Treatment-emergent adverse events (TEAEs) occurring in at least 10% of patients were also reported for both phase 1 and phase 2 (Table 10). The most common TEAEs of any grade were found to be fatigue (45% of phase 1 and phase 2 patients) followed by nausea (42% of patients). The most common TEAEs of grade 3 or higher were reported to be an anemia event (19% of phase 1 and phase 2 patients) followed by a thrombocytopenia event (15% of patients). (85.7%).

TABLE 10

Phase 1 and phase 2 TEAEs in ≥10% patients

| Treatment-emergent adverse event | Any Grade (N = 53) | Grade ≥3 (N = 53) |
|---|---|---|
| Fatigue | 24 (45%) | 2 (4%) |
| Nausea | 22 (42%) | 1 (2%) |
| Constipation | 18 (34%) | 1 (2%) |
| Anemia event[1] | 16 (30%) | 10 (19%) |
| Thrombocytopenia event[2] | 20 (38%) | 8 (15%) |
| Decreased appetite | 11 (21%) | 1 (2%) |
| Vomiting | 10 (19%) | 1 (2%) |
| Neutropenia event[3] | 8 (15%) | 3 (6%) |
| Headache | 7 (13%) | 1 (2%) |
| Insomnia | 7 (13%) | 0 |
| Diarrhea | 6 (11%) | 1 (2%) |
| Dyspnea | 6 (11%) | 1 (2%) |

Figure 7:
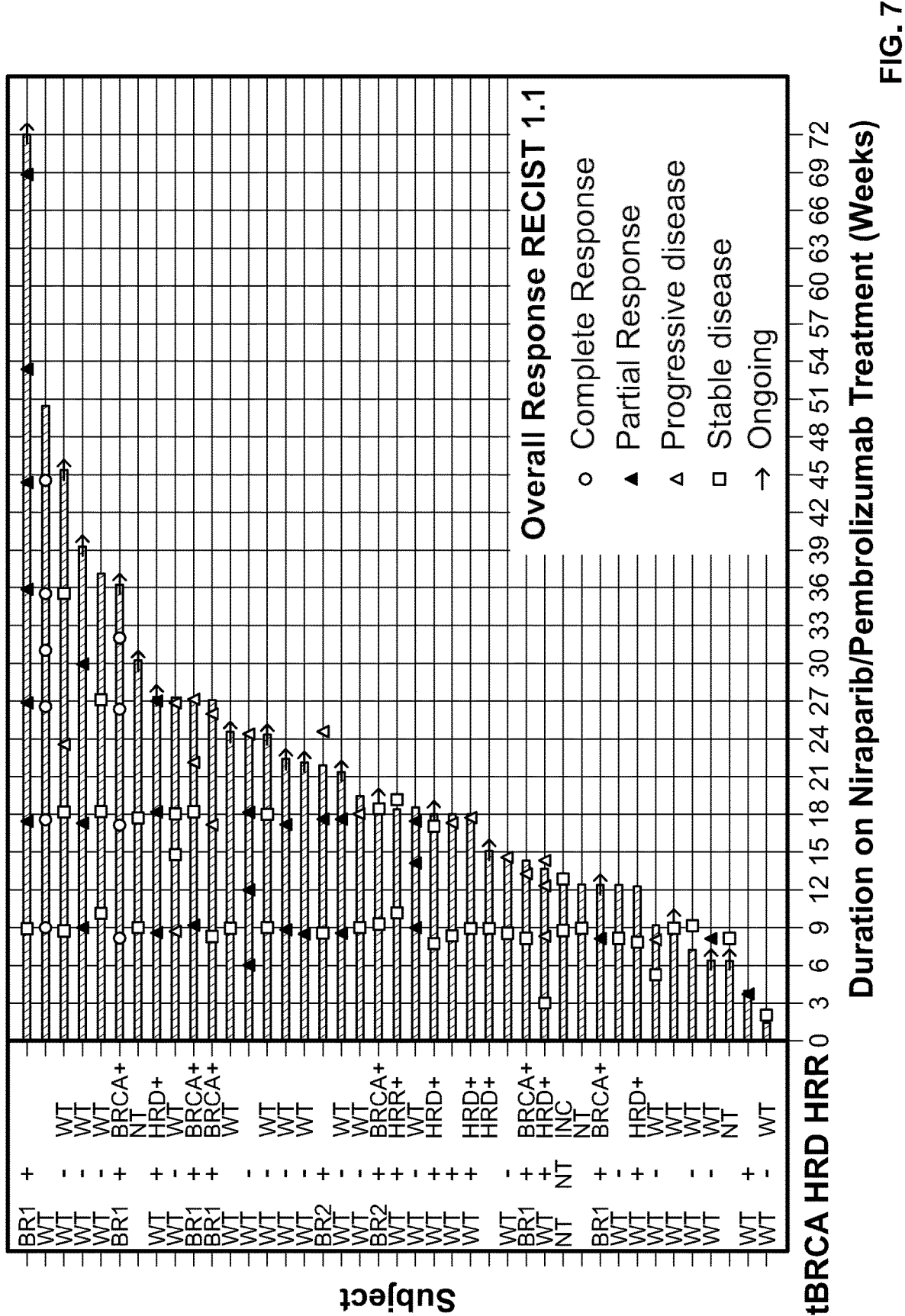
FIG. 7 depicts the duration of treatment for patients showing a complete response (CR), a partial response (PR), or stable disease.

[1]Anemia event: anemia and decreased hemoglobin count
[2]Thrombocytopenia event: thrombocytopenia and decreased platelet count
[3]Neutropenia event: neutropenia, neutropenic sepsis, and decreased neutrophil count Patient Response The efficacy of combination therapy in phase 1 and phase 2 patients at the time of data collection is shown in Table 11. The objective response rate (ORR), inclusive of patients showing a complete response (CR) or partial response (PR), was found to be 25%. Taking into account patients showing a partial response, complete response, or stable disease, the overall disease control rate was determined to be 68%. As shown in FIG. 7, approximately 33% of phase 1 and phase 2 patients overall remained on combination treatment as of the time of data collection with 18% of patients receiving at least six months of treatment. Additionally, approximately 60% (9/15) of phase 1 and phase 2 patients showing a partial or complete response remained on combination treatment as of the time of data collection. The median duration of response was approximately 9.3 months and the median progression-free survival was approximately 3.5 months in phase 1 and phase 2 patients (data not shown).

TABLE 11

Efficacy of combination treatment in phase 1 and phase 2 patients.

| | Phase 1 and Phase 2 (N = 60) | | |
|---|---|---|---|
| Patient Response | Number of patients | Percent of Patients | Patients Remaining on Treatment |
| Complete Response (CR) | 2 | 3% | 1 |
| Partial Response (PR) | 13 | 22% | 8 |
| Stable Disease (SD) | 26 | 43% | 9 |
| Progressive Disease (PD) | 19 | 32% | 2 |
| Objective Response Rate (ORR): CR + PR | 15 | 25% | |
| Disease control rate (DCR): CR+ PR + SD | 41 | 68% | |

Additionally, the efficacy of combination therapy in phase 1 and phase 2 patients having a specific biomarker status was evaluated and results are shown in Table 12.

TABLE 12

Efficacy of treatment in patients with a specific biomarker status.

| Platinum Status | Response | Total | tBRCA-mutant | HRD-positive[1] | tBRCA-wild-type | HRD-negative |
|---|---|---|---|---|---|---|
| All | ORR (%) | 15/60 (25%) | 5/11 (45%) | 7/22 (32%) | 10/44 (23%) | 8/33 (24%) |
| | DCR (%) | 41/60 (68%) | 8/11 (73%) | 17/22 (77%) | 29/44 (66%) | 20/33 (61%) |
| Platinum-resistant and Platinum-refractory | ORR (%) | 11/46 (24%) | 2/7 (29%) | 4/15 (27%) | 9/34 (26%) | 7/24 (29%) |
| | DCR (%) | 31/46 (67%) | 4/7 (57%) | 10/15 (67%) | 23/34 (68%) | 15/24 (63%) |

[1]Includes tBRCA-mutant genotype

Figure 8:
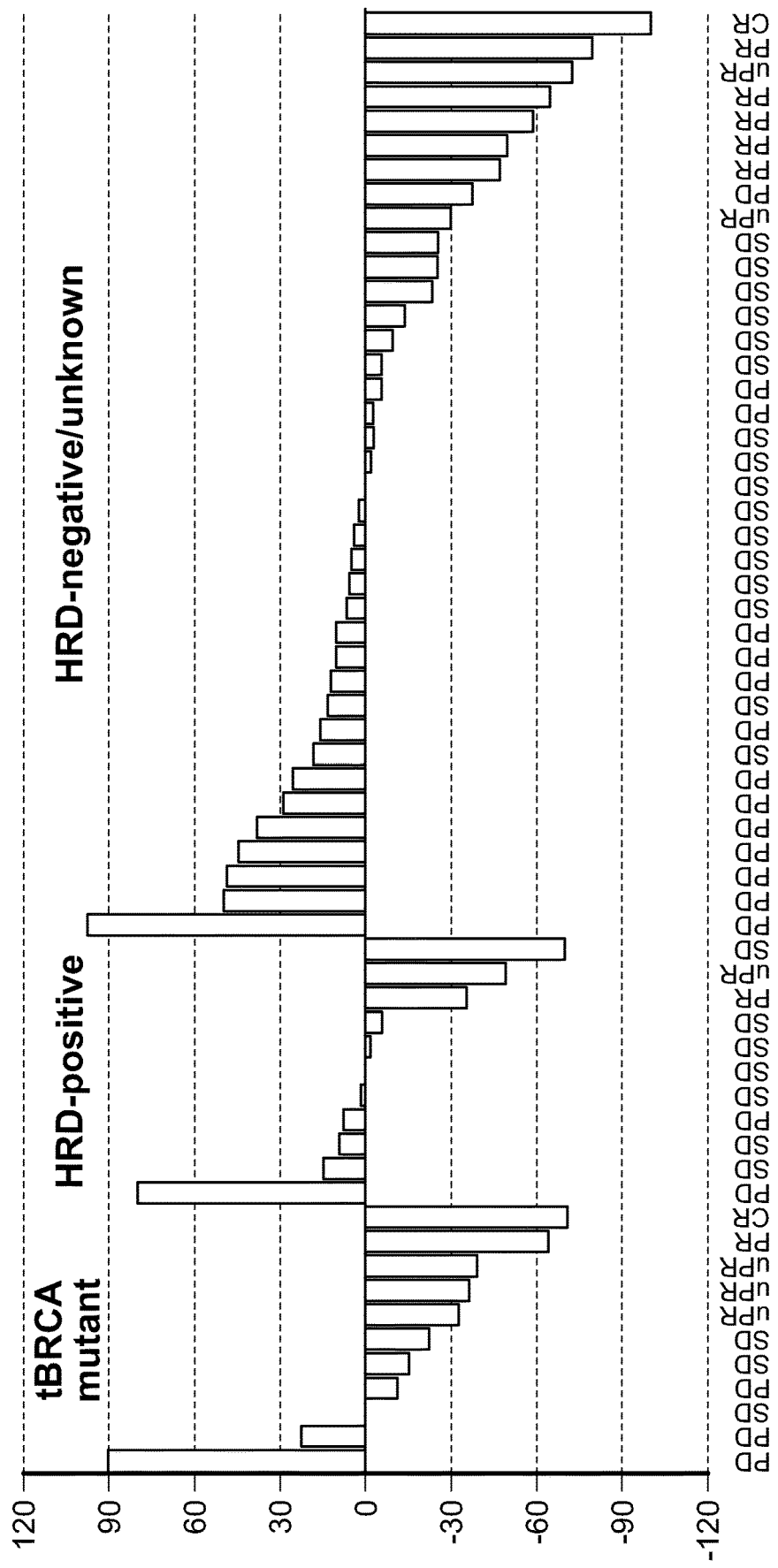
FIG. 8 depicts the treatment response observed in patients with ovarian cancer classified by biomarker status.

Responses were observed in phase 1 and phase 2 patients irrespective of tBRCA and HRD biomarker status as well as platinum responsiveness (FIG. 8 and Table 12). In general, patients with BRCA wild-type tumors showed an objective response rate (ORR) of 23% and a disease control rate of 66%. Patients with an HRD-negative status were found to have an ORR of 24% and a DCR of 61%.

Closer evaluation in the combined platinum-resistant and platinum-refractory populations indicated that patients with BRCA wild-type tumors displayed an ORR of 26% and a DCR of 68% while patients with an HRD-negative status were found to have an ORR and DCR of 29% and 63%, respectively.

Figure 9:
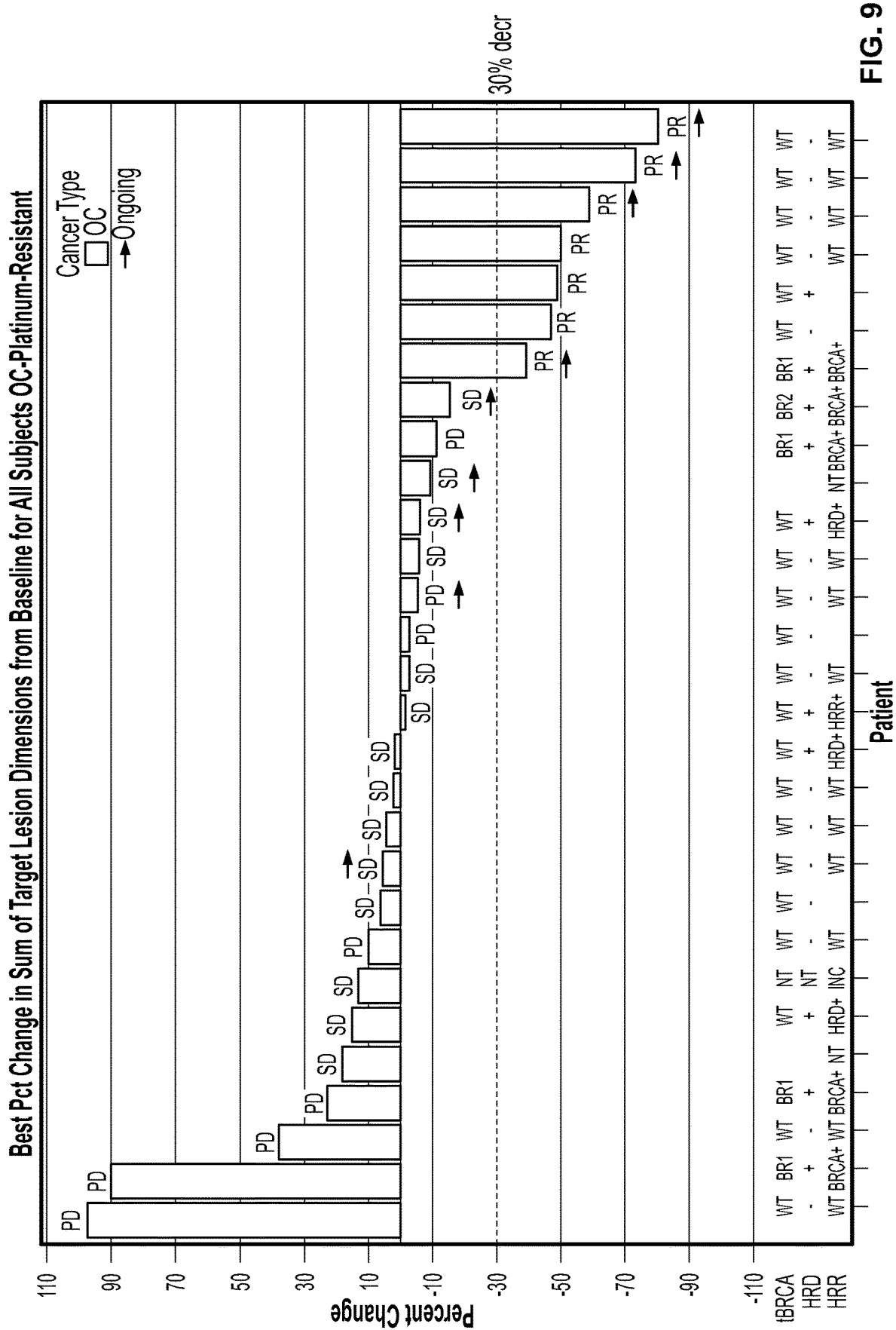
FIG. 9 depicts the treatment response observed in each platinum-resistant patient.

Analysis of the platinum-resistant population alone revealed that patients had an ORR of 24% and DCR of 72% irrespective of biomarker status (FIG. 9). Furthermore, platinum-resistant patients with BRCA wild-type tumors had an ORR of 29% and a DCR of 76%. Likewise, platinum-resistant patients with an HRD-negative status were found to have an ORR and DCR of 31% and 69%, respectively. Approximately 57% of platinum-resistant phase 1 and phase 2 patients showing a partial or complete response remained on combination treatment as of the time of data collection.

Figure 10:
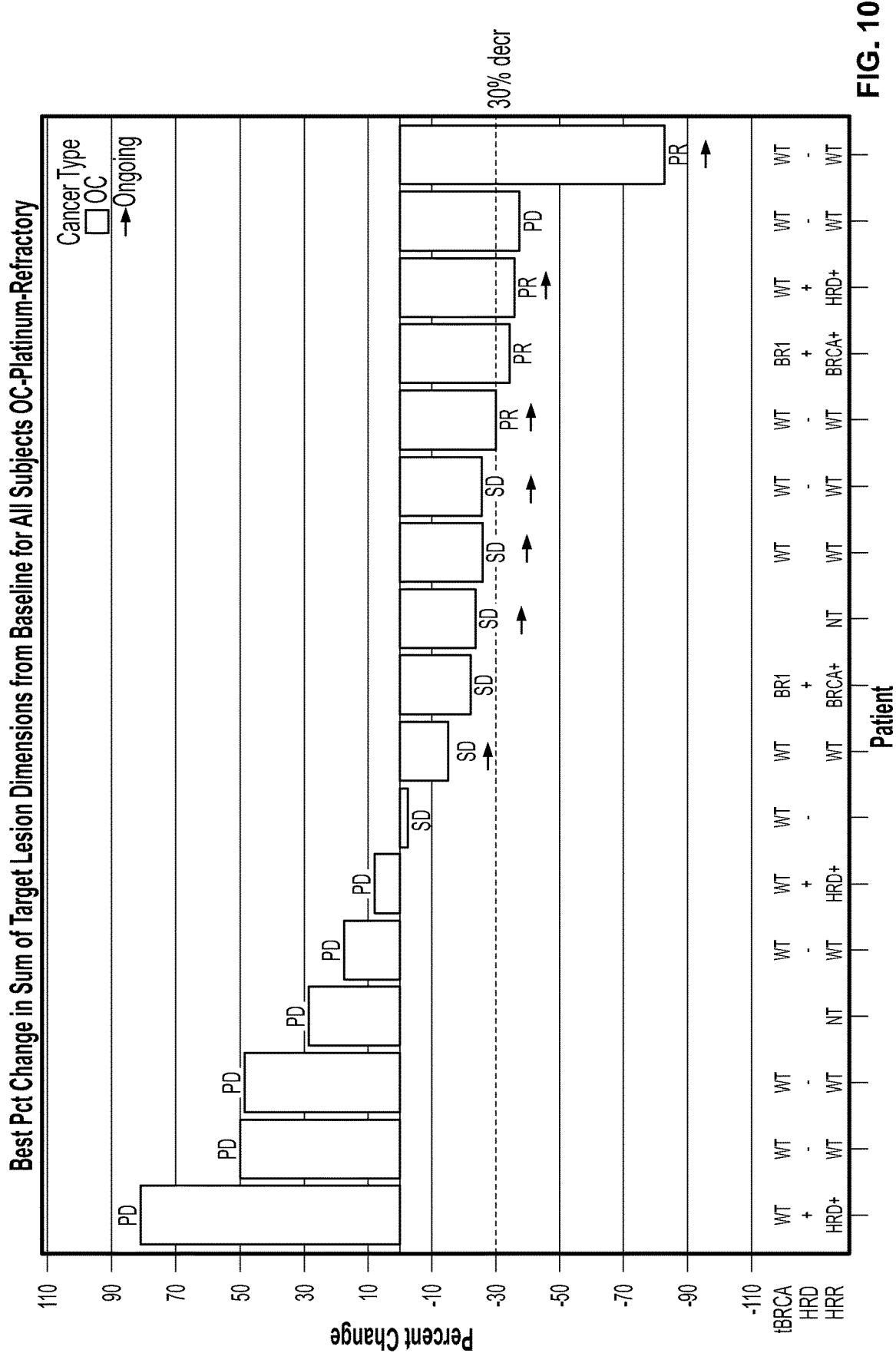
FIG. 10 depicts the treatment response observed in each patient showing progression of disease within 30 days of the last (most recent) line of platinum-based therapy (platinum refractory).

Within the platinum-refractory population, patients had an ORR of 24% and DCR of 59% irrespective of biomarker status (FIG. 10). It was found that approximately 12% of platinum-refractory patients had tumors with mutations in BRCA1 or BRCA2. Finally, 65% of platinum-refractory patients had received at least three lines of prior therapy and approximately 35% of platinum-refractory patients received combination treatment for at least six months.

Conclusions

The recommended phase 2 dose of niraparib was established as 200 mg oral niraparib once daily in combination with 200 mg IV pembrolizumab on day 1 of each 21-day cycle. It was determined that the niraparib dose could optionally be increased to 300 mg after cycle 2 in patients who had no significant hematologic toxicities. Additionally, no new safety signals were identified.

Overall, durable tumor regression and stabilization was observed in patients with ovarian cancer receiving the combination treatment of niraparib and pembrolizumab regardless of BRCA mutations or PD-L1 levels. The efficacy of the combination of niraparib and pembrolizumab in platinum-resistant or platinum-refractory patients irrespective of biomarker status indicates that the combination offers benefits to difficult-to-treat patients. Moreover, the combination of niraparib and a PD-1 inhibitor offers a possible alternative to chemotherapy as prolonged duration of treatment (up to at least 18 months) has been observed. The phase 1 and phase 2 data demonstrate the benefit of the combination of niraparib and PD-1 inhibitor for this high, unmet need patient population Example 5—Follow-Up Findings in TOPACIO Clinical Dose-Finding Combination Study for Patients with Advanced or Metastatic Triple-Negative Breast Cancer (TNBC)

The following Example describes follow-up findings from phase 1 and phase 2 (TOPACIO; NCT02657889) of the above-described clinical study designed to evaluate combination treatment with niraparib and an anti-PD-1 agent (pembrolizumab) in patients with advanced or metastatic triple-negative breast cancer (TNBC).

Clinical Study Objectives

As described in Example 3, the primary objective of phase 1 of this clinical study was to evaluate dose-limiting toxicities (DLTs) of combination treatment with niraparib and an anti-PD-1 agent, and establish a recommended phase 2 dose (RP2D) of niraparib to be administered with an anti-PD-1 agent. The objective of phase 2 was to estimate the clinical activity of combination treatment with niraparib and an anti-PD-1 agent for patients with advanced or metastatic TNBC. Secondary objectives of phase 2 included an evaluation of the duration of response to combination treatment. Progression-free survival was also evaluated for patients with advanced or metastatic TNBC receiving combination treatment.

Methods

Inclusion Criteria

To be eligible for this study, patients with TNBC were subjected to the following criteria. Patients with advanced or metastatic breast cancer that was estrogen receptor expression negative (<1% of cells), progesterone receptor expression negative (<1% of cells), and HER2-negative (i.e., TNBC) were included. Additionally, patients that demonstrated disease recurrence or progression following neoadjuvant and/or adjuvant therapy were included. A maximum of two prior lines of cytotoxic therapy was permitted during phase 2 of the trial. Adjuvant and/or neoadjuvant therapies were not counted in the number of lines of therapy. Patients who previously received platinum chemotherapy in the metastatic setting were allowed to enroll in the study if they did not progress while on or within eight weeks from the day of the last platinum administration.

Exclusion Criteria

Patients with advanced or metastatic TNBC who received prior treatment with an anti-PD-1, anti-PD-L1, or anti-PD-L2 agent or known PARP inhibitor were ineligible to participate in the study.

Clinical Study Design

As described in Example 3, dose-limiting toxicities (DLTs) were evaluated in a 6+6 dose escalation design (FIG. 3). The recommended phase 2 dose (RP2D) was determined based on the following: DLT rate in first and subsequent cycles of treatment, rate of a non-DLT adverse event (AE), dose modifications, pharmacokinetics, niraparib dose intensity, and signs of clinical efficacy. As described in Example 3, the RP2D was determined to be 200 mg niraparib per day orally in combination with pembrolizumab 200 mg IV on day 1 of each 21-day cycle. Tumor BRCA (tBRCA) mutation status was evaluated using the Myriad Genetics research homologous recombination deficiency assay. Homologous recombination deficiency (HRD) status was evaluated using the following chromosomal markers: LOH (loss of heterozygosity), LST (large-scale state transitions), and TAI (telomeric allelic imbalance). PD-L1 expression was evaluated and the PD-L1 status was determined using a 1% provisional cutoff by immunohistochemistry (IHC) using an investigational version of the PD-L1 IHC 22C3 pharmDx (Agilent, Carpinteria, Calif., USA). The "combined positive score" was defined as the number of stained tumor and immune cells relative to total number of tumor cells.

In phase 2, patients with TNBC were evaluated using the RP2D of 200 mg niraparib per day orally in combination with 200 mg intravenous (IV) pembrolizumab on day 1 of each 21-day cycle. The study was amended midway through to allow escalation of niraparib to 300 mg after 2 cycles in patients who did not have significant hematologic toxicity. The schedule of on-study assessments was as follows. The first scan was performed at nine weeks (±7 days) from the date of the first dose of treatment. If progressive disease was apparent, a confirmatory scan could be performed four weeks later. Subsequent scans were performed every nine weeks for the first year and every twelve weeks thereafter, and at the time of progression. If a complete response (CR) or partial response (PR) was observed, the response was confirmed by repeat imaging. A biomarker profile, including the status of tBRCA, HRD, and PD-L1 was established during phase 2 for TNBC patients. The efficacy population included patients who received any amount of study drug with at least one evaluable post-baseline tumor scan.

Conclusions

The recommended phase 2 dose of niraparib was established as 200 mg oral niraparib once daily in combination with 200 mg IV pembrolizumab on day 1 of each 21-day cycle. It was determined that the niraparib dose could optionally be increased to 300 mg after cycle 2 in patients who had no significant hematologic toxicities. Additionally, no new safety signals were identified.

Overall, durable tumor regression and stabilization was observed in patients with advanced or metastatic TNBC receiving the combination treatment of niraparib and pembrolizumab regardless of BRCA mutations, PD-L1 levels, or prior platinum exposure. The highest objective response rate, including both a complete or partial response, as well as progression-free survival was observed in patients with TNBC having tBRCA mutations. The efficacy of the combination of niraparib and pembrolizumab in platinum-resistant or platinum-refractory patients irrespective of biomarker status indicates that the combination offers benefits to difficult-to-treat patients. Moreover, the combination of niraparib and pembrolizumab offers a possible alternative to chemotherapy as prolonged duration of treatment (up to at least 12 months) has been observed. The phase 1 and phase 2 data demonstrate the benefit of the combination of niraparib and PD-1 inhibitor for this high, unmet need patient population.

EQUIVALENTS

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

The invention claimed is:

1. A method of treating cancer in a human subject that is homologous recombination deficiency (HRD)-negative, the method comprising:
   administering to the HRD-negative subject a therapeutically effective amount of niraparib or a salt thereof and pembrolizumab,
   wherein the niraparib or salt thereof is administered to the subject in a dose that is equivalent to 100, 200, or 300 mg of niraparib daily; and the pembrolizumab is administered at a therapeutically dose.

2. The method of claim 1, wherein the subject is gBRCA negative, tBRCA negative, or sBRCA negative.

3. The method of claim 1, wherein the niraparib or salt thereof and the pembrolizumab are administered according to a regimen that includes at least one 2-12 week treatment cycle.

4. The method of claim 1, wherein the niraparib or salt thereof and the pembrolizumab are administered in repeating cycles of 21 days.

5. The method of claim 3, wherein the pembrolizumab is administered on day one of cycle one.

6. The method of claim 5, wherein the pembrolizumab is administered on day one of a subsequent cycle.

7. The method of claim 5, wherein the pembrolizumab is administered between one to three days before or after day one of a subsequent cycle.

8. The method of claim 1, wherein the pembrolizumab is administered intravenously over about 60 minutes.

9. The method of claim 3, wherein the regimen includes at least 3 treatment cycles.

10. The method of claim 1, wherein the cancer is selected from the group consisting of: endometrial cancer, breast cancer, ovarian cancer, cervical cancer, fallopian tube cancer, primary peritoneal cancer, colon cancer, squamous cell carcinoma of the anogenital region, melanoma, renal cell carcinoma, lung cancer, non-small cell lung cancer, squamous cell carcinoma of the lung, stomach cancer, bladder cancer, gall bladder cancer, liver cancer, thyroid cancer, laryngeal cancer, salivary gland cancer, esophageal cancer, squamous cell carcinoma of the head and neck, prostate cancer, pancreatic cancer, mesothelioma, sarcoma, and a hematological cancer.

11. The method of claim 1, wherein the cancer is selected from the group consisting of: ovarian cancer, cervical cancer, fallopian tube cancer, primary peritoneal cancer, and triple negative breast cancer (TNBC).

12. The method of claim 1, wherein the cancer is recurrent cancer.

13. The method of claim 1, wherein the cancer is platinum resistant.

14. The method of claim 1, wherein the cancer is platinum refractory.

15. The method of claim 1, wherein the pembrolizumab is administered at a dose that is equivalent to 200 mg of pembrolizumab.

16. The method of claim 1, wherein the pembrolizumab is administered at a dose that is equivalent to 400 mg of pembrolizumab.

17. The method of claim 1, wherein the pembrolizumab is administered at a dose that is equivalent to 200 mg of pembrolizumab every 3 weeks.

18. The method of claim 1, wherein the pembrolizumab is administered at a dose that is equivalent to 400 mg of pembrolizumab every 6 weeks.

19. The method of claim 1, wherein the pembrolizumab is administered at a dose that is equivalent to 2 mg/kg of pembrolizumab.

20. The method of claim 1, wherein the pembrolizumab is administered at a dose that is equivalent to 5 mg/kg of pembrolizumab.

21. The method of claim 1, wherein the niraparib or salt thereof is administered to the subject in a dose that is equivalent to 100 mg of niraparib daily.

22. The method of claim 1, wherein the niraparib or salt thereof is administered to the subject in a dose that is equivalent to 200 mg of niraparib daily.

23. The method of claim 1, wherein the niraparib or salt thereof is administered to the subject in a dose that is equivalent to 300 mg of niraparib daily.

24. The method of claim 1, wherein the cancer is selected from the group consisting of: lung cancer, non-small cell lung cancer, and squamous cell carcinoma of the lung.

* * * * *

UNITED STATES PATENT AND TRADEMARK OFFICE
CERTIFICATE OF CORRECTION

PATENT NO. : 12,156,872 B2  
APPLICATION NO. : 16/612363  
DATED : December 3, 2024  
INVENTOR(S) : Dmitri Bobilev et al.

Page 1 of 1

It is certified that error appears in the above-identified patent and that said Letters Patent is hereby corrected as shown below:

In the Claims

Claim 1, Column 75, Line 58, "therapeutically dose" should read as --therapeutically effective dose--.

Signed and Sealed this
Fourteenth Day of January, 2025

Derrick Brent
*Acting Director of the United States Patent and Trademark Office*

SEQUENCE LISTING

<160> NUMBER OF SEQ ID NOS: 10

<210> SEQ ID NO 1
<211> LENGTH: 447
<212> TYPE: PRT
<213> ORGANISM: Artificial Sequence
<220> FEATURE:
<223> OTHER INFORMATION: Synthetic Construct

<400> SEQUENCE: 1

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu

```
                355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Leu Gly Lys
                435                 440                 445

<210> SEQ ID NO 2
<211> LENGTH: 218
<212> TYPE: PRT
<213> ORGANISM: Artificial Sequence
<220> FEATURE:
<223> OTHER INFORMATION: Synthetic Construct

<400> SEQUENCE: 2

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Lys Gly Val Ser Thr Ser
            20                  25                  30
Gly Tyr Ser Tyr Leu His Trp Tyr Gln Gln Lys Pro Gly Gln Ala Pro
        35                  40                  45
Arg Leu Leu Ile Tyr Leu Ala Ser Tyr Leu Glu Ser Gly Val Pro Ala
    50                  55                  60
Arg Phe Ser Gly Ser Gly Ser Gly Thr Asp Phe Thr Leu Thr Ile Ser
65                  70                  75                  80
Ser Leu Glu Pro Glu Asp Phe Ala Val Tyr Tyr Cys Gln His Ser Arg
                85                  90                  95
Asp Leu Pro Leu Thr Phe Gly Gly Gly Thr Lys Val Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215

<210> SEQ ID NO 3
<211> LENGTH: 117
<212> TYPE: PRT
<213> ORGANISM: Artificial Sequence
<220> FEATURE:
<223> OTHER INFORMATION: Synthetic Construct

<400> SEQUENCE: 3
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Gly Gly Gly Ser Tyr Thr Tyr Tyr Gln Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Tyr Tyr Ala Met Asp Tyr Trp Gly Gln Gly Thr Thr Val
            100                 105                 110

Thr Val Ser Ser Ala
        115

<210> SEQ ID NO 4
<211> LENGTH: 108
<212> TYPE: PRT
<213> ORGANISM: Artificial Sequence
<220> FEATURE:
<223> OTHER INFORMATION: Synthetic Construct

<400> SEQUENCE: 4

Asp Ile Gln Leu Thr Gln Ser Pro Ser Phe Leu Ser Ala Tyr Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Leu His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln His Tyr Ser Ser Tyr Pro Trp
                85                  90                  95

Thr Phe Gly Gln Gly Thr Lys Leu Glu Ile Lys Arg
            100                 105

<210> SEQ ID NO 5
<211> LENGTH: 10
<212> TYPE: PRT
<213> ORGANISM: Artificial Sequence
<220> FEATURE:
<223> OTHER INFORMATION: Synthetic Construct

<400> SEQUENCE: 5

Gly Phe Thr Phe Ser Ser Tyr Asp Met Ser
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic Construct

<400> SEQUENCE: 6

Thr Ile Ser Gly Gly Gly Ser Tyr Thr Tyr
```

```
<210> SEQ ID NO 7
<211> LENGTH: 7
<212> TYPE: PRT
<213> ORGANISM: Artificial Sequence
<220> FEATURE:
<223> OTHER INFORMATION: Synthetic Construct

<400> SEQUENCE: 7

Pro Tyr Tyr Ala Met Asp Tyr
1               5

<210> SEQ ID NO 8
<211> LENGTH: 11
<212> TYPE: PRT
<213> ORGANISM: Artificial Sequence
<220> FEATURE:
<223> OTHER INFORMATION: Synthetic Construct

<400> SEQUENCE: 8

Lys Ala Ser Gln Asp Val Gly Thr Ala Val Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct

<400> SEQUENCE: 9

Trp Ala Ser Thr Leu His Thr
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Construct

<400> SEQUENCE: 10

Gln His Tyr Ser Ser Tyr Pro Trp Thr
1               5
```